US007494777B2

(12) United States Patent
Blumenfeld et al.

(10) Patent No.: US 7,494,777 B2
(45) Date of Patent: *Feb. 24, 2009

(54) GENOMIC SEQUENCE OF THE 5-LIPOXYGENASE-ACTIVATING PROTEIN (FLAP), POLYMORPHIC MARKERS THEREOF AND METHODS FOR DETECTION OF ASTHMA

(75) Inventors: Marta Blumenfeld, Paris (FR); Ilya Chumakov, Vaux-le Penil (FR); Lydie Bougueleret, Petit-Lancy (CH)

(73) Assignee: Serono Genetics Institute S.A., Evry (FR)

( * ) Notice: Subject to any disclaimer, the term of this patent is extended or adjusted under 35 U.S.C. 154(b) by 240 days.

This patent is subject to a terminal disclaimer.

(21) Appl. No.: 11/512,789

(22) Filed: Aug. 29, 2006

(65) Prior Publication Data

US 2007/0003971 A1   Jan. 4, 2007

Related U.S. Application Data

(62) Division of application No. 10/359,512, filed on Feb. 5, 2003, now Pat. No. 7,118,869, which is a division of application No. 09/292,542, filed on Apr. 15, 1999, now Pat. No. 6,531,279.

(60) Provisional application No. 60/081,893, filed on Apr. 15, 1998, provisional application No. 60/091,314, filed on Jun. 30, 1998, provisional application No. 60/123,406, filed on Mar. 8, 1999.

(51) Int. Cl.
*C07H 21/04* (2006.01)
*C12Q 1/68* (2006.01)

(52) U.S. Cl. ................. 435/6; 435/91.1; 435/91.2; 536/23.1; 536/24.3

(58) Field of Classification Search .................. None
See application file for complete search history.

(56) References Cited

U.S. PATENT DOCUMENTS

| 5,182,367 A | 1/1993 | Gillard et al. |
| 5,578,443 A | 11/1996 | Santamaria et al. |
| 5,702,890 A | 12/1997 | Housman |
| 6,531,279 B1 | 3/2003 | Blumenfeld et al. |

FOREIGN PATENT DOCUMENTS

| CA | 2032253 | 6/1991 |
| WO | WO 95/35372 | 12/1995 |
| WO | WO 97/42347 | 11/1997 |

OTHER PUBLICATIONS

In, K. H. et al. "Naturally Occurring Mutations in the Human 5-lipoxygenase gene promoter that modify transcription factor binding and reporter gene transcription", *J. Clin. Invest.*, Mar. 1997, pp. 1130-1137, vol. 99, No. 5.

Morgan, L. et al. "DNA Polymorphisms and Linkage Disequilibrium in the Angiotensinogen Gene", *Human Genet.*, 1996, pp. 194-198, vol. 98.
Daniels, S. E. et al. "A Genome-Wide Search for Quantitative Trait Loci Underlying Asthma", *Nature*, 1996, pp. 247-250, vol. 383.
Dixon, R. A. F. et al. "Requirement of a 5-Lipoxygenase-Activating Protein for Leukotriene Synthesis", *Nature*, 1990, pp. 282-284, vol. 343.
Fan, J. et al. "Genetic Mapping: Finding and Analyzing Single-Nucleotide Polymorphisms with High-Density DNA arrays", *American Journal of Human Genetics*, 1997, p. 1601, vol. 61, No. 4.
Greally, M. et al. "The Genetics of Asthma", *Irish Medical Journal*, 1982, pp. 403-405, vol. 75, No. 11.
Hoshiko, S. et al. "Characterization of the Human 5-Lipoxygenase Gene Promoter", *Proc. Natl. Acad. Sci.*, 1990, pp. 9073-9077, vol. 87.
Kennedy, B. P. et al. "Gene Characterization and Promoter Analysis of the Human 5-Lipoxygenase Activating Protein (*FLAP*)", *The Journal of Biological Chemistry*, 1991, pp. 8511-8516, vol. 266, No. 13.
Kruglyak, L. "The Use of a Genetic Map of Biallelic Markers in Linkage Studies", *Nature Genetics*, 1997, pp. 21-24, vol. 17.
Mancini, et al. "The Binding of Leukotriene Biosynthesis Inhibitors to Site-Directed Mutants of Human 5-Lipoxygenase-Activating Protein", *Life Sciences*, 1994, pp. 137-142, vol. 54, No. 9.
Nicolaides, N. C. et al. "Interleukin 9: A Candidate Gene for Asthma", *Proc. Natl. Acad. Sci.*, 1997, pp. 13175-13180, vol. 94.
Noguchi, E. et al. "Evidence for Linkage Between Asthma/atopy in Childhood and Chromosome 5q31-q33 in a Japanese Population", *Am. J. Respir. Crit. Care Med.*, 1997, pp. 1390-1393, vol. 156.
Reid, G. K. et al. "Correlation Between Expression of 5-Lipoxygenase-Activating Protein, 5-Lipoxygenase, and Cellular Leukotriene Synthesis", *The Journal of Biological Chemistry*, 1990, pp. 19818-19823, vol. 265, No. 32.
Schork, T. et al. "Linkage Disequilibrium Mapping for Quantitative Traits Within Case/Control Settings", *American Journal of Human Genetics*, 1997, p. A283, vol. 61, No. 4.
Syvanen, A. C. et al. "Identification of Individuals by Analysis of Biallelic DNA Markers, Using PCR and Solid-Phase Minisequencing", *Am. J. Hum. Genet.*, 1993, pp. 46-59, vol. 52.
Thomas, N. S. et al. "The Candidate Region Approach to the Genetics of Asthma and Allergy", *Am. J. Respir. Crit. Care Med.*, 1997, pp. S144-S151, vol. 156.
Thomas, N. S. et al. "Candidate Locus Approach for Studying the Genetics of Asthma and Atopy", *Monaldi Arch Chest Dis*, 1997, pp. 296-302, vol. 52, No. 3.
Vickers, P. et al. "Cross-Species Comparison of 5-Lipoxygenase-Activating Protein", *Molecular Pharmacology*, 1992, pp. 1014-1019, vol. 42.

(Continued)

*Primary Examiner*—Jeanine A Goldberg
(74) *Attorney, Agent, or Firm*—Saliwanchik, Lloyd & Saliwanchik

(57) ABSTRACT

The invention concerns the genomic sequence of the FLAP gene. The invention also concerns biallelic markers of a FLAP gene and the association established between these markers and diseases involving the leukotriene pathway such as asthma. The invention provides means to determine the predisposition of individuals to diseases involving the leukotriene pathway as well as means for the diagnosis of such diseases and for the prognosis/detection of an eventual treatment response to agents acting on the leukotriene pathway.

6 Claims, 4 Drawing Sheets

OTHER PUBLICATIONS

Kedda, M.-A. et al. "Polymorphisms in the 5-Lipoxygenase Activating Protein (*ALOX5ZP*) Gene are Not Associated with Asthma in an Australian Population", *Clin. Exp. Allergy*, Mar. 2005, pp. 332-338, vol. 35.

Vickers, P. et al. "Amino Acid Residues of 5-Lipoxygenase-Activating Protein Critical for the Binding of Leukotriene Biosynthesis Inhibitors", *Journal of Lipid Mediators*, 1993, pp. 31-42, vol. 6.

Vickers, P. "5-Lipoxygenase-Activating Protein (*FLAP*)", *J. Lipid Mediators Cell Signaling*, 1995, pp. 185-194, vol. 12.

Voelkel, N. F. et al. "Inhibition of 5-Lipoxygenase-Activating Protein (*FLAP*) Reduces Pulmonary Vascular Reactivity and Pulmonary Hypertension in Hypoxic Rats", *J. Clin. Invest.*, 1996, pp. 2491-2498, vol. 97, No. 11.

Wang, et al. "Toward a Third Generation Genetic Map of the Human Genome Based on Bi-allelic Polymorphims", *American Journal of Human Genetics*, 1990, p. A03, vol. 59, No. 4.

Genbank X52195, Nov. 26, 1992.
Genbank M63262, Mar. 15, 1991.
Genbank M63261, Mar. 15, 1991.
Genbank M63260, Mar. 15, 1991.
Genbank M63259, Mar. 15, 1991.
Genbank M60470, Mar. 15, 1991.
EMBL, AA355068.1, Apr. 18, 1997.

Devlin, B. et al. "A Comparison of Linkage Disequilibrium Measures for Fine-Scale Mapping" *Genomics*, 1995, pp. 311-322, vol. 29.

Jorde, L. B. "Invited Editorial: Linkage Disequilibrium as a Gene-Mapping Tool" *American Journal of Human Genetics*, 1995, pp. 11-14, vol. 56.

Laan, M. et al. "Demographic history and linkage disequilibrium in human populations" *Nature Genetics*, Dec. 1997, pp. 435-438, vol. 17.

Morris, A. P. et al. "A likelihood ratio test for detecting patterns of disease-marker association" *Annual Human Genetics*, 1997, pp. 335-350, vol. 61.

Risch, N. et al. "The Future of Genetic Studies of Complex Human Diseases" *Science*, Sep. 13, 1996, pp. 1516-1517, vol. 273, No. 5281.

Wang, D. et al. "Large-Scale Identification, Mapping, and Genotyping of Single-Nucleotide Polymorphisms in the Human Genome" *Science*, May 15, 1998, pp. 1077-1082, vol. 280.

Ford-Hutchinson, A. W. "Regulation of leukotriene biosynthesis", *Cancer Metastasis Rev.*, Dec. 1994, pp. 257-267, vol. 13, Nos. 3-4, abstract only.

| MARKERS | 10-253/298 | 10-33/175 | 10-33/234 | 10-33/327 | 10-35/358 | 10-35/390 | 12-628/306 | 12-629/241 | ESTIMATED FREQUENCIES | | | |
|---|---|---|---|---|---|---|---|---|---|---|---|---|
| FLAP | 5'gene | ex2 | In2 | | In4 | | 3'gene | | Frequencies haplotype | | Odds ratio | Pvalue (1df) |
| cases/controls | 287/186 | 295/174 | 295/274 | 295/270 | 291/280 | 295/272 | 284/185 | 283/182 | | | | |
| case/controls freq % | 95/95 (C) | 99/98 (C) | 49/44 (A) | 78/76 (T) | 72/69 (G) | 31/23 (C) | 88/90 (C) | 76/72 (G) | cases | controls | | |
| diff.freq.all. (cases - controls) | 0,5 | 1,8 | 5,3 | 2,6 | 3,4 | 9 | 2,1 | 4,6 | | | | |
| pvalue | 6,55E-01 | 1,35E-02 | 6,93E-02 | 2,94E-01 | 2,06E-01 | 2,29E-03 | 3,17E-01 | 1,14E-01 | | | | |
| HAP 1  293 vs 265 | | | A | | | T | | | 0.283 | 0.197 | 1.61 | (8.2e-04) |
| HAP 2  281 vs 177 | | | A | | | | | G | 0.305 | 0.210 | 1.65 | (1.6e-03) |
| HAP 3  293 vs 261 | | | | T | | T | | | 0.307 | 0.224 | 1.53 | (1.8e-03) |
| HAP 4  289 vs 271 | | | | | G | T | | | 0.304 | 0.231 | 1.46 | (5.2e-03) |
| HAP 5  293 vs 168 | | C | | | | T | | | 0.309 | 0.226 | 1.53 | (6.9e-03) |
| HAP 6  293 vs 265 | | | A | T | | | | | 0.276 | 0.208 | 1.46 | (7.3e-03) |
| HAP 7  282 vs 178 | | | | | | T | | G | 0.314 | 0.233 | 1.50 | (7.7e-03) |
| HAP 37 281 vs 176 | | | A | | | T | C | | 0.265 | 0.171 | 1.76 | (8.6e-04) |
| HAP 38 280 vs 173 | | | A | | G | T | | G | 0.292 | 0.184 | 1.71 | (1.0e-03) |
| HAP 39 289 vs 264 | | | A | | G | T | | | 0.283 | 0.199 | 1.59 | (1.1e-03) |
| HAP 40 278 vs 175 | | | A | | | T | C | G | 0.271 | 0.180 | 1.70 | (1.6e-03) |
| HAP 41 284 vs 176 | C | | A | | | T | | | 0.287 | 0.195 | 1.66 | (1.7e-03) |
| HAP 121 277 vs 171 | | | A | | G | T | C | G | 0.265 | 0.169 | 1.77 | (8.6e-04) |
| HAP 122 278 vs 173 | | | A | | G | T | | G | 0.290 | 0.195 | 1.69 | (1.3e-03) |
| HAP 123 279 vs 176 | | | A | | G | T | C | | 0.264 | 0.175 | 1.70 | (1.7e-03) |
| HAP 124 276 vs 175 | | | A | | | T | C | G | 0.271 | 0.181 | 1.69 | (1.7e-03) |
| HAP 125 280 vs 174 | C | | A | | | T | | | 0.265 | 0.176 | 1.69 | (1.8e-03) |
| HAP 247 275 vs 171 | | | A | | G | T | C | G | 0.265 | 0.170 | 1.77 | (9.1e-04) |
| HAP 248 276 vs 169 | C | | A | | G | T | | G | 0.265 | 0.172 | 1.74 | (1.3e-03) |
| HAP 373 274 vs 169 | C | | A | | G | T | C | G | 0.265 | 0.172 | 1.73 | (1.4e-03) |
| HAP 457 273 vs 163 | C | | A | T | G | T | C | G | 0.247 | 0.167 | 1.64 | (5.2e-03) |

FIG. 3

| | Markers | 10-33/234 In2 A | | 10-35/390 In4 T | |
|---|---|---|---|---|---|
| ALT vs US | cases vs US controls | 5.3 (51 vs 56) | 6,93E-02 | 9 (31 vs 23) | 2,29E-03 |
| | cases vs FRENCH controls | 7.4 (49 vs 42) | 3,39E-02 | 9.2 (31 vs 22) | 1,75E-03 |
| ASSOCIATION | | diff all. Freq | pvalue | diff all. Freq | pvalue |

| HAPLOTYPE (AT) | sample sizes cases vs controls | haplotype frequencies | | p-excess | odds-ratio | P value | PERMUTATIONS TEST RESULTS | | |
|---|---|---|---|---|---|---|---|---|---|
| | | cases | controls | | | | Av. Chi-S | Max Chi-S | > Iter / nb of Iter. |
| Asthmatics vs US controls | 293 vs 265 | 0,283 | 0,197 | 10,7 | 1,61 | 8,20E-04 | 1,2 | 7,4 | 0/1000 |
| | | | | | | | 1,2 | 12,9 | 1/10 000 |
| Asthmatics vs FRENCH controls | 293 vs 154 | 0,283 | 0,192 | 11,33 | 1,67 | 2,70E-03 | 1,1 | 8,9 | 0/1000 |

FIG. 4

SEQUENCE LISTING

```
<160> NUMBER OF SEQ ID NOS: 15

<210> SEQ ID NO 1
<211> LENGTH: 43069
<212> TYPE: DNA
<213> ORGANISM: homo sapiens
<220> FEATURE:
<221> NAME/KEY: misc_feature
<222> LOCATION: 1..7708
<223> OTHER INFORMATION: potential 5'regulatory region
<220> FEATURE:
<221> NAME/KEY: misc_feature
<222> LOCATION: 36604..43069
<223> OTHER INFORMATION: potential 3'regulatory region
<220> FEATURE:
<221> NAME/KEY: exon
<222> LOCATION: 7709..7852
<223> OTHER INFORMATION: exon1
<220> FEATURE:
<221> NAME/KEY: exon
<222> LOCATION: 16236..16335
<223> OTHER INFORMATION: exon2
<220> FEATURE:
<221> NAME/KEY: exon
<222> LOCATION: 24227..24297
<223> OTHER INFORMATION: exon3
<220> FEATURE:
<221> NAME/KEY: exon
<222> LOCATION: 28133..28214
<223> OTHER INFORMATION: exon4
<220> FEATURE:
<221> NAME/KEY: exon
<222> LOCATION: 36128..36605
<223> OTHER INFORMATION: exon5
<220> FEATURE:
<221> NAME/KEY: misc_feature
<222> LOCATION: 7783..7785
<223> OTHER INFORMATION: ATG
<220> FEATURE:
<221> NAME/KEY: misc_feature
<222> LOCATION: 36288..36290
<223> OTHER INFORMATION: stop : TAA
<220> FEATURE:
<221> NAME/KEY: polyA_signal
<222> LOCATION: 36581..36586
<223> OTHER INFORMATION: AATAAA
<220> FEATURE:
<221> NAME/KEY: misc_feature
<222> LOCATION: 7008..8116
<223> OTHER INFORMATION: homology with sequence in ref genbank : M60470
<220> FEATURE:
<221> NAME/KEY: misc_feature
<222> LOCATION: 15995..16549
<223> OTHER INFORMATION: homology with sequence in ref genbank : M63259
<220> FEATURE:
<221> NAME/KEY: misc_feature
<222> LOCATION: 24059..24597
<223> OTHER INFORMATION: homology with sequence in ref genbank : M63260
<220> FEATURE:
<221> NAME/KEY: misc_feature
<222> LOCATION: 27873..28412
<223> OTHER INFORMATION: homology with sequence in ref genbank : M63261
```

```
<220> FEATURE:
<221> NAME/KEY: misc_feature
<222> LOCATION: 35977..36926
<223> OTHER INFORMATION: homology with sequence in ref genbank : M63262
<220> FEATURE:
<221> NAME/KEY: misc_feature
<222> LOCATION: 7613
<223> OTHER INFORMATION: diverging nucleotide deletion of a A in ref :
      M60470
<220> FEATURE:
<221> NAME/KEY: misc_feature
<222> LOCATION: 16347
<223> OTHER INFORMATION: diverging nucleotide G in ref : M63259
<220> FEATURE:
<221> NAME/KEY: misc_feature
<222> LOCATION: 16348
<223> OTHER INFORMATION: diverging nucleotide A in ref : M63259
<220> FEATURE:
<221> NAME/KEY: misc_feature
<222> LOCATION: 24060
<223> OTHER INFORMATION: diverging nucleotide deletion of a G in ref :
      M63260
<220> FEATURE:
<221> NAME/KEY: misc_feature
<222> LOCATION: 24067
<223> OTHER INFORMATION: diverging nucleotide deletion of a G in ref :
      M63260
<220> FEATURE:
<221> NAME/KEY: misc_feature
<222> LOCATION: 27903
<223> OTHER INFORMATION: diverging nucleotide deletion of a C in ref :
      M63261
<220> FEATURE:
<221> NAME/KEY: misc_feature
<222> LOCATION: 28327
<223> OTHER INFORMATION: diverging nucleotide deletion of a G in ref :
      M63261
<220> FEATURE:
<221> NAME/KEY: misc_feature
<222> LOCATION: 3851..4189
<223> OTHER INFORMATION: 10-517
<220> FEATURE:
<221> NAME/KEY: misc_feature
<222> LOCATION: 4120..4390
<223> OTHER INFORMATION: 10-518
<220> FEATURE:
<221> NAME/KEY: misc_feature
<222> LOCATION: 4373..4792
<223> OTHER INFORMATION: 10-253
<220> FEATURE:
<221> NAME/KEY: misc_feature
<222> LOCATION: 4814..5043
<223> OTHER INFORMATION: 10-499
<220> FEATURE:
<221> NAME/KEY: misc_feature
<222> LOCATION: 4956..5422
<223> OTHER INFORMATION: 10-500
<220> FEATURE:
<221> NAME/KEY: misc_feature
<222> LOCATION: 5524..5996
<223> OTHER INFORMATION: 10-522
<220> FEATURE:
<221> NAME/KEY: misc_feature
<222> LOCATION: 6218..6672
<223> OTHER INFORMATION: 10-503
<220> FEATURE:
<221> NAME/KEY: misc_feature
<222> LOCATION: 6522..6790
<223> OTHER INFORMATION: 10-504
<220> FEATURE:
<221> NAME/KEY: misc_feature
<222> LOCATION: 7120..7574
<223> OTHER INFORMATION: 10-204
<220> FEATURE:
<221> NAME/KEY: misc_feature
<222> LOCATION: 7513..7933
<223> OTHER INFORMATION: 10-32
<220> FEATURE:
<221> NAME/KEY: misc_feature
```

```
<222> LOCATION: 16114..16533
<223> OTHER INFORMATION: 10-33
<220> FEATURE:
<221> NAME/KEY: misc_feature
<222> LOCATION: 24072..24425
<223> OTHER INFORMATION: 10-34
<220> FEATURE:
<221> NAME/KEY: misc_feature
<222> LOCATION: 27978..28401
<223> OTHER INFORMATION: 10-35
<220> FEATURE:
<221> NAME/KEY: misc_feature
<222> LOCATION: 36020..36465
<223> OTHER INFORMATION: 10-36
<220> FEATURE:
<221> NAME/KEY: misc_feature
<222> LOCATION: 36318..36669
<223> OTHER INFORMATION: 10-498
<220> FEATURE:
<221> NAME/KEY: misc_feature
<222> LOCATION: 38441..38840
<223> OTHER INFORMATION: 12-629
<220> FEATURE:
<221> NAME/KEY: misc_feature
<222> LOCATION: 42233..42749
<223> OTHER INFORMATION: 12-628 complement
<220> FEATURE:
<221> NAME/KEY: allele
<222> LOCATION: 3950
<223> OTHER INFORMATION: 10-517-100 : polymorphic base S
<220> FEATURE:
<221> NAME/KEY: allele
<222> LOCATION: 4243
<223> OTHER INFORMATION: 10-518-125 : polymorphic base K
<220> FEATURE:
<221> NAME/KEY: allele
<222> LOCATION: 4312
<223> OTHER INFORMATION: 10-518-194 : polymorphic base R
<220> FEATURE:
<221> NAME/KEY: allele
<222> LOCATION: 4490
<223> OTHER INFORMATION: 10-253-118 : polymorphic base R
<220> FEATURE:
<221> NAME/KEY: allele
<222> LOCATION: 4670
<223> OTHER INFORMATION: 10-253-298 : polymorphic base S
<220> FEATURE:
<221> NAME/KEY: allele
<222> LOCATION: 4687
<223> OTHER INFORMATION: 10-253-315 : polymorphic base Y
<220> FEATURE:
<221> NAME/KEY: allele
<222> LOCATION: 4968
<223> OTHER INFORMATION: 10-499-155 : polymorphic base R
<220> FEATURE:
<221> NAME/KEY: allele
<222> LOCATION: 5140
<223> OTHER INFORMATION: 10-500-185 : polymorphic base Y
<220> FEATURE:
<221> NAME/KEY: allele
<222> LOCATION: 5213
<223> OTHER INFORMATION: 10-500-258 : polymorphic base K
<220> FEATURE:
<221> NAME/KEY: allele
<222> LOCATION: 5364
<223> OTHER INFORMATION: 10-500-410 : polymorphic base R
<220> FEATURE:
<221> NAME/KEY: allele
<222> LOCATION: 5594
<223> OTHER INFORMATION: 10-522-71 : polymorphic base R
<220> FEATURE:
<221> NAME/KEY: allele
<222> LOCATION: 6370
<223> OTHER INFORMATION: 10-503-159 : polymorphic base K
<220> FEATURE:
<221> NAME/KEY: allele
<222> LOCATION: 6693
<223> OTHER INFORMATION: 10-504-172 : polymorphic base W
<220> FEATURE:
```

-continued

```
<221> NAME/KEY: allele
<222> LOCATION: 6763
<223> OTHER INFORMATION: 10-504-243 : polymorphic base M
<220> FEATURE:
<221> NAME/KEY: allele
<222> LOCATION: 7445
<223> OTHER INFORMATION: 10-204-326 : polymorphic base R
<220> FEATURE:
<221> NAME/KEY: allele
<222> LOCATION: 7870
<223> OTHER INFORMATION: 10-32-357 : polymorphic base M
<220> FEATURE:
<221> NAME/KEY: allele
<222> LOCATION: 16288
<223> OTHER INFORMATION: 10-33-175 : polymorphic base Y
<220> FEATURE:
<221> NAME/KEY: allele
<222> LOCATION: 16347
<223> OTHER INFORMATION: 10-33-234 : polymorphic base M
<220> FEATURE:
<221> NAME/KEY: allele
<222> LOCATION: 16383
<223> OTHER INFORMATION: 10-33-270 : polymorphic base R
<220> FEATURE:
<221> NAME/KEY: allele
<222> LOCATION: 16440
<223> OTHER INFORMATION: 10-33-327 : polymorphic base Y
<220> FEATURE:
<221> NAME/KEY: allele
<222> LOCATION: 24361
<223> OTHER INFORMATION: 10-34-290 : polymorphic base K
<220> FEATURE:
<221> NAME/KEY: allele
<222> LOCATION: 28336
<223> OTHER INFORMATION: 10-35-358 : polymorphic base S
<220> FEATURE:
<221> NAME/KEY: allele
<222> LOCATION: 28368
<223> OTHER INFORMATION: 10-35-390 : polymorphic base Y
<220> FEATURE:
<221> NAME/KEY: allele
<222> LOCATION: 36183
<223> OTHER INFORMATION: 10-36-164 : polymorphic base R
<220> FEATURE:
<221> NAME/KEY: allele
<222> LOCATION: 36509
<223> OTHER INFORMATION: 10-498-192 : polymorphic base R
<220> FEATURE:
<221> NAME/KEY: allele
<222> LOCATION: 38681
<223> OTHER INFORMATION: 12-629-241 : polymorphic base S
<220> FEATURE:
<221> NAME/KEY: allele
<222> LOCATION: 42440
<223> OTHER INFORMATION: 12-628-311 : polymorphic base Y
<220> FEATURE:
<221> NAME/KEY: allele
<222> LOCATION: 42445
<223> OTHER INFORMATION: 12-628-306 : polymorphic base R
<220> FEATURE:
<221> NAME/KEY: misc_binding
<222> LOCATION: 3930..3949
<223> OTHER INFORMATION: 10-517-100.mis1 potential
<220> FEATURE:
<221> NAME/KEY: misc_binding
<222> LOCATION: 3951..3970
<223> OTHER INFORMATION: complement 10-517-100.mis2 potential
<220> FEATURE:
<221> NAME/KEY: misc_binding
<222> LOCATION: 4223..4242
<223> OTHER INFORMATION: 10-518-125.mis1 potential
<220> FEATURE:
<221> NAME/KEY: misc_binding
<222> LOCATION: 4244..4263
<223> OTHER INFORMATION: complement 10-518-125.mis2 potential
<220> FEATURE:
<221> NAME/KEY: misc_binding
<222> LOCATION: 4292..4311
<223> OTHER INFORMATION: 10-518-194.mis1 potential
```

```
<220> FEATURE:
<221> NAME/KEY: misc_binding
<222> LOCATION: 4313..4332
<223> OTHER INFORMATION: complement 10-518-194.mis2 potential
<220> FEATURE:
<221> NAME/KEY: misc_binding
<222> LOCATION: 4470..4489
<223> OTHER INFORMATION: 10-253-118.mis1 potential
<220> FEATURE:
<221> NAME/KEY: misc_binding
<222> LOCATION: 4491..4510
<223> OTHER INFORMATION: complement 10-253-118.mis2 potential
<220> FEATURE:
<221> NAME/KEY: misc_binding
<222> LOCATION: 4650..4669
<223> OTHER INFORMATION: 10-253-298.mis1
<220> FEATURE:
<221> NAME/KEY: misc_binding
<222> LOCATION: 4671..4690
<223> OTHER INFORMATION: complement 10-253-298.mis2 potential
<220> FEATURE:
<221> NAME/KEY: misc_binding
<222> LOCATION: 4667..4686
<223> OTHER INFORMATION: 10-253-315.mis1 potential
<220> FEATURE:
<221> NAME/KEY: misc_binding
<222> LOCATION: 4688..4707
<223> OTHER INFORMATION: complement 10-253-315.mis2 potential
<220> FEATURE:
<221> NAME/KEY: misc_binding
<222> LOCATION: 4948..4967
<223> OTHER INFORMATION: 10-499-155.mis1 potential
<220> FEATURE:
<221> NAME/KEY: misc_binding
<222> LOCATION: 4969..4988
<223> OTHER INFORMATION: complement 10-499-155.mis2 potential
<220> FEATURE:
<221> NAME/KEY: misc_binding
<222> LOCATION: 5120..5139
<223> OTHER INFORMATION: 10-500-185.mis1 potential
<220> FEATURE:
<221> NAME/KEY: misc_binding
<222> LOCATION: 5141..5160
<223> OTHER INFORMATION: complement 10-500-185.mis2 potential
<220> FEATURE:
<221> NAME/KEY: misc_binding
<222> LOCATION: 5193..5212
<223> OTHER INFORMATION: 10-500-258.mis1 potential
<220> FEATURE:
<221> NAME/KEY: misc_binding
<222> LOCATION: 5214..5233
<223> OTHER INFORMATION: complement 10-500-258.mis2 potential
<220> FEATURE:
<221> NAME/KEY: misc_binding
<222> LOCATION: 5344..5363
<223> OTHER INFORMATION: 10-500-410.mis1 potential
<220> FEATURE:
<221> NAME/KEY: misc_binding
<222> LOCATION: 5365..5384
<223> OTHER INFORMATION: complement 10-500-410.mis2 potential
<220> FEATURE:
<221> NAME/KEY: misc_binding
<222> LOCATION: 5574..5593
<223> OTHER INFORMATION: 10-522-71.mis1 potential
<220> FEATURE:
<221> NAME/KEY: misc_binding
<222> LOCATION: 5595..5614
<223> OTHER INFORMATION: complement 10-522-71.mis2 potential
<220> FEATURE:
<221> NAME/KEY: misc_binding
<222> LOCATION: 6350..6369
<223> OTHER INFORMATION: 10-503-159.mis1 potential
<220> FEATURE:
<221> NAME/KEY: misc_binding
<222> LOCATION: 6371..6390
<223> OTHER INFORMATION: complement 10-503-159.mis2 potential
<220> FEATURE:
<221> NAME/KEY: misc_binding
<222> LOCATION: 6673..6692
```

```
<223> OTHER INFORMATION: 10-504-172.mis1 potential
<220> FEATURE:
<221> NAME/KEY: misc_binding
<222> LOCATION: 6694..6713
<223> OTHER INFORMATION: complement 10-504-172.mis2 potential
<220> FEATURE:
<221> NAME/KEY: misc_binding
<222> LOCATION: 6743..6762
<223> OTHER INFORMATION: 10-504-243.mis1 potential
<220> FEATURE:
<221> NAME/KEY: misc_binding
<222> LOCATION: 6764..6783
<223> OTHER INFORMATION: complement 10-504-243.mis2 potential
<220> FEATURE:
<221> NAME/KEY: misc_binding
<222> LOCATION: 7425..7444
<223> OTHER INFORMATION: 10-204-326.mis1 potential
<220> FEATURE:
<221> NAME/KEY: misc_binding
<222> LOCATION: 7446..7465
<223> OTHER INFORMATION: 10-204-326.mis2 complement
<220> FEATURE:
<221> NAME/KEY: misc_binding
<222> LOCATION: 7850..7869
<223> OTHER INFORMATION: 10-32-357.mis1
<220> FEATURE:
<221> NAME/KEY: misc_binding
<222> LOCATION: 7871..7890
<223> OTHER INFORMATION: complement 10-32-357.mis2 potential
<220> FEATURE:
<221> NAME/KEY: misc_binding
<222> LOCATION: 16268..16287
<223> OTHER INFORMATION: 10-33-175.mis1
<220> FEATURE:
<221> NAME/KEY: misc_binding
<222> LOCATION: 16289..16308
<223> OTHER INFORMATION: complement 10-33-175.mis2 potential
<220> FEATURE:
<221> NAME/KEY: misc_binding
<222> LOCATION: 16327..16346
<223> OTHER INFORMATION: 10-33-234.mis1
<220> FEATURE:
<221> NAME/KEY: misc_binding
<222> LOCATION: 16348..16367
<223> OTHER INFORMATION: complement 10-33-234.mis2 potential
<220> FEATURE:
<221> NAME/KEY: misc_binding
<222> LOCATION: 16363..16382
<223> OTHER INFORMATION: 10-33-270.mis1
<220> FEATURE:
<221> NAME/KEY: misc_binding
<222> LOCATION: 16384..16403
<223> OTHER INFORMATION: complement 10-33-270.mis2 potential
<220> FEATURE:
<221> NAME/KEY: misc_binding
<222> LOCATION: 16420..16439
<223> OTHER INFORMATION: 10-33-327.mis1
<220> FEATURE:
<221> NAME/KEY: misc_binding
<222> LOCATION: 16441..16460
<223> OTHER INFORMATION: complement 10-33-327.mis2 potential
<220> FEATURE:
<221> NAME/KEY: misc_binding
<222> LOCATION: 24341..24360
<223> OTHER INFORMATION: 10-34-290.mis1
<220> FEATURE:
<221> NAME/KEY: misc_binding
<222> LOCATION: 24362..24381
<223> OTHER INFORMATION: complement 10-34-290.mis2 potential
<220> FEATURE:
<221> NAME/KEY: misc_binding
<222> LOCATION: 28316..28335
<223> OTHER INFORMATION: 10-35-358.mis1 potential
<220> FEATURE:
<221> NAME/KEY: misc_binding
<222> LOCATION: 28337..28356
<223> OTHER INFORMATION: 10-35-358.mis2 complement
<220> FEATURE:
<221> NAME/KEY: misc_binding
```

-continued

```
<222> LOCATION: 28348..28367
<223> OTHER INFORMATION: 10-35-390.mis1 potential
<220> FEATURE:
<221> NAME/KEY: misc_binding
<222> LOCATION: 28369..28388
<223> OTHER INFORMATION: complement 10-35-390.mis2 potential
<220> FEATURE:
<221> NAME/KEY: misc_binding
<222> LOCATION: 36163..36182
<223> OTHER INFORMATION: 10-36-164.mis1 potential
<220> FEATURE:
<221> NAME/KEY: misc_binding
<222> LOCATION: 36184..36203
<223> OTHER INFORMATION: 10-36-164.mis2 complement
<220> FEATURE:
<221> NAME/KEY: misc_binding
<222> LOCATION: 36489..36508
<223> OTHER INFORMATION: 10-498-192.mis1 potential
<220> FEATURE:
<221> NAME/KEY: misc_binding
<222> LOCATION: 36510..36529
<223> OTHER INFORMATION: complement 10-498-192.mis2 potential
<220> FEATURE:
<221> NAME/KEY: misc_binding
<222> LOCATION: 38661..38680
<223> OTHER INFORMATION: 12-629-241.mis1
<220> FEATURE:
<221> NAME/KEY: misc_binding
<222> LOCATION: 38682..38701
<223> OTHER INFORMATION: complement 12-629-241.mis2 potential
<220> FEATURE:
<221> NAME/KEY: misc_binding
<222> LOCATION: 42420..42439
<223> OTHER INFORMATION: 12-628-311.mis2 potential
<220> FEATURE:
<221> NAME/KEY: misc_binding
<222> LOCATION: 42441..42460
<223> OTHER INFORMATION: complement 12-628-311.mis1 potential
<220> FEATURE:
<221> NAME/KEY: misc_binding
<222> LOCATION: 42425..42444
<223> OTHER INFORMATION: 12-628-306.mis2 potential
<220> FEATURE:
<221> NAME/KEY: misc_binding
<222> LOCATION: 42446..42465
<223> OTHER INFORMATION: 12-628-306.mis1 complement
<220> FEATURE:
<221> NAME/KEY: misc_binding
<222> LOCATION: 3927..3973
<223> OTHER INFORMATION: 10-517-100.probe potential
<220> FEATURE:
<221> NAME/KEY: misc_binding
<222> LOCATION: 4220..4266
<223> OTHER INFORMATION: 10-518-125.probe potential
<220> FEATURE:
<221> NAME/KEY: misc_binding
<222> LOCATION: 4289..4335
<223> OTHER INFORMATION: 10-518-194.probe potential
<220> FEATURE:
<221> NAME/KEY: misc_binding
<222> LOCATION: 4467..4513
<223> OTHER INFORMATION: 10-253-118.probe potential
<220> FEATURE:
<221> NAME/KEY: misc_binding
<222> LOCATION: 4647..4693
<223> OTHER INFORMATION: 10-253-298.probe potential
<220> FEATURE:
<221> NAME/KEY: misc_binding
<222> LOCATION: 4664..4710
<223> OTHER INFORMATION: 10-253-315.probe potential
<220> FEATURE:
<221> NAME/KEY: misc_binding
<222> LOCATION: 4945..4991
<223> OTHER INFORMATION: 10-499-155.probe potential
<220> FEATURE:
<221> NAME/KEY: misc_binding
<222> LOCATION: 5117..5163
<223> OTHER INFORMATION: 10-500-185.probe potential
<220> FEATURE:
```

-continued

```
<221> NAME/KEY: misc_binding
<222> LOCATION: 5190..5236
<223> OTHER INFORMATION: 10-500-258.probe potential
<220> FEATURE:
<221> NAME/KEY: misc_binding
<222> LOCATION: 5341..5387
<223> OTHER INFORMATION: 10-500-410.probe potential
<220> FEATURE:
<221> NAME/KEY: misc_binding
<222> LOCATION: 5571..5617
<223> OTHER INFORMATION: 10-522-71.probe potential
<220> FEATURE:
<221> NAME/KEY: misc_binding
<222> LOCATION: 6347..6393
<223> OTHER INFORMATION: 10-503-159.probe potential
<220> FEATURE:
<221> NAME/KEY: misc_binding
<222> LOCATION: 6670..6716
<223> OTHER INFORMATION: 10-504-172.probe potential
<220> FEATURE:
<221> NAME/KEY: misc_binding
<222> LOCATION: 6740..6786
<223> OTHER INFORMATION: 10-504-243.probe potential
<220> FEATURE:
<221> NAME/KEY: misc_binding
<222> LOCATION: 7422..7468
<223> OTHER INFORMATION: 10-204-326.probe potential
<220> FEATURE:
<221> NAME/KEY: misc_binding
<222> LOCATION: 7847..7893
<223> OTHER INFORMATION: 10-32-357.probe potential
<220> FEATURE:
<221> NAME/KEY: misc_binding
<222> LOCATION: 16265..16311
<223> OTHER INFORMATION: 10-33-175.probe potential
<220> FEATURE:
<221> NAME/KEY: misc_binding
<222> LOCATION: 16324..16370
<223> OTHER INFORMATION: 10-33-234.probe potential
<220> FEATURE:
<221> NAME/KEY: misc_binding
<222> LOCATION: 16360..16406
<223> OTHER INFORMATION: 10-33-270.probe potential
<220> FEATURE:
<221> NAME/KEY: misc_binding
<222> LOCATION: 16417..16463
<223> OTHER INFORMATION: 10-33-327.probe potential
<220> FEATURE:
<221> NAME/KEY: misc_binding
<222> LOCATION: 24338..24384
<223> OTHER INFORMATION: 10-34-290.probe potential
<220> FEATURE:
<221> NAME/KEY: misc_binding
<222> LOCATION: 28313..28359
<223> OTHER INFORMATION: 10-35-358.probe potential
<220> FEATURE:
<221> NAME/KEY: misc_binding
<222> LOCATION: 28345..28391
<223> OTHER INFORMATION: 10-35-390.probe potential
<220> FEATURE:
<221> NAME/KEY: misc_binding
<222> LOCATION: 36160..36206
<223> OTHER INFORMATION: 10-36-164.probe potential
<220> FEATURE:
<221> NAME/KEY: misc_binding
<222> LOCATION: 36486..36532
<223> OTHER INFORMATION: 10-498-192.probe potential
<220> FEATURE:
<221> NAME/KEY: misc_binding
<222> LOCATION: 38658..38704
<223> OTHER INFORMATION: 12-629-241.probe potential
<220> FEATURE:
<221> NAME/KEY: misc_binding
<222> LOCATION: 42417..42463
<223> OTHER INFORMATION: 12-628-311.probe potential
<220> FEATURE:
<221> NAME/KEY: misc_binding
<222> LOCATION: 42422..42468
<223> OTHER INFORMATION: 12-628-306.probe potential
```

```
<220> FEATURE:
<221> NAME/KEY: primer_bind
<222> LOCATION: 3851..3869
<223> OTHER INFORMATION: upstream amplification primer 10-517
<220> FEATURE:
<221> NAME/KEY: primer_bind
<222> LOCATION: 4171..4189
<223> OTHER INFORMATION: downstream amplification primer 10-517
      complement
<220> FEATURE:
<221> NAME/KEY: primer_bind
<222> LOCATION: 4120..4138
<223> OTHER INFORMATION: upstream amplification primer 10-518
<220> FEATURE:
<221> NAME/KEY: primer_bind
<222> LOCATION: 4372..4390
<223> OTHER INFORMATION: downstream amplification primer 10-518
      complement
<220> FEATURE:
<221> NAME/KEY: primer_bind
<222> LOCATION: 4373..4391
<223> OTHER INFORMATION: upstream amplification primer 10-253
<220> FEATURE:
<221> NAME/KEY: primer_bind
<222> LOCATION: 4773..4792
<223> OTHER INFORMATION: downstream amplification primer 10-253
      complement
<220> FEATURE:
<221> NAME/KEY: primer_bind
<222> LOCATION: 4814..4833
<223> OTHER INFORMATION: upstream amplification primer 10-499
<220> FEATURE:
<221> NAME/KEY: primer_bind
<222> LOCATION: 5026..5043
<223> OTHER INFORMATION: downstream amplification primer 10-499
      complement
<220> FEATURE:
<221> NAME/KEY: primer_bind
<222> LOCATION: 4956..4972
<223> OTHER INFORMATION: upstream amplification primer 10-500
<220> FEATURE:
<221> NAME/KEY: primer_bind
<222> LOCATION: 5405..5422
<223> OTHER INFORMATION: downstream amplification primer 10-500
      complement
<220> FEATURE:
<221> NAME/KEY: primer_bind
<222> LOCATION: 5524..5542
<223> OTHER INFORMATION: upstream amplification primer 10-522
<220> FEATURE:
<221> NAME/KEY: primer_bind
<222> LOCATION: 5978..5996
<223> OTHER INFORMATION: downstream amplification primer 10-522
      complement
<220> FEATURE:
<221> NAME/KEY: primer_bind
<222> LOCATION: 6218..6235
<223> OTHER INFORMATION: upstream amplification primer 10-503
<220> FEATURE:
<221> NAME/KEY: primer_bind
<222> LOCATION: 6652..6672
<223> OTHER INFORMATION: downstream amplification primer 10-503
      complement
<220> FEATURE:
<221> NAME/KEY: primer_bind
<222> LOCATION: 6522..6539
<223> OTHER INFORMATION: upstream amplification primer 10-504
<220> FEATURE:
<221> NAME/KEY: primer_bind
<222> LOCATION: 6772..6790
<223> OTHER INFORMATION: downstream amplification primer 10-504
      complement
<220> FEATURE:
<221> NAME/KEY: primer_bind
<222> LOCATION: 7120..7137
<223> OTHER INFORMATION: upstream amplification primer 10-204
<220> FEATURE:
<221> NAME/KEY: primer_bind
<222> LOCATION: 7557..7574
```

```
<223> OTHER INFORMATION: downstream amplification primer 10-204
      complement
<220> FEATURE:
<221> NAME/KEY: primer_bind
<222> LOCATION: 7513..7531
<223> OTHER INFORMATION: upstream amplification primer 10-32
<220> FEATURE:
<221> NAME/KEY: primer_bind
<222> LOCATION: 7914..7933
<223> OTHER INFORMATION: downstream amplification primer 10-32
      complement
<220> FEATURE:
<221> NAME/KEY: primer_bind
<222> LOCATION: 16114..16132
<223> OTHER INFORMATION: upstream amplification primer 10-33
<220> FEATURE:
<221> NAME/KEY: primer_bind
<222> LOCATION: 16515..16533
<223> OTHER INFORMATION: downstream amplification primer 10-33
      complement
<220> FEATURE:
<221> NAME/KEY: primer_bind
<222> LOCATION: 24072..24089
<223> OTHER INFORMATION: upstream amplification primer 10-34
<220> FEATURE:
<221> NAME/KEY: primer_bind
<222> LOCATION: 24408..24425
<223> OTHER INFORMATION: downstream amplification primer 10-34
      complement
<220> FEATURE:
<221> NAME/KEY: primer_bind
<222> LOCATION: 27978..27995
<223> OTHER INFORMATION: upstream amplification primer 10-35
<220> FEATURE:
<221> NAME/KEY: primer_bind
<222> LOCATION: 28384..28401
<223> OTHER INFORMATION: downstream amplification primer 10-35
      complement
<220> FEATURE:
<221> NAME/KEY: primer_bind
<222> LOCATION: 36020..36039
<223> OTHER INFORMATION: upstream amplification primer 10-36
<220> FEATURE:
<221> NAME/KEY: primer_bind
<222> LOCATION: 36446..36465
<223> OTHER INFORMATION: downstream amplification primer 10-36
      complement
<220> FEATURE:
<221> NAME/KEY: primer_bind
<222> LOCATION: 36318..36337
<223> OTHER INFORMATION: upstream amplification primer 10-498
<220> FEATURE:
<221> NAME/KEY: primer_bind
<222> LOCATION: 36652..36669
<223> OTHER INFORMATION: downstream amplification primer 10-498
      complement
<220> FEATURE:
<221> NAME/KEY: primer_bind
<222> LOCATION: 38441..38460
<223> OTHER INFORMATION: upstream amplification primer 12-629
<220> FEATURE:
<221> NAME/KEY: primer_bind
<222> LOCATION: 38820..38840
<223> OTHER INFORMATION: downstream amplification primer 12-629
      complement
<220> FEATURE:
<221> NAME/KEY: primer_bind
<222> LOCATION: 42233..42253
<223> OTHER INFORMATION: downstream amplification primer 12-628
<220> FEATURE:
<221> NAME/KEY: primer_bind
<222> LOCATION: 42731..42749
<223> OTHER INFORMATION: upstream amplification primer 12-628 complement

<400> SEQUENCE: 1
gtgtcagctc agtcttgcgg gttttgggtt gtccttgctt cccacacttc atgcctttct      60
ttccctcctg acagtctgcc ctttagattt taggattcag caccagccac agaaacagca    120
```

-continued

```
acctcactgt taagggttga attgtatctc cccaaaaggt aggttgaggc cctacctgcc    180
aggacttcag aatgtaacct catttgggaa tagcatcatt gcaaatataa ttaattaaga    240
tgagggcata ctggctcagg atgggctcct aattcaatac aactaatgtc cttctacgac    300
agccacagga agacagaaac gccaagggag aacaccatat gctgatggag gcagtggcag    360
ctgccagcca aggattataa ccagaagtca ggaaaaagca agaaggaatc ctcccttagt    420
gattttacag ggagcatagc cctgctgaca ccttgatttt ggacttttat tccccaaaac    480
tgtaaaacaa tacacttctg ttgttttaag ccactcagtt tgtgctactt tgttatggca    540
actccagaaa acaaaaatac actcagactg tttaatcaac ctccataatt gcataaggtc    600
taatccctat aataaatccc ttaaaaatgt ctgtgtatat gtatttaaaa atataaaata    660
tcttctagtg gttctgcatc tctggtcaat ccctgactga tacagaatat gtattttcat    720
ttctaatgat gaaatacctg aatgaaattt ctaggacata tggtaagtgt atgtttagct    780
tttaagaaac tgccaacttg ggggaattgc ttgaggccag gagttcaaac agcctgggta    840
acagtgatac cctgtctgta caaaataaaa aatattagca gcgtgtggtg gtgtgtgtct    900
gtagtcccag ctactcagga ggctgaggtg ggagattcac ctgagcccag atctttgaag    960
ttatagtgag ctatgatcac gccactgcac tctagcctgg gtgacagagt gagaaagctg   1020
gtctctaaaa aacaaacaaa caaaaaagaa actgtcaaac tcttcccaac atgttgccat   1080
ttttacattt accattttac attcttacca gcaatgattg atagttccag ttgctccata   1140
cccttgctga ccattccaat agatgtattg tgttatctca ttgtagttct aatttgtatt   1200
tccctagtga ttaatgatgt ttaacatctt ttcatgcacc tattggctat atgtatatct   1260
tctttagcaa aatatatgtt gttatttgaa gagcggaagt tttacatttt gatgaagtct   1320
aatttattga ttttttttt cttagatggc tcatgctttt tgtgttatct aaaaaaaatt   1380
tgccttcttc atggtcacaa agactttctc ctatgttttc ttttggaagc tttatatttt   1440 tagttttat gtttatgttt aagacccatt tctagttaca atttgtgtga tttttggaa   1500 gggtcaaggt tcattttctt ttccataaga atgtacagtt gttctagcac ccttgttaaa   1560
aagactttcc tttccccatt gaactacttt gtcaaaaatc aactgagcat atatgggcat   1620
catgaatttt aatcctgtta gaactgaatg ttcccaaggc aggccatgcc catgactgac   1680
ctcctttcct tggattgcct acaaaacaga taaagctaag tctggagcaa agaaatccat   1740
gtctaacctg tatttttttt ttttttttt tttagatggg gtctcgctct gtcacccagg   1800
ctggagtgca gtggcgtgat cccagctcac tgcaatctct gcctcctggg ttcaagtgat   1860
tctcctgcct cagcctcccg aggggctggg attgtaggcg tgcaccacta tgcccatcta   1920 attttgtat ttttagtaga tagggttt tgccattttg gccagactgt cttgaactcc   1980
tgacctcagg tgatctgcct gcctcggcct cccacagttt tgtgattata ggcatgagcc   2040
accgtgcccg gccttaacct tgttttctt acacaacaca ctacgtgatg ttttccacat   2100
gcatgggtca tttgcttcat ttacgtacaa atgcataagc aatatactgt gtggtgtgag   2160
tttgtgatgg gaaaggaag aggttttgcg gatactacac tggcttcctg ctatctgtct   2220
gtgtgaatgg ctatggactt tgtcttctat ttgttcgctt agcgcagata tgatcagctt   2280
acaacttaag attctagaga aagagggtca tatctgtaaa gcactctgag catgtgtgaa   2340
gtttaatcaa tagcatatga ggttacagca aattcactat ctttgtttct tcagctatag   2400
aatggcatga ggattcatct caatttagtt caattctgtt cagaaccatg agctagctgt   2460
```

```
tcatggaagg aaagcccacc tgattgtggc cagggaagga gaaacaacac tttaaccagg    2520
ttgatttggt tctcacagac accattggca tgtgacatct ggaacagacc atgcctggtc    2580
tctgttcgta tcacttacca ttcagctcaa tattggtctg aatattcttt agactgactg    2640
aaatgaaaag gaactgttgt gtaaccatcc ataattccag cctgtagacc tgggctgtat    2700
ctctatgccc tgcctggcac agaccccacc tcctgctcct tctccctcac caccagtcaa    2760
tccttgtcct aatgaacagg gagggcaacc ctgaatgggg agtggaggga agagatgtca    2820
tgagatggca acgtgcaccc tgaagtgagg atgaaggcta tgtgaatgtt gtaggctgac    2880
agccgggcat agtgggcccg ttgccatggc gatggaggca tgttgatgcg aagtgtctgc    2940
acagctccta ggatttttaa cagcagctgg gcagagcctc ggcgtccctg aattgttgcc    3000
cccctgagtc actgcttggc cccagctgtc ctgatctctg ttgacaaatg gttgtccttc    3060
acagtcaaac tactaacagt actctaatta atgaatgtgc taattattct tgcctactcc    3120
cagcatattt gtctaactaa cctgtcacac acagatcagt gcagcatatg cataattacg    3180
gagagcgctg ggagcagggg atgggtggga gaggggtggg ctcgcagccc tgtcgctgtg    3240
ggatatttct tgtaaagtta cctttgctaa cggtcagatg tcgtgggdat atgttatttc    3300
ccgtgaagtg tatatgtctt cctttctttc ctttctaaga atctctcttc agggctgagg    3360
ggccattgct cagtgcttta gcctgtgagg ggattgccag gtacaaatgc agaaggacca    3420
gggagcccag gttctgaaga cgattccggt agcagcacgt agggtgatta aaactccaga    3480 cttttaaagcc agaccggcct gggcttgaac ccttgttctg ctccttgcta tgtgggtctt    3540
tgccttgacc acatttttt tttttttta agacaggatc tccctctctt gcccaggctg     3600
taatgcagtg ttgcgatcac agctcactga agcctccatc tctacagcct caagcgatcc    3660
tcctgcctca gccccgagta gctgggacta caggtctgtg ccaccacgtc cagctaattt    3720
acttttgtag agttggggt cttgctatgt tgcccaggct gttctccaac tcctggactc      3780
aagccatcct ctagcctcgg ccttccaaag tgctgggact ataggcgtga ccacggtgc     3840 caggcccttg accacatttt taaccctct gaacctcagt ttcactttct gggcaatggg     3900
aggggggtaa tttgtccctc agagggttgc actgagggc aaatgtgags ctctgggtac     3960
aatgcccagt acagactagg tccccacgac acagccgctc agcggctccg gattctgggc    4020
tgctctggac tgcggccagg cggtcttctg cgggaatccg ggcaggcagg gcgggctgcg    4080
ctcccctccc cggctctccc ggtgcccctt gtcttttgt tctgtctcag cagctctcta    4140
ttaagatgaa tggcatttcc aaaggcttca cctctgataa gtgttcctct gcagctgcag    4200
ccagaatctt aatgtgcgcg ctgtaattta atggccgtct cgkctattaa cacgctcttc    4260
tcgggtgaag tggactccct ccatccccgg gcctctgcac gtgctctgcg crctggctgg    4320
gggtgactcc aaggagctca gagcggggtg cccggcacct ctcgccaggc gcctttcgac    4380
cttctaaagc gcgaatggct ggacttttct cccatgtgtg gggccccaga aggtgtgggg    4440
ccccagaagg tgtggggtcc ctgcgttcca cggagcccgg aaggtttccr gtgatggtgg    4500
gggctgacca cgttggtccc cgtgggtgct gttttcatgt gccggcagat tgggatgagt    4560
ttaaaagaca gaagcgtgta ggatagagaa acttctttaa aaactggaaa ttttaatctg    4620
gggattataa ctattggaca gtcaagtgca agagtgaata cacttctcas tccctcctcc    4680
caatttytat ttgcgggatt agtcagtccc cctctgccac atgataattg tgagaactac    4740
cagggtcttc attctcctgc catctggttg acctctccaa gaatggacac ccgggcagcc    4800
tgggccaatg aggctgtcct aagagtttag atgagagaag tcagtctttg acaggtgatg    4860
```

```
gaagctgtaa aatgtaaaac tccacagttg gtgaagatgt ctccaggaaa caggtctgca   4920
gagagaatac gtttgacatg ctaagagaag ctgagagaga gcgagagrag agattggaag   4980
aaagacagag acagaggtag agagaaggga aagagagaga gaaagggaca gaagagagag   5040
aaaatagagg gggccgggcg cggtggctca cgcctgtaat ctcagcactt tgggaggccg   5100
aggcgggcag atcacgaggt caggagatcg agaccatccy ggctaacacg gtgaaacccc   5160
cgtctctact aaaaaatata aaaaaatta gccaggcgtg gtggtgggtg cckgtagtcc   5220
cagctactga ggaggctgag acaggagaat ggcgtgaacc cgggaggcag agcttgcagt   5280
gagctgagat cgcgccactg cactccagcc tgggcaacag agcaagactc cgtctcaaaa   5340
aaaaaaaaaa aaaagagagg aagrgcggga gagagagaga gagaaagctc tctagctcca   5400
aggcctaacc acatctctgt tcttttcaac ttcagctgtc agattttag actctttgag   5460 tgaataaatt ctccttttg cttaaactag ttcagctgtc agattttag actctttgag   5460
```

```
tgtgtgtgag acagtcttgc tctgttgccc aggctggagt gcagtggcat aatcattggc    7260
tcactgtagc ctcaaagtcc tgggcccaag cgatcttccc acctcagcca cccaaaatgc    7320
tggggttaca ggtttatgcc actctgtctg acctgaaagt tttgggttta ctttcccttc    7380
tttctctttg ctgaagtcag agatgatggc agcttccaga ttctctggtg cctgtgctgg    7440
gctcrtgctg gtcatggtct tgggtccagg attcattctg gagactctca gggaagtttc    7500
ccatgacaag gaaatgtagg agagtgtgct ggctttgcgt gctcctctgc caagccctgc    7560
ttctcctggt gggacacact gaaccacagc cagggcattt tggtggttag ttaaaaaaaa    7620
aaaaaaaaa aaaaaaggaa gaagaaggca ctgtgtaatt gtgccgggga tcttcagaaa    7680
ttgtaatgat gaaagagtgc aagctctcac ttccccttcc tgtacagggc aggttgtgca    7740
gctggaggca gagcagtcct ctctggggag cctgaagcaa acatggatca agaaactgta    7800
ggcaatgttg tcctgttggc catcgtcacc ctcatcagcg tggtccagaa tggtaaggaa    7860
agcccttcam tcaggaaga acagaagggg agatttctt tgatggttgt ttggaagtca     7920
ggcttaaaca attgtgtctg tgtgtgcgca tgcacaaaca cttttacctt atctttattt    7980
tcttcttttt atttgaatgt ataggggttgt gtgtatttct gtgtaaattt ggggttttcc   8040
tcctcttagt ctttcacttt tgtggtgatt accagtccca tttttagagc cagggctgca    8100
acttgaaggt tttgctaaaa ccctcaccga agtgtctatg atcagcattt taactattaa    8160
ttaatgtggc caggcaaggg gtggaaggtg agaagactag aaagggaaca tgatatacac    8220
atttactcag atactgggct tttctaacat ctgcagtgca attgaagtta ccagtcatct    8280
gcagtctaaa aagaaagtga ttttgggagg tgcgtagaaa aaatcatctt attattttc    8340
ctctatatta ctttttttctt ttttttctcct gaagaaactt tttttttgg tgataccttc   8400
ttttctcta gcacgtataa ttttggaagc attttttcata tgcagtgtat acttcagaaa    8460
gagagagaga gagaggaaaa ttgtcctgtt cagcgtttgc atttccatta ttcctgctat    8520
tagttaaaaa caacaacaac aacaaaaaac aagcaggata cctagatctg gaaaagggag    8580
aattgtgtag agctgtcttc ctaaagttct gagttagggc tgcctcagac cactttcata    8640
actatctcca gtggctttgt gttttatatt tattaagata gagaaaaaaa gagtaattac    8700
taagggcagc tgctgtagct ttatggtgat tactgaacat tgacatgctg tcacgttttt    8760
ggaactttga gtatttaatc actttgggat attctatttt cccccatctt gagtgtggac    8820
agatgctggt gatgtagcct tctgggcaca gagcaagcct cccctcagc ctctgcacca     8880
gaaaggctca gcttcacaca ctccaagtat gttttctaca agaactacac tttgtggctt    8940
tctgacccaa acatttttat actaaattac acacaacaaa gttgtagctc agagagggaa    9000
caaatggctt atttaggcca ccattttctt gagccattat gatttcacac agggctccct    9060
tggccctgta aattggcaag gattccatta ttcaacccgc atacatgtac agagaccctg    9120
ctctggccca gatagtattc tgggtacagg cggatagagc aggaaacaaa acagctacag    9180
tgatggacag gtcagcctgc agcaatgcct gcagtctctg caaaggtagc tgtatgggtg    9240
ggcaggtggc tagcacttat tcagctctgg aaggatctcc cctctggcct ctccctgac     9300
acccatcaat aaaactgagg agcatcggtg gacaggggac cttgtgcccc ctccctgcct    9360
gtgcagttgg ggctgaaccc agctacgaag tttgagctca ctctctccag ctccctctca    9420
attcagagct gaactgtggg aagcttcaga gctctctgtt tcaaggacag gttctcctca    9480
cctctcctaa tggaggtgca ccagggaact ggccctgctc tgcccagggc tttctcctgg    9540
actttgccat catggtctag caaaccctgt tcagattgag gtgagtggtg agatttcgaa    9600
```

```
ttcttttga cagataggat taagtcttct tctgtgggac aagtgggagg tagaggtaag   9660
attaaagatg gccaaatgtc tgagtcctga cagccacaat atggagatct agacttttta   9720
cagaccacag ggcacagggg cctcactaac agagttcccg gaagtgatga gtgtgctggg   9780
ggcttcctgg ttgaagagac actagaatgg acgagctggg agctaatttt ttgggctgga   9840
gtgtgatggc ctgcacatca ctgcctctgt ccctccattg tcacagctgc ccctaggag   9900
ccagctgagg caatttgtgg tcagagtgac tttgcacagt tgtcctgcct gtgttcagga   9960
agggagtttc tgtggtccct ttgaaaccac agaagagccc ctcgtatagc tctcaatgga  10020
gggggcaaaa cattcaaata actcaggaga taacacaact atttgttttt aactgtgagt  10080
ttttaggcaa tcacaaagat ccagatgtat gtccaagcct ctctttgcaa ttctatttaa  10140
cctcaatgtt gcaaccatag acctaccttta cagagttcaa aaaaatatgc aaaaaccctg  10200
cctttcttct tcctcatacc ccaaaatgcc attctgaaca tttcctgtta gttaaaaaaa  10260
gatttccatg gtgttaccag gcactgtaca cagtctgtgt cccaagacaa ggaggtacag  10320
ttccacatgc gcccatgact gggttgggct ctgcactctc tctatacttt gagagcctga  10380
ttttctgtga ttgggcagag ctggcccacc tggtgcaatg tcctcctctg cctttcaaac  10440
atgttttagt catcaagatc ttcaaatttg taacccttc cagcttgatc cagcagaatg  10500
cagatttgga aaaacagaac gagtttaaaa tacatgattc taagaaacct ggaccagaac  10560
tatcaaaact tggttttccca gagaatatag caaatgggct cattggccaa tactatgaca  10620
ttggcttttg agaaaagaaa ggcttattg caaggctggc cagcaaggag acaggagttg  10680
ggctcaaatc tgtctcccca gtttggggct tagggcaagt tttaattaca cagacgcatt  10740
tcttatgagt agcaggcaga gagcctccaa cttcttctgc ctaggtacca gcagcttaga  10800
catgatgcaa acctgggaag cacatactgt atttggagaa agtgattggg aagaaatgtg  10860
agctgagggg agggggctcag tgcccctgag ctacacttag tgatggcaga ggaaggatgt  10920
cctcccgcag gaggctgttc cacatctgct ctggttgtag ggggagctgg caggcattag  10980
cagcggcctc tttcccccaa gagaggcagc ctcctccaag ttttggcgac attatggccc  11040
tgcaatcata agggttttgtg agcatagtgc taaggaggga aatggagctg ctgttactag  11100
ttccaccca acacacacac acacactcac aagaaacctc acaagcaccg tattggaaga  11160
ctttgccatc caacctggga tttgacaggc tctagaagca gaatcataga ctcatgaagt  11220
tccccaaag caggaatctt ccttacagta acccccaacc accccctcc accgcctcca  11280
ccggctgctt cttcctgaac actgcagtgt ttggaaaact cacaaacttc caagcttgcc  11340
tttcctattg ttgcatggat tgaaagcttg cgttgtgtga agaatggcgc ttcctgctgt  11400
gcttagtttt atctcatata atctttgcac catttaatcc ttgcactcac ccactcatgc  11460
aactgccttt gcagagactg gaggggccgc tgtaggctga cctttccttc actgtaccta  11520
ttttgttccc tgcttattc ccctgcaccc aggacactgc ctggcacaaa gacaggtctt  11580
tataagtgta tgcaagtgaa taaagatata tatattatta ttgttatttt tgagacagtt  11640
tcactctgtc acccaggctg gagtgcagta gcgcaatctc agctgactgc aacctctgcc  11700
tcccaggctc aagtgattct catgtctcag cctcctgagt agctaggact acaagcatgt  11760
gccaccacgc ccagctaatt tttgtatttt tagtaaggac agggtttcac catgttggcc  11820
aggttggcct ccaactcctg acctcaagtc atcctcctgc ctcgacctcc caaagtgctg  11880
ggattacagg catgaaacca gcctagaaat acatactatt atttattctt gttttacaga  11940
```

```
taagcaaagt gagtcatgga gaatttggtt gaaagtccca aggtcaggag tcgtgaagct    12000
gggattaaaa cctaatcatc tgactttaga gagtagacac ttgctccatg catattgcct    12060
ccaattcatt cattcaagca ctccctgctc aagaagttct ttcttatgtt gagctgaaat    12120
ctgcagccct atgcgtttta cccagcagtc ctggtgctgt tccctaaaat cacttagact    12180
gtgcctgctc tttctgtgtt tacagtgtca gctgtaatat ccccctcttc ggcctaacgt    12240
ttctgaagtc ccttgccact gggtctcctc tcctcttcct gtgttctttc taagaacacc    12300
tatacagata ggtgtcttct gtacagggaa gctgttcctg agatccgggc atcgactctg    12360
ttagaataat ctacgtatga gttattttt tgagaactat gtgtcattgc tgactcatat    12420
taactctgtg gttaactaaa atctcaagat ctctttatgt ttgttgagaa acttatttaa    12480
cttctctggc cctccgtttc cttcactgag cagtggagtg attgataacc tccacctgtg    12540
gttgctgaag gtcttgcaca agatgatata gttaaagtag ctagcagtgc ccacgtacgg    12600
cggatgcctc acaacggttt gcagccatct ctctatctgt gtctttgtct ctctctcaca    12660
ctggttttgg cttactgtta gcagctagcc gagataagtg tgtttatggt ctttgcatgc    12720
attgtttctg tagcatactg gaggattaca agaggttggg gagtgagggg gcggtgagga    12780
gtagacaaag gcagccaact cttccaagtt tagcttagaa ggaaggagcg gtaaaccta     12840 gttgaatgtt ggactgaagc aggtttgttt ttgttttgtt taaaggatag ggaagatctg    12900
tgcgtgtttc caggataaag aaaaggagag aatatgatat taaagattct ggaagtggga    12960
gaaggagcaa tgaaatacag acttgaagtc agtggcatgg acagggtcaa gatcacagtt    13020
agaggatgca gccttagaga aaaggaaggg gctcggttct ctgagcaagg agggaaagaa    13080
gagaggcaga tgcagagaag tacggcacat cgtgctgctg gttgtagaaa taacctctga    13140
cttttaataa agtcatccct cggtatccct gggggattag ttctatgacc tccctcggat    13200
gccaaaattc gtggatgctc aagtccctga tataaaatgg catagtattt gcatttaacc    13260
tacacacatc ctccatatcc tttttttttt tttttttttt tttttttttt ttttttgggg    13320
agatggagtc ttgctctgtc gcccctggctg gagtacagtg gctcgatctt ggctcactgc    13380
aagctccgcc tcccgggttc atgccattct cctgcctcag cctacaggtg cctgccacca    13440
tgcccagcta atttttttt tgtatttttt agtagagaca gggtttcacc atgttagcca    13500
ggatggtctc gacacatcct ccatatactt taagtaacct ctagataatc tctagattac    13560
ttgttttgtc tttttttttt ttttttcttt tgagatggag tttcactctt gtcacccagg    13620
ctggagggca atggtgcaat ctcagttcac tgcaacctcc gcctcctggg ttcaagcaat    13680
tctcctgtct cagcctcctg gtagctagga ttacaggccc ctccccaccc cccccccaa     13740 caactggcta attttttgtat ttttagtaga tgggggtgt caccacgttg gcctggctgg    13800
tcttgaactc ctgacctcag gtgatctacc cgcttcagcc tcccaaagtg atgggattat    13860
aggcatgagc cactgtgtgt ggcctagatt acttataata cctgatagaa tgtaaatgct    13920
atgtaaacag ttgttatact gtattgttaa aagacagtaa caagaaaaaa atctgtaca     13980 tgttcagtcc agacaaatgg ttttctgttt ttttttttt tttttaata tttttggtca     14040 gtggttggtt gactccagga atgcagaacc cgcagatata gaaggttgat tatgcgttca    14100
gaggcaggga ataccatctt gggttccaga aagaaaatga tcagcatttt ctgtcatact    14160
ctggtaaaaa cagatctttt gaatggacag gtgtattaaa ccctgtggag ctggctgggc    14220
ctggcggctc acgcctgtaa tcccagcact ttgggaggct gaggcaggtg gatcacgagg    14280
tcaggagttc gagaccagcc tggccaatat ggtgaaaccc caactctact aaaaatacaa    14340
```

```
aaattagccg ggcgtgatga cgcatgcctg tagtcccagc tactcgggag gctgaggcag   14400
aagaatcgct tgaaccctgg aggtggaggt tgcagtgagc cgagatcacg ccactgcact   14460
ccagcctggg caacagagtg agactccgta tctaaaaaaa aaaaacaaaa acctgtggag   14520
ctgatgaaat cctgcaggga gcttcacggt gacagcaaga ggagaaacac atccccatat   14580
gccccgcaga gtttgaagtc ccggctgcac ctctccccag cagcaggttg actctggaaa   14640
gttgcagcgt tcttacctac agagtgggaa cagtactacc cattgcacag agtgggtgca   14700
aagctctgtg acggaataca tggcaagtgc ccaccacatt gcctgggatg aggtgggccc   14760
ttcctttacg taagagaacc ctacagatac actcaaagtg ggcacattcc tacagaagga   14820
gtgttatttg tgtagaaaag aaaaacatga aaggctttta ttcctataca caataaagca   14880
cccctttaat gtcttttttga ggaggataat atgaaattga tgaaaggaa ccctgtggtt   14940 ggatccctga caatcacatg tatcccttt ttcactctta aaaaggagt aaggaataa   15000 aatagaaggg gagaggggc agagagacct tcaccgcccc cccccacccc ccatcatcca   15060
atctatagtc aaaccctcca gactgtgtct ccttggcatc tctgacaccc ccaccgccac   15120
caccccagtc aattcctatc ttatcccct atcctggatc tgattctgct aagttcctgc   15180
cacactaaag acagggtggc tttctgatga caacattcct ctgcttaaac ctgtcagtaa   15240
ttccttgttg ctctcagacg gaactaagtt ctgaatttct tcacacggct ctcagcaagg   15300
tcacagtcac cctgctaggc cccaggggca aatctcaatg gtcatcttct tgaagacctg   15360
gctcagttat ttctttctca ttgaggctca cgaccccacc ttcttgcatg cctcaaacgg   15420 cccctacca tgctcttctt tcgcccatag ctcagcacac cgtatcattt taatttatgt   15480
attttgctta atgtggatga tctgtctcct cctctgctgt cctcaccaga gcatcagttc   15540
ctcaaaccaa ggctctttgt tttgttcttg gatgcaagct aaatgtctgg catgtggcaa   15600
atggtcatag atacatgtca ttgaaagaat gattcatcac ctccctcttt ggccttgtct   15660
gtggttctac caaatcccat tccctcccca gtgccctcca ttccccctcc ttggctgaac   15720
attctgaacc acagacagtt ctttaccctg aacctttgca tattttgttc tcttagctta   15780
gagcggcccc tctccctccg tctgcttggc taatttctac ttgttcttca gatttttatct   15840 tagatgtcat tccctcaagg aatccttctg tgactcaaca tggaattaag ttgcctcctt   15900
tgaccctgaa agcaccatgt actcaatctc atcttggcat gactcacttt gctgtgtgga   15960
atgtctgctt tccttgtttg tctattcctt tagactgtaa gatcctagaa agtggggcc   16020 gtgccttgct catgactgtg tttctaacac caaacacagt gttcagtaga gagcagctgc   16080
tgagtacgtt tctgctaaat gacagttgat ggaggacatt tagggttgct tggaggtcaa   16140
gtcaaggagg catttaacat tctagtaaaa caaggaagta acaggctcct gaacatgccc   16200
acaatgaacc agatgcaaac ctttccctt ggcaggattc tttgcccata agtggagca   16260 cgaaagcagg acccagaatg ggaggagytt ccagaggacc ggaacacttg cctttgagcg   16320
ggtctacact gccaagtgag tcctaamcct gatgttgcta ataagtgggg gcatgggcag   16380
ggrggcctcc ttctaggagt gatgaccacc cttaatacca catgtctgtc tgagccaagy   16440
ttctgagcgc cagggaggtg aggaaggttg gacttcacca gagaggcttt gtggacaccc   16500
tttatcatct tagtgagtgc tagtgtcaaa acaaagggag tggggatatg gggcacattg   16560
gtggagggag gtgtgatctc tgcagcttca gaaagatctg aaagagtcat ttggttagag   16620
aagttgacct atttcctgtg gggttagacc agggttgcta ctgtgaacac cagccatgac   16680
```

```
tcaccagtca ccttcagaag ccacaggcag gacatgctga cgacagcctt caactcaccc   16740
accccttgct cccctgcggg tggaagtctg gaggtgacac cactgcattt tctaacacgg   16800
gggctccttg agcaactaga acaagaacag aaagaatggg gacattagca ggtgctttcc   16860
ccctctctca ttcttttctt tgaataaaaa ggttgtttga aaacacctga gcggctccta   16920
aagatgggtg caatctattc gggatgcaaa tccgaatgaa tgttattcaa atgctcctct   16980
cttctttatg cagagtgtat ttcaaggctc agccagtggc aggcatgctg gggactatgg   17040
actacggact aggggcctgt cacagaggaa ggcctcatgc tagagagcta agggaggagc   17100
tggccttcag ttccatccca ggagcaactt tgatgttccc agagatcctt ccaaagggga   17160
agtcatggtc acccaagaaa aatgtattca gaatgccaag aatggtgcaa actcaggaca   17220
aagattcaca ctgcagggtt ggagtccctg gcttgctgc tggcaccatg ggagggaggg   17280 tcccttcag gggtaccgtt ggtttcctgt gaattaaact ggcttcaagg gatctcgact   17340
gaacaggcct atatcacact cactgatata ctctctcttc agtccttctc ctcatctagg   17400
tatttttaat tgtttcagtg aggtgtaggc atgaggggat tggaggggc atctcctcca   17460 ttgcagtttt tcattggctg ctttgctccc tcagctccga aatcgctggg ccactctcga   17520
acgcattagt acggtagtca caggttgatt gcctggcccc ttgccctctg tgggcatttt   17580
ccctttcaga cagcccctga gtactcacag tgctgctaca gtgggccacc tagatctccc   17640
tctttctcca tgctcccacg tgctctgggc tccactccct tctcccaagc acttctgtcc   17700
agggctattc cagcagtctg acctcaagga aatcctttgc taaactgatt atagagaggt   17760
ttctatttta acatttaggc cttccatgta ttaattctca gaatcaattt aagatgttta   17820
aaggtgtgat ttaagacatt ttaaaaccat ttggaggaga gtacagaaat tatgtcactt   17880
gctgtcagcc tctttgcacc atctgcagag aaagatacta gagtcccgcc ttggacacat   17940
ccacatgcaa gaggtgcaaa gaaggtgtct ttgatgaggc aaggtcaaaa cttctcccca   18000
gacgaaatcc aaagaaagca ttcctactat gctatatcag tttggaaaga aaaacttctg   18060
ccaggtgact gcattctcac tggtcacatt gtgttcctat ggactcctca gctcaaccaa   18120
tttggagaag ttatggtgca atttcaccat atctggttag aagttaagtt tccaatttgc   18180
tggcaatgaa gaagaaatgg agcaggccag gctgtgtagt ttctgccacg tgcccccggg   18240
agtgaacagc tctgtttgta agaagccatg gtgcttagac ctgggctcgc tagttgccag   18300
cctccaaatt gcagaagtgc cctttggttg gtggctatgc tgtgtcactt gggaaggtcg   18360 tttgaagtt ccacagtcgt tgtggggtgc cagagattaa aaagcgtaag aggagagtgg   18420
aaagtgattg ttgctgcttg ggcatcccca ccgtgtgggt gctgcagccc agctctcaaa   18480
acccatgggt ctgtacactc aacctccatg agagggaagg agaaggatga gggaggggag   18540
agatagccat ggaaaggtag gaactaagca ggcagggtgg agagttttct gtaagacaaa   18600
aactgtctgg acactgctgc ggttctgtta caaagaccac ttcctccctg ggccagcaac   18660
atatctgtgt gcctgtctgg gttgtaaaaa gggtcaaaga tcaatgcagc aggcagctac   18720
atgctggaaa agccagaggc agctggtctg tttgcctgtg ccaggaaacc actgggaatg   18780
gggttgtgtg ttattctagg agaaagtcgt cccagcagca gcttctccag gggcatccaa   18840
gagcactgaa aaaggttgca agatgaccca tgaggctgca ggaagaaaag aacatgcatt   18900
taatcttgct atctgaaaag taagacatga agctttcctc attttaata tacacatgga   18960 cagtagtatg tgtatatagt ttatatgcaa atatacttgt tataaggttg catgctcaaa   19020
atttttggtt catggggtgt gggatcataa atgtttaggg accatggcta tcaaggaaaa   19080
```

```
acagcatgaa ggataaatga tactggtgga ttaaaaagac agatgcatgt attttttagca   19140 taaaacacaa ctgctgactg atacagatag ctcaagattc tggggcagct gctgaacaga   19200
tacactagcc agtgtggctc atcggctcag acttggcctt aattaatggg ctgtccctcc   19260
acccatctcc catgagggca gagctgagcc agggtttgag agctaaaagg aattggacct   19320
ggactctgtt cacgtgtata ttttaattct aattaattca ttcttttgaa agacagagtc   19380
acactctgtt gcctaggctg gagtgcagtg gcacgatctt ggctcactgc aacctcggcc   19440
tcccaggttc aagttattct cctgcttcag cctcctgagt agctgggatt ataggcacat   19500
gcccccatgc ctgactaatt tttgtatttt tagtagagac ggggtttcac catgtcaggc   19560
tggtcttgaa ctcctgacct caggttatcc acccgccttg gcccctcaaa gtgttggaat   19620
tacaggtgtg agccaccgtg cctggcctgt tcacatgtat aaaacacagt ttaatgtcct   19680
attcccagcc aatgagcatg ctagagcag ccttggtcaa agtttggttt ttggagaaaa   19740
atccttgtta gctgacctaa gattcctctt tgtgagtgta agtaagcaca ggttgcagag   19800
aggagaaggg tctctggaga ggtgtaattt tctaaatgga ttacaagttc atggactttt   19860
aacaggtgtt acaggggata acaagttctt tatagacaga cttttgagga cgtttaaggg   19920
tattctgatt cttggttttc taagagggga atgtattatt taactacaga caccccacc   19980 gcccacttttt tgcagagtgt atcaaaacat gttttttggaa taccaccctc atgtcgcttc   20040
tccctgcatc tcttatctct tggtgtccat tctagactca ctttctttct gttttttatt   20100 tttattttttt tttgagatgg agcttcactc tgtcaccagg ctggagtgca gtggtgcaat   20160
cttggctgac tgcaacctct gccttccggg cttaagcaat ttttgtgcct cagcctcctg   20220
agtagctggg attacagcat gcaccaccat gtccggctaa tttttgtatc tttagtagag   20280
acagggtttc actatgctgg ccagcctggt ctcaaactcc ttacctcagg tgatctgccc   20340
gcctcggcct cccagagtgc tcagattaca gacgtgagcc actggtgcct ggcctagact   20400
cactttcaag tggcatagac ttgtaaaatt atttaaaggt gataggtcta caatgatcct   20460
gtcaattagt attgacacta ttattaataa actgttatta attatattta cttactttaa   20520
attaatccaa actaattaac ggaacactaa agagtttcta tgttttattc ccagaggtgg   20580 agaaaatga aagggaatat agcaacgaat tcttttctcc ataaaaacat gaatagtgca   20640
gcacatcaag ttgaacatac cacagcaaat tgttgcaaga tctgctgagt agctcctatt   20700
tagacctcaa ggaatgagac tcaaaatggg ttcatcagtt ctgttttgca gaaaaaatag   20760
cgcaaaattt ctcaaaagaa aatccagaat aataataatt tgtcaatagg aaagacattt   20820
ccactggggg ttaagaagga agacattgga acaatgatag ccaccactta ttgaatgctt   20880
actgtgagcc aggtggcact tcaccttgtt tcattctcac aacagtctag ggaagtaatt   20940
actaatgtct ccatccacct cttgtagatg agcaaattga ggctcattga ggctaggaaa   21000
tgcacccaca ctcacatagc ccataagagg cagccatggc attgggccca gaccatgtga   21060
acttcaaaga ctacacgagc agccactggg cagctgtcat ggctaaagcc acttgaattc   21120
agcccagcag caacccctc tccaggaggg gcacataagc ttgcagcttt gggtagaagc   21180
tgcacttgaa gtcctggatg gcgagaggga ctggcttgag ccagagccag gaacaaggct   21240
ctgagaatat tctggaaatc cacaggagga acccatttc ttacagctgg gagaatttca   21300
ttcaactcca ggctgaccat gttttattag gaacgaaggt gacttgaact aatagtcagg   21360
aatggttgaa tacggaccca atgtcaaatc actaggcagt tcacatttct aatgagcaaa   21420
```

```
tcccttagac aattaagaat ttttttcctt ttgcataacc cagacaaaat cgctacttaa   21480
aaacaaacca aagacccgaa acatgagaaa gagaaggaag caggggaaat ctttggtact   21540
aataagtttt taaacaataa gagcaccaga tattttaccc catcagacac agaatgttat   21600
tcgaataacc aaaaaaggaa ttttttctct aagtttcttg aactgaaaaa tgaatcatat   21660
tttctcagtc ctgaggctgc aattttgtgc ctctagtaac atataagaat agatgtgatg   21720
ccagtgccca gtagctgctg caattgttac ttggggacct gtttattcac taagcacttc   21780
accccagtga taaatttgta ggggcctcct gcccttttgga gctcctaccg tgtccattag   21840
atcagtggaa attctgggat tcagagcact ttgcaaggtc agcaggggtc tgctctttct   21900
gtcctgttcc tggtttttgg ttgtgcctgg attccagggt aggtttctca tctgttacct   21960
tcatagactt ctccagaaaa ggatcttttg accatcagag gaccacgaag attccattgg   22020
tgaggcgcag ataacctgat ctctctgggt tctctgcagg gcacagatga agggctggcc   22080
attcccaagt tctcagtggt accactgagg catgagaccc taatggtttg catgagcagt   22140
ttgaaaattg catctttgtt tttacctata taatcacatg aaaccgtgg  ttctcaaacg   22200
tcagcaggca tcagcatcac atggagggct tgttaaaaca gatttctggg ccccaacaca   22260
gagttttaaa ttctgaaggc ctgaggtggg tgtgaacatt tgcatttcta acatgttctc   22320
gatgctgctg ccgcctctgg tcccgagagc atgcctggag aactgccacc ttcgaccatg   22380
gactgtgaga attcacatgg acctcagaat tataatcagt ctctcagttt tacagataag   22440
gaaactaaat ccagagagat tgttttgcca atggtgaaca gctggttaaa gtcaggatgg   22500
agactttaat cctagtcaag tgacctttcc tctgtattta tttccctccc tttttatgcc   22560
tctcaagtct agttacactg ttttttcatgg atgggcatat ttattgtcct gatctggact   22620
gcagacttct caggaggaca cctatgattt aatttagtat agttgaagag ttaacagaca   22680
tggctttgga gacagactga ttatggtgtg aatcccggct ttgccactcc ctagctggat   22740
gaccctgagc aagttattca gcttctccaa gcctgagttc cttattggaa acatgagagc   22800
aattgtgata ggcagaataa tggccccctc accaatcatg cccacatcct aatcctagga   22860
acctgtgaat atgttatgtt acatggcaag gggaaattca ggcagctagc cagttggcct   22920
taaaataaag agattatcct ggatgatctg ggtaggacct gatgtaacca caagggtctt   22980
tttaatgtgg aagaaggagg cataagagta gatgtcagag tcattcaaaa taagaaagat   23040
ttgatgggcc atccctgact ttcaggttgg aaggaggttc tgagtcaagg aatacaggtg   23100
acctctagaa gctggagaag gcaaggaaat ggtttctccc ctagaagttc cagaaggatt   23160
gcagccctgc taatatcttg actttatagc cctttgagat ttattttgga tttctgacat   23220
cctgaaccat agtaaaaggg tgttttttgt ttttttgaga cagagtcttg ctctgttgcc   23280
tgggctggag tgcagtggtg tgatcttggc tcgctgcaac ctccgcctcc caggttcaag   23340
tgattctcct gcctcagcct cctgagtagc tgggattaca ggtgcttgcc accacacctg   23400
gctattttt  gtgttttttag tagagacagg gtttcaccat gttggccagg ctggtcttga   23460
actcctgacc ttgtgatctg cctgcctcag cctcccaaat tgctgggatt acaaggcgtg   23520
ttgttttaag ccactcagtt tgtggccact tgttacagca gcaagaggaa actcatacag   23580
ttatcatgtg aactcacagg aatatggtga gttaaaaaga gaggaagggt gcaaaacatc   23640
cacggtagag tgagaactct ccagggagtg aggactgtgc ccagcataca gtgatcaccc   23700
tcttagtaag ctaagtttct gagcaccagc ttttttgagt tgactttgtt gtcttttaaca   23760
tttgaagatc acccttcttt gctcagcctg gcttgcagac ctgggctgat ttgtggatct   23820
```

```
gatagaaaag tttccttagt tgggctcttc tccccgacca cccccatgcc agtgtggcca   23880
catcctctgt ctgcattgct cactcttcaa ttccaagaag cgcagggca ccgccaggaa    23940
caggaaccct gccagaggaa tacatcaaga aaccaagtct cccttacgca tcaccgtagg   24000
aacagagtta atggattatg aacatgtgtt tgctttatac cattgtttgt ttcccaggtg   24060
gcagctggct gccccatctt attgggtaga tgtaagtgga attacgaatg ggatttatgt   24120
ttcatgcacg atggtgatta ttaacttcaa cttttcaggta attttcagac cacattgcac   24180
taacttggtc tctgattgtt tttctccttg tttgtttatt ctgcagccag aactgtgtag   24240
atgcgtaccc cactttcctc gctgtgctct ggtctgcggg gctactttgc agccaaggta   24300
actcagactt ccctttgttc attctccttc tataaagtgc atctcaagga ggttcaaagg   24360
kcaggctttt tgttgaaagg actttgcctg acctctggct cccatctgtg aagccctgga   24420
gaggtgagag ccctcgggag gccgtgtttc aggcatgctc tgcacccgtg cagagcgcgt   24480
gtgataatgc attgctaatg cttgctccct ggtggctggc tgagagctgc tgtgctgaca   24540
agggtggttt aaggctaaat gtgactcaga atccttaagc agtgttagtt cagatacaag   24600
ggcattataa atgagagtgc ctgagggatc tattttggga ccgctgtcac ttggctcttc   24660
tgctaataag cttccagtgt ggtggccctc cttcaggcat gtttccactg agccacgggc   24720
tggatgccac atccccggcc ttcccacagt tatcagcagc ccacaggctt gacttgagca   24780
agttggaaag acaaatcaac ttccagagtt gatttaacat tgagtggaaa tcagtcatac   24840
ttttggtccc ctttcggggc cacgcctggc actgtgcctg gtggcagatc ggcatgaact   24900
ggccagcttc tgtggccctg gagggcacag gcagaaaggc cacgctcagt cccatgatga   24960
actgtttaag acttattgtt gtctccccgc tctgtaaagt agatagagtg gatttttatgt   25020
cccttattac ctttcaggat actttgactc agggagataa agtaacttgg gtacagctac   25080
tcagctggtg aagaacacag gcagaatgag tgcctgggtc ttttgactta aaattctgga   25140
tttttcacaa agatcctctt actttattca tttacataat aaatatatat tgaagagcta   25200
ctctgtgcca agccctgtgc ctagatatac agtgataaat aaagagtagc ttctagaggt   25260
cacctggcgg tgaggcacag gccagctggc aagatggacc acagaagtca gtgaatgaag   25320
acaatgacaa gggtgggaag cgccatatgg gaagagaacc aagttcagtg atagagagca   25380
gaggtgaggc ggcagcagaa accacttaag ggacaccacg tggcactcct tctgtgctga   25440
gaaggctgtc agtaagctca ccatttattt cctattttct ctcctgagtt aaataggaaa   25500
catgtctcgc attacttgaa aaatcaagtc aaactatgct cttactagga gttatggtcc   25560
tttttatgtc ttagatgatg cttgatctag atgaatgcgg acttgctgta gctagataaa   25620
tacaatggga gtttgaaggt gtttcgtagc cctggaaata tgtatttcct gtcaaaacaa   25680
gctttgtcat tgccagcaga caaaagcatc agtaacttg gttgataatc gtcatttctt   25740
aggaataaag tagactgtag aatttttttt agcagaaagg aaacccaaag ataattctag   25800
tgcaaatccc tcactttata gagcagaagc tcaagtccca gaggaacaag tggcttgaac   25860
gaacatcaga attttagggg ctggatttgt accctcctgg tgccagcagc ccacttccct   25920
gcaggaggca ctcaccttcc ttgcacaggg gtatgagtgt ggccattttc cacccataat   25980
ctctgttagc tcatgttcaa ttgggttccc attgaaagaa aaatggacca gtaagttgga   26040
gcagaatcat tcagatggta taacataagg aaaaactttg cccaaggcaa atcgtgattg   26100
tgacagcttt gtgattttta gagaatagca tgggccaggc acagtggctc atgcctgtaa   26160
```

```
tcccagcact ttgggaggcc gaggcaggca ggtcacttga ggttgggagt tcgacaacag   26220
cctgaccaac atggagaaac cctgtctcta ctaaaaatac aaaattagct gggcgtggtg   26280
gtgcatgcct gtaatgccag ctactcggga ggctgaggca ggagaatcac ttaaacctgg   26340
gaggcggagg ttgcggtgaa ccaagatagc accattgcac tccagcctgg gcaacaagag   26400
tgaaactccg tctcaaaaag agagagaaag ctgaagttca cagtttctct tttgctttga   26460
ttttcttatc tgccggataa caatagtatt ttggaaggca ggaggaattg tggaaagaaa   26520
tgggttttgg ggagtggctg attggaggca aatccaagga cactcattgc tggtgtgtga   26580
ctccaggcag ttactcagct tttccaagcc tcagtttcct tattgtaaaa caggaccatg   26640
gtctagctag tagcattcct atggtgagtg aaataatatg tataaagctc ctgacacagt   26700
gcttggcata tatcagattg agccatgtaa aactgccaat atctggctat ttatgaccta   26760
caaaaatagc atttcatatg attccaccta acatctgaag cgcaataaat gttattattg   26820
ataatgcagg tggtggtgat aaagttttga aatcagaaag acctggcttc aaattccacg   26880
ccttcactgg cctgacttat tttcattcat ttgacaaata ttattttgaa cacccctatg   26940
tgccaggcac tatgccaggc tcagagatga tctaggaaaa agacagatgt cctcatctgt   27000
cttaggctct tgtggcctaa gcctaaattt cctcgtctgt caaatggtga cagtaacaca   27060
ctccttacca gagagctggg aggattggag actcaagttc ccaaaacgcc aggagcactg   27120
cggcaggtga aaagtattcc ctcaatggcg gaagtgttta aattgctttt atatctgtag   27180
ctctagataa cactagttcc agcttagtta actcccagct ccaagccttc aggacttcat   27240
agagttattg gggtgctgct cttggcagtt tcccaaaaag ctagaatgca gagggaatct   27300
ccttcccaaa aagctagaat gcagagggaa tctccttccc aaaaggctag aacgcagagg   27360
gaatctcctt cccaaaaggc tagaatgcag agggaatctc cttcccaaaa ggctagaatg   27420
cagagggaat gtccttctct tctaaatggt agctgttagt tcaagaaagg ttaaacattg   27480
tgctgtgggg aggctcaggg gtgaagggtg tacttttaag agaaccagtt tcagagctgg   27540
gtttggggtt taagccctac cctctgcccc ctttttacgag ctgacagcct tatgcaagcc   27600
tggttgacca cctgaaccca cgtttccaca tctggaaata gaaatgtggg tactagttat   27660
gttgaaagga ctcaggttag atgatagata tgcaaatacc ttggaaacca ggagtgtcca   27720
gtcttttggg ttccctgagc cacactggaa gaagagttgt cttgggccac acatagaata   27780
cactaacccct atcaatagct gatgagctaa agaaaaaacg ttgcaaaaaa aatctcatat   27840
ttttaagaaa gtttatgaat ttgtgttggg ctgtattcaa agccatcctg ggccacgtgc   27900
gacccgcagg ctccgggttg gacaagtttg ttgtaaacaa tgccatgatg ccggcataag   27960
gtcgttacca gtattaggaa ggttctcagg tttcctctag cccttgggct cttttcctga   28020
agtgcgtgtg tcttctgcta gatttttgtga ccaatgttga ttgcctaatt gggctaacag   28080
catgttttg tggctacgaa actgacacag gtgttttcat ttctccactt agttcctgct   28140
gcgtttgctg gactgatgta cttgtttgtg aggcaaaagt actttgtcgg ttacctagga   28200
gagagaacgc agaggtaggt aactgggact actaaagaac tgtggagcga ttcctgattt   28260
ttgagcagga agagtgacaa ttcaaaacag tatttgacta gattcacggc tccgtagcat   28320
ccccttgggt gggagsggga aggctgacta ggacctctga ttcttctytc cctgagcttt   28380
gaaggctctg aaaatacagc tgggggact tgcccagttt tcttattaag caattcctcc   28440
gcatggtgct ggctttcaaa gggtgcttca gtgctgtttg ctgcacgtgc cttgcagccc   28500
cacaccctgc actcccgccc tgcagagtct ggcgctggaa tgacatttta ggtctgggtt   28560
```

```
cccaggcctc ctgagagtga aatgtttcat tgtttgtcta gagaaatgag aactaaagct    28620
tgcaccttgt gataagttgt cctgaggaac atatctttca gggaccagaa gaaagaatgt    28680
tgggaaaata agatgcagta agatgcagac atgacagcag ggtgcagcgg ctcacgccta    28740
taatcccagc actttgggag gctgaggtgg gtggatcacc tgaggtcagg agtttgagac    28800
cagcctggcc aacatggtga aacccgtctc tactaaaaa atatacaaaa cattagccag    28860
gcatggtggt gggcgcctgt aatcccagct actccatagg ctgaggctgg agaatcgctt    28920
gaacccagga ggcagaggtt gcagtgagcc gagattgcgc cactgcactc cagcctgggc    28980
aacaaaagca aaactccatc tcaaaaaaaa aaaaaaaaa aaagattca gacacgagac    29040 tgtgaaactg actagcatca ccattgcatt gtttatagat gttgccagac agaaagcccc    29100
aaagcagcac agtaccttcc tgacatctgg actaggaaat ctagatttta gtaaaataca    29160
tgctaatact tacagaagaa atgtcggcgt tagagtatgc cgtcagttcc ttagagattg    29220
caattcctaa tgcactagta tggtttcagg tgccaggaac acgttctgtg aggctgctgc    29280
cccaggtgct gaccccagcc ttccacacca ttttccttcc ttgtgttcac agccgctctg    29340
tcttttacaa tagcacccct ctctagtggc taatgggctc tatgattaga tagcatcctt    29400
cagtagtgat aaaggcagtg acatcctagg gaggtcagcg ggtgaaagcg ctatatctgg    29460
aaaacctgag agcctgtgaa gctcaaggac ttgacggggt tagaccgtga gccgggctgc    29520
agctggaaaa agaatgactg ttctttcagc agatccttcc ctgtgccatc tctttcttca    29580
ttcctctcta gtggcattct tatttatcct ctaaaaccac aattccatta tctctcctat    29640
tcttatcaac actgccctaa atgatattct ttattctctt ttgccctgga aaacctctat    29700
catgcctttt cccatgtgat tacctcgtta agagtggggg tggaatgtct agcaatgaaa    29760
taagagggtc ttctcttttg cctggctccc tatgcagccc tatcttaccc cctgcaaagt    29820
cccagggatg tggctcagtc actgctcctc tcttcatctg tcaccacttg cttgagatcc    29880
tacagctgct ttaattccga gaccatctgc agaacatgac aaaatttgtc cacctaccca    29940
catgtccttt taactttaaa ggctttacta actgattcct attagggaat gaacagaggt    30000
ggcaaaaata acaatagga gattgattta caagaaatct ttaaaatagt agatttcttc    30060
ggacctcatt gaaatataaa tggcctgcct tcttgtgtcc ctccctggtc tccctcttta    30120
ggtgataaga agaagatcct gccagcccca taacccgcca tctgcgcggg ttctagaccc    30180
ccttctcctc ccctctggcc gtggtaggca ttactgatga atcatggtgc tctttcttcc    30240
agagaccaaa cctggcctcg gaatccttct taacacagat actgcttaac acaaccactc    30300
tgagcagctg tcataagtag aagtaataga tactagaaga aatgtctaag cctaatctag    30360
accaaaatac ggcctgatat agatgcaagc cagaggggct ttatggttaa atgcaaggag    30420
attttcaacc ctgccgtcta gaagctactt gctgagatct tcttcagttg ggcccatctc    30480
ctccccaggc ctctcttctg ttcctgggct atgtcacact tggactctgc agacacctaa    30540
tgctcttggg acctgcttta gttcttgacc tcaccaaccg aggaggaatt gctcgatgag    30600
atccttcccc cggaatttct ctcttgaacc ccagatggtc cgttgcccct ttccagaagt    30660
tgctccagcc ctgtccgctt aggaagttca gtgtcatcct tgatccagtg ggtagggaag    30720
acattccata atgtatgccc cagtctgagc ttcttccttc aggcttcagg ctgccctgcg    30780
aggattttgc agctcccttt ttaatgccct ctagaagttt ctggctctta ttttcagccc    30840
ttcatcctac tctctctgac cccttcctct atcctgttta gttcacctgt agcagttact    30900
```

```
acccagcagt gaaggatgaa tcttggtttc gtttcttttc tcttcttttc ttttttctct   30960
tctcttttcc ccttcccttc ccttccctcc cttcacatca cctcatctca cctcaccttg   31020
catagtcttg ctctgtcacc caaactggag tgcagtggcc tgatcttggc tcactgcaac   31080
ctccacctct tcccaggttc aagtgattct tatacctcag cctcttgagt agctgagact   31140
acaggtgtgc actaccacac ccagctaatt ttttgtattt ttagtagaga tagggtttag   31200
ctatgttggc caggctggtc tcgaactgct gaactcaagc aatctgccat ccccggcctc   31260
ccaaagtact gggagtatag gcataagcca cccatgatgc ccagcctgaa tcttggtttc   31320
ttccccattc atttaagcta ttacctgggc ctgaactcaa tggcacctgg caccaactgg   31380
caactgactc ttggtctttt attacctacc ttccctagca ggcactgggt tgctccctct   31440
tcctatccca tggagtcctg tcctctgttg gggctcctac tgatcctctt ggcaatatga   31500
agttctcagc tcaatggtgg gtgggcaatg actgccaact cttgaggcca atgaactcag   31560
gtttccccac tcctcctcct cctgagttgc tcactcactc ctcattcact caacattgat   31620
tcagtagata tttgctacct gctctgtgcc aggtaccagg tcagttgctg aaggagtaac   31680
agtgaacatg acggagtctt tgtccccaag gagacccaag gtgtctccta gagccagggg   31740
cacattgcaa gaccaaatat attcaactta ccaaaataat catagaccta gttctcaaaa   31800
agcaagaaga ctgattcctc gttgtcattt ctcctcctca gcatcaatgt tttagagtct   31860
gtgggcccct ccaagtgtgg agtatggtgt tacttcacca gagtttgagg agaaacattc   31920
ttcttttgga aggccgggga gcatagatgg atatcaaggc tgctgtttct aaaagcgaaa   31980
cccaccaaac aacagtatta gaatcatctg tggtgcttat taaagataca gattcctggg   32040
ccccatccca gacttatgaa tcagaatctc tgccagagaa agcctgagaa tttgcattct   32100
cagatgattc tgcattctca gataacacat tctttaggtg attcttacac acactggagt   32160
ttgggaatcg ctgaaggctg ttcacttctc tttctgaga aatgattcat tcatttcaga   32220
aatatttgca gaggtcctta tttattggag atttgtgggt gggcagagga gaaatatctt   32280
gtcctcacag agcttacaat ttttattttc tttagaggtc accaggctta aaatgacact   32340
tccctaaatt ctgaaaagaa cagatttta aaacaagaag ggactgtaat gttttctgtt   32400
cctacctcgt attttgttca cattaagaac ctggggtggg aagtggagga gggggggtga   32460
ctggcggggg gccacagaga gctgagctgg ggtggtctcg aactcctgaa ctcaagcaat   32520
ctgccagcct cagtctccca aagtgctggg attataggca tgagccaccc acgatgcctg   32580
ggtggaactc agggctctgg atgcctgggc gcccccatct cccacactac ggcgcctcat   32640
cctagaagtg gttagcacct ttgagatggg aattatttag caggatgctt ttgtgttttc   32700
atgtaagttt tatgctgcct gtggagggca cagctgtttc aaaaataata accaaatcct   32760
ggtctccgaa gtctgaaggc atcctttgcc ctgcagtgca aagcacggga ttctggcctc   32820
acacaggcag gtctgaactc ctgtgttgcc tcttgctggc tgtgggacct gaggcaaatc   32880
atgcaacctc tcttttctgt ttgcctagat ggaaaatagg tttacaatac gcccccatag   32940
gatggctgtg agaattaaag gaagtcatgg gtgtacaata cctggccccg aaagatgctt   33000
aataatttaa ttctgacctt cctcactcat ttaggattat gtaccaactt ttagaaacaa   33060
tgaaagatta gtgagtcttc tgtggttggt ataaaaaaaa aatagaaaca tgaaagagat   33120
gtcctccttg ttcaagggct aatgaccctg gtgtgcgctg tctaggcccc caaggtcttc   33180
cttccctgct cacagcattt caggttctcc gcagctttgc tgagcctggg tcaggttcgg   33240
tatctgccca ccatgctcac ctgccacagc tgtggcccca tttccaaact tcagagactt   33300
```

```
aaaggtgcag ctaatgatgt gcccggcctg gggtcacatt ccctgagccc tgcagacaag    33360
ggagcaggag gctgagctct tatcttccac accctgtgca cagcctggga agagttaaag    33420
caccctagtc ctatgctgcg agggccacat gccctgagac cttggaaaaa atcctacctg    33480
aattgaagag catcactatt tcatcaggag gcgctgccat ttcattttc acttcggttt     33540 tatcttgagt gtaaaacagc ttcgcaaatc acttttctt gtttctgtaa tgagcatatg     33600
gtggcctcat tcgtgtgata aatctgagcc accacgatat ttgacttttc acaatttaat    33660
ttatctgaac cctctattct ctggctaaaa aatatccctt acttggactt ctttatttta    33720
ttttcaattc ccttaccagc actagcaggg gactctgtac tcatctgctg gcgctgccat    33780
aacaaagcac tgcagcctgg ggggctcaaa ccacagaatt tattctctca cagtcctaga    33840
ggctagaagt ccaagatcaa agtgtgggca gggtcggttt ctcctgcagc ctctctcctt    33900
ggcttataga gtgccacctt ctacctgtgt cttcacatca tcacctcact gagcatgtct    33960
gtgtccaaat ctcccttct tataagaccc cagtcatact ggatgaggat ccacccatat     34020
gagttcattt taccttaatt atctctttaa acaccctgtc tccaaataca gtcccattct    34080
gaggaactga gagtaaagat tcaacatatg aattttggaa gggacctaat tcagcccaca    34140
acaccctctt ttgggatgtt tattttcccc cttaaggagc tagttaggat gtcttatctc    34200
atgaacatga ctgtgaacag gaaaacaggg agagaatgaa gctggccaag gaacagggct    34260
ggtgtcagct agcagtgctt ttctgatgtg agtgggtccc acaggagct tgttaaaatg     34320 cagattctga ttcattaggt tccagaggga cctgagattt cccatttctg acaagtttcc    34380
agtgtggggg ctgatgctgc tggtccacgg accatacttt gagtagcaag gagcttgata    34440
cataatggct gagtgacttt cagactcctg ctgtagaaaa attatgagtt ggctgggcgt    34500
ggtggctcac gcctgtaatc ccagcacttt gggaggccga ggtgggcaga tcacctgagg    34560
tcaggagttc gagaccagcc tggccaacat ggtgaaacac catctctacc aaaaatacaa    34620
aaattagcca ggtgtggtgg caggtgcctg taatcccagc tactcaggag gctgaggcag    34680
gagaatcgct tgaacccggg aggcagaggt tgcagtgatc tgagatcgtg ccactgcact    34740
ccagctgggc aatagagctt gactcagtct caaaaaaaa aaagaaaag aaaaagaaaa      34800 attatgagtt atattatcag catatggggt gcctttcaaa ttgataaaat ttctaatatt    34860
aaacctgtgg atgccaaatg ctgctctctg attatggcag gaaacggcac ttggcagtac    34920
gaagttagct gttgggctga gctggctcat cttgttgtgc ggtcctgatt gcctaaagat    34980
gccttcccag gatctttact aacaatcctc ctgagtcatt tggactttcc caacctgtta    35040
tcacctctca gatgggccag ccatggaggc agtcagagga gggctctgca gagggagggc    35100
agaaacaggg tggcctctgc atgccattag gaggtcacat ctcactgggg gatgcagttt    35160
aggatttagt gccttggaga gaaggataga gtgtattaaa acatgtctcc gctaggcatg    35220
gtggtttacg cctataatcc cagcactttg ggaggccgag gtgagtggat tgcctgagct    35280
caggagttca agaccagcct ggctaacatg acgaaacctc atctctacta aaatacaaaa    35340
agttagctgg gagtggtggc gtgcgcctgt agttgcagct acttgggagg ctgaggcatg    35400
agaatcactt aagcccagaa gactgaggtt gcagtgagcc gagattgcac cactgcactc    35460
cagcttgggc tacagagtga gactctatct caaaaacaaa gaaacaaaca acaacaataa    35520
caacaaaaac caagtctctc cctccactca aaaatgcaag gcctgtctc ccattgctgg     35580 gtgcccaggt ctcatgaatg tagacatgaa ttattccagt cagcctcagg agaatagaat    35640
```

```
gagccctcag atgccgaagc acctttcaga ttccaccggt tttatcggct catttaaact   35700
tcacttctaa cacagtcctg cattacacac gtgtctgtcg ttatgggcag ctgcagagag   35760
ggtcttaatg gtcctaatgc tcagtgagga tgcccaatgg tcaacagaac ctgccatctt   35820
caggccatca aggagctctg gagttaagga aatcatgaga gcacagaggg gcgggtacag   35880
cagagccctc gtggtaatgg gttttgaggt ctaggctctc ttcgcttggg tttgaaataa   35940
gttcaatgac tagtaatagc tgagacactt ctacccttca aatgaagtaa atgggaaaat   36000
ggagcattgt tgagtccagg gagctataat ttaaacccca tatatctaaa aggggtaaca   36060
tttttgtgtg tgtgaaattg gtgtcattcg cactgcatct acagttttct ttttccttct   36120
cttccagcac ccctggctac atatttggga aacgcatcat actcttcctg ttcctcatgt   36180
ccrttgctgg catattcaac tattacctca tcttcttttt cggaagtgac tttgaaaact   36240
acataaagac gatctccacc accatctccc ctctacttct cattccctaa ctctctgctg   36300
aatatggggt tggtgttctc atctaatcaa tacctacaag tcatcataat tcagctcttg   36360
agagcattct gctcttcttt agatggctgt aaatctattg gccatctggg cttcacagct   36420
tgagttaacc ttgcttttcc gggaacaaaa tgatgtcatg tcagctccgc cccttgaaca   36480
tgaccgtggc cccaaatttg ctattcccrt gcattttgtt tgtttcttca cttatcctgt   36540
tctctgaaga tgttttgtga ccaggtttgt gttttcttaa aataaaatgc agagacatgt   36600
tttaagctga tagttgaggg gttttgttaa tggcttttgg gggatttatc tctataccca   36660
caaacgacta gtttgttttc ctcaaactaa atgataatat taaaaataca catcctggcc   36720
aggtgtggtg gctcatacct gtaatcccag cactttggga ggccgaggca ggtggatcac   36780
ttgaggtcag gaattaagac cagcctggcc aatatggtga aagcctgtct gtactaaaaa   36840
tacaaaaatt agccaggtat gctggtggat gcttataatc ccagctactt gggaggttga   36900
ggcaggagaa ttgcttgaac ccgggaggta gaggttgcag tgagccaaga tcatgccact   36960
gcactccagc ttgggcaaca gagtgagact ccatctcaaa ttaaaaaaaa tacacatctg   37020
gcttctggaa aaattacttg aagatctttt atgacatcca tccctcttca cacagccatg   37080
tgaattaggt tggtatcttc atatactagc atcgtgccca gcacttccat gttatacagt   37140
ttaaaaggtt ctgtaattcc ctgtgggaac ctaagataat gcgaggaccg tcatcgtgc    37200 ccccaaatat tggcaaacca atgaataaat gaatgaatga gtttatgaat cgctaactgg   37260
ctgtatttaa tgaagtatgt gtgttgagcc atttcccaca gtgtggacag atttgtccca   37320
caatatgggc ctcttcccaa aggccctacc acctaatgcc atcacactgg ggatttgatt   37380
tcaacatgtg aatttgggga gagtgcaaac actcagacca tagcaccatc tcagtaaatg   37440
tcccactggt cactcagttc atagtgacag tgatccagcc actgtcatga caggtgccac   37500
ttggcagaaa cagcacagct tggaagatgg cggggtgtag tcaagattcc aggatcccca   37560
acagagaagc cagctcttat aggggagcca ttcatcagga ttgaactctc aatcgagctg   37620
gacagtaata ggtgggtctg tgttattccc caggtgagta tcatgacagt cacaatccta   37680
ggaaggatgt gaagcctccc ccagctctcc tccagttgcc tgcttgggca gcagagatga   37740
tggaatgtgg agtctggcgt ggtctgaggc ctgaatccat gtgcctcatg tatgatgctc   37800
aggcaagagg atctctcaat tcaagggaga gggcctgaat gagccttgct ttccaggcct   37860
gtctgatggt ccaggctgaa gcccctcctg gcttgcactg ccagacctca tccagcagga   37920
gctccttggc attgactgct tcaggatagt tgcttctgct ctgagtgctc tctaaagagc   37980
agtgctctac catccaagct gggcttttct tttcttcttg ctgataggga aggcatggga   38040
```

```
cattgcagga tggaagtggc ccccaggcct tctcatgcct gggcttggtt tggaaggtgg   38100
tcaggtgatc aataatcctg attggcctgg cattgaggag ttttcctggg atgtggtcct   38160
ttcggttttt taaaaattat ttttattgat acacatattt gtaggtattt gtggggtgca   38220
tgtgatactt tattatgtgt gtggattgtg taatgatgaa gtcagggcat ttagggtctt   38280
catcaccttg attatcattt ctatgtgttg agaacatttc aagttctcag ttccagctat   38340
ttttgaaata gacagtccat tttgttagct acagtcaccc aacccggctg tcagacattg   38400
gaacttactc ctattgaact gtgtatttgt acccattcac caaactctct ttgggctttc   38460
agttttacaa ctgggatgat cctgggaaaa ctaaagtaaa tcagacaccc gacgtgtgag   38520
ctaggttata atatgcccag tggaccctgg ggacatctta gctttcagag gtcatgctgt   38580
ccaagctgac tgtggggctt ccagaaggtg gggagaggaa atgatgcaat ggcccatcag   38640
aggcactact tggggcctgg ggccagagtg catgtctaag scattaaggg gagggagag   38700 cagccttcat aattatgaag aggagtctca ggtgcacagc ttctgatgag ggacagcttc   38760
taattgaaga cagcattgtg taatgctcaa actccctgtc ttcagagtgc ctgctgtatc   38820
ccaccatcag ttctgtgact tctccctaag cctcaatttt gcatgtgtta cattgggata   38880
ataatagtgc caaactcatg gggttgtgag gaataatgag gtaaagcaat tgaaaaggtt   38940
tagcacaata taagtgctca ataaaagcca ttattattat tttattacac tagttttcaa   39000
ttcctgcata gcaaattctt gcaaatgtag ggactcaaaa caatataaat ttattatctg   39060 acagttttc tgggtcagag gtcttactag gctgtaatca gagggcaacc aaagctgtga   39120
tctcagctga agctcaggat tctcttccaa gctcactggt tgttggcaga attcagttct   39180
ttccagttgg aagactaaag cctacagtct tcagtctcta gaagcctttt ctctggcaca   39240
ggtttctcta caacatggcc atttatgtct ttaaggccaa taggagaaca tgattagcat   39300
atttttttta agtgaacttt agacccttt ttaaaggcct atctgattag gccaggccca   39360
agtgagcttt aagtcaactg attagagatc ttaattacat ctgcaaagtc ccttcatgtt   39420
taccgtataa cataacttag tgaaaggagt gaaattgcaa ccaggttctg cctgcactcc   39480
acggaagggg attctgcaga agtgtgggtc acgggggggt tattttggga ttctgcctac   39540
gtcactgagt caaagaagc tgaatggttg tgatgctgag gtttttgggc agcagcagtg   39600
tgtgtgtgtg agtgaattca tacgtatgac cacctgggaa gaaaggaggc tgtggtttcc   39660
tccacctcct ggcagacaga gaaatttctt tttttttttg agacagggtc tggctctgtt   39720
acccaggctg gagtgcagtg gcttgatctc tgctcactgg ctcactgcag cctctgcctc   39780
ccaggttcaa gtaattcttg tgcctcaact ccaagtagct gggattacag acacacactg   39840
ccacgcctgg ctaattttg tattttagt agagacgagg ttttgccatg ttggccaggc   39900
tggtcttgaa ctcctgacct caagtgatcc gcccacctca gcctcccaaa gtgctgggat   39960
tacagacgtg agccaccatt aaccattttt ctatctcctg tgggaagggg cacagtgaaa   40020
gaacagatga agctgagaca tacaagtgaa ctcctccctc ctctccattt agactaaaat   40080
aggattattc atactgagat tctccctggt tgcaaagaga taatctgtgc aactgggttt   40140
ttacaattat ccctacccta tgctttcctc atctgtcttc ctcgtagtca gctcaggctg   40200
ctataacaaa acaccataac tgggggcttt tgaacaacaa aactttactt ctcacagttc   40260
tagaggctgg aaatccaaga tcaagtttct ggcagattcg gtgtctaatg aggtcctgct   40320
ttccagttta tagacagtgc cttatcgcta ccgccttaca cagtggaagg agaggacgag   40380
```

```
aagctccttg ggcttttttt tgtttctttc tttctctctc tctctctttt tttttttttt    40440
aataaggtca ctatcttagt ccatttttgtg ttgctaaaag gaacatctga ggttgagtaa    40500
tttattttat tttaaaaagt ggccaggcat ggaggcttat cctgtaaccc taatcctttta   40560 ggaggccaaa acagcaggat tgtttgaggc caggagttca agaccagcct aggcaagata    40620
gtgagacccc atctacccca tctctactaa aattttaaaa aattagctgt gtgttgtaaa    40680
gtgtgcttgt agtcccggcc acttgagagg ctgaggtggg tggagttcaa ggctgcagtg    40740
agatatgatt gagccactgc actccaaccc gggtaacggg gcaagacctt gtctctattt    40800
aaaaaaaaaa aatctttatg tggctcacta ttctgggtgg ctggaaagtt caagattggg    40860
catctgcatc tggtgacagc ctcatgtcgc ttccagtcat gggggaagac gaaggagagc    40920
tggcacgtgc agatatcacg tgttgagggc agaagcgaga gagagagggg agagatgcca    40980
ggctcttttt aacaaccagc actggggaaa ctaatagagt gagagctcac tgactcctga    41040
gggaggacat taatctattg atgagcgacc tgcctccatg acccaaacac ctccaacgat    41100
accccacctc caacactgcc acactaggga ttaactttca acttgagatt tagagggggg    41160
aaacttacaa actatcgcag gcactaatac cactcatgag ggctccacct tcatgaccta    41220
atcacttcct aaaggcctta cctcttaatc tcatcacatt gaggattcga tttcaacttg    41280
aattttgggg ggacaccaac attcaggcca tagcatcatc tcaataactg tcccattggt    41340
ggtcactcag gccccaaaca aaggaacctt cctccattcc tttccgccct cccacccaca    41400
gtcaatcatc cccaagctcc atcagctcca cctttaacgg ccaacccacc tctgccacat    41460
ctcaccatct ccactgctat ccctgtcacc tgggcccacc attctctctc ctggacagtc    41520
tccatagcca cctctgtcag atttatttta tttttttatt ttttttttg agacaggttc      41580 ctgctctgtt gcccagactg gagtgccatg gcatgatcac atctcactgc ggcctccatc    41640
acctgggctc aagcaatcct cccatctcag cctcccaagt agctgggact actggcacca    41700
ccatacctgg ctaatttttt gttgttgttg tttaatttttt aatacagatg aagcctcact    41760
atgttgccca ggctgctctt gaactcctgg gctcaagtga tcctccggcc ttggcctccc    41820
aaagtgctgg gattacaggc atgagccacc gtgcccagcc catcagatgt taatgctaca    41880
cgcacttgct taaaatcccc cagataattc tcgctgctct tggaataatt cccacacacc    41940
ttggcgtggc catgcaggct ctgtgccatc ggatatgtcc ctgcccctc tcccaactcc     42000 tcctttcgct tgctcgttca ctcagttcca gccacattgc cctgggagct gctcccacca    42060
tggggcttcc taatgcactg gtctctctca tgcagtgggg cctctccctc cttttactca    42120
gtgtctccca gcacccacct cctccagagc cttccctgac caccacacct acacctaggc    42180
ccttcctcct ccacgctccc tcctccaccc cggcctccta cccacgtgtc acttcttat     42240 actcgctgcc acctgaaatt agatcattta tttaccccctt tatttgttca gtttgccttg   42300
tccgttagaa tataagcttc caagggcag gagctttgcc tatattgtta ggccgggcat     42360
acaatgagca ctcaaaaaaa tatttgatga gtgtatgaaa gaacagactg ggttatgtaa    42420
ttgtgcctac ttacctatay gaccrtgtgg tggggtttat ggtgggtgtg gtggtgatgg   42480
ctatagggct ataagcaaat ttgggacagg gagtctaaga aatgttctta aattttagta    42540
agcaaagcat cctctacaga acctgtctta aaacatgaaa gttccttagt gctaccccca    42600
gaggtatgat ttggtaggtc aaggataggg cctggaaatt cacattcttg ttaagatgtt    42660
cttcatccgg ggtttgttga ccaccttttc agaagatttt tgctctgtag ctgtactacc    42720
caatgcagta gttcgtagtc agtgtggctc ctgagcccctt gaagtgtagc tcctctgaac    42780
```

-continued

```
tgagacgtgc tgtaaatgta aattgcacac cggagtttga agagttaata caaagaaaaa    42840
ggaatgcaaa acatctcatt aataatgctt tacactgatt acatattgaa atggtaatct    42900
tgtagatata gtgcgttaaa taaaatatac tgttaggctt aatttcacgt ctttatactt    42960
ttaatgtggc tactagaaaa atttaaataa catattcagc tcacattata ctcctattga    43020
acagagctga tctataagtt ccatggaaga tggcaagtct tcgcagctg                43069
```

<210> SEQ ID NO 2
<211> LENGTH: 875
<212> TYPE: DNA
<213> ORGANISM: homo sapiens
<220> FEATURE:
<221> NAME/KEY: 5'UTR
<222> LOCATION: 1..74
<220> FEATURE:
<221> NAME/KEY: misc_feature
<222> LOCATION: 75..77
<223> OTHER INFORMATION: ATG
<220> FEATURE:
<221> NAME/KEY: misc_feature
<222> LOCATION: 558..560
<223> OTHER INFORMATION: stop :TAA
<220> FEATURE:
<221> NAME/KEY: polyA_signal
<222> LOCATION: 851..856
<223> OTHER INFORMATION: AATAAA
<220> FEATURE:
<221> NAME/KEY: 3'UTR
<222> LOCATION: 561..875
<220> FEATURE:
<221> NAME/KEY: misc_feature
<222> LOCATION: 74..584
<223> OTHER INFORMATION: homology with sequence in ref embl : X52195
<220> FEATURE:
<221> NAME/KEY: misc_feature
<222> LOCATION: 354
<223> OTHER INFORMATION: diverging nucleotide C in ref embl : X52195
<220> FEATURE:
<221> NAME/KEY: misc_feature
<222> LOCATION: 555
<223> OTHER INFORMATION: diverging nucleotide T in ref embl : X52195
<220> FEATURE:
<221> NAME/KEY: allele
<222> LOCATION: 197
<223> OTHER INFORMATION: 10-33-175 : polymorphic base Y
<220> FEATURE:
<221> NAME/KEY: allele
<222> LOCATION: 453
<223> OTHER INFORMATION: 10-36-164 : polymorphic base R
<220> FEATURE:
<221> NAME/KEY: allele
<222> LOCATION: 779
<223> OTHER INFORMATION: 10-498-192 : polymorphic base R

<400> SEQUENCE: 2

```
acttcccctt cctgtacagg gcaggttgtg cagctggagg cagagcagtc ctctctgggg     60
agcctgaagc aaac atg gat caa gaa act gta ggc aat gtt gtc ctg ttg     110
              Met Asp Gln Glu Thr Val Gly Asn Val Val Leu Leu
                1               5                  10 gcc atc gtc acc ctc atc agc gtg gtc cag aat gga ttc ttt gcc cat     158
Ala Ile Val Thr Leu Ile Ser Val Val Gln Asn Gly Phe Phe Ala His
             15                  20                  25 aaa gtg gag cac gaa agc agg acc cag aat ggg agg agy ttc cag agg     206
Lys Val Glu His Glu Ser Arg Thr Gln Asn Gly Arg Ser Phe Gln Arg
         30                  35                  40 acc gga aca ctt gcc ttt gag cgg gtc tac act gcc aac cag aac tgt     254
Thr Gly Thr Leu Ala Phe Glu Arg Val Tyr Thr Ala Asn Gln Asn Cys
     45                  50                  55                  60
```

-continued

```
gta gat gcg tac ccc act ttc ctc gct gtg ctc tgg tct gcg ggg cta      302
Val Asp Ala Tyr Pro Thr Phe Leu Ala Val Leu Trp Ser Ala Gly Leu
            65                  70                  75 ctt tgc agc caa gtt cct gct gcg ttt gct gga ctg atg tac ttg ttt      350
Leu Cys Ser Gln Val Pro Ala Ala Phe Ala Gly Leu Met Tyr Leu Phe
        80                  85                  90 gtg agg caa aag tac ttt gtc ggt tac cta gga gag aga acg cag agc      398
Val Arg Gln Lys Tyr Phe Val Gly Tyr Leu Gly Glu Arg Thr Gln Ser
    95                 100                 105 acc cct ggc tac ata ttt ggg aaa cgc ata ctc ttc ctg ttc ctc          446
Thr Pro Gly Tyr Ile Phe Gly Lys Arg Ile Ile Leu Phe Leu Phe Leu
110                 115                 120 atg tcc rtt gct ggc ata ttc aac tat tac ctc atc ttc ttt ttc gga      494
Met Ser Xaa Ala Gly Ile Phe Asn Tyr Tyr Leu Ile Phe Phe Phe Gly
125                 130                 135                 140 agt gac ttt gaa aac tac ata aag acg atc tcc acc acc atc tcc cct      542
Ser Asp Phe Glu Asn Tyr Ile Lys Thr Ile Ser Thr Thr Ile Ser Pro
                145                 150                 155 cta ctt ctc att ccc taa ctctctgctg aatatggggt tggtgttctc             590
Leu Leu Leu Ile Pro  *
            160 atctaatcaa tacctacaag tcatcataat tcagctcttg agagcattct gctcttcttt    650 agatggctgt aaatctattg gccatctggg cttcacagct tgagttaacc ttgcttttcc    710 gggaacaaaa tgatgtcatg tcagctccgc cccttgaaca tgaccgtggc cccaaatttg    770 ctattcccrt gcattttgtt tgtttcttca cttatcctgt tctctgaaga tgttttgtga    830 ccaggtttgt gttttcttaa aataaaatgc agagacatgt tttaa                    875
```

<210> SEQ ID NO 3
<211> LENGTH: 161
<212> TYPE: PRT
<213> ORGANISM: homo sapiens
<220> FEATURE:
<221> NAME/KEY: VARIANT
<222> LOCATION: 127
<223> OTHER INFORMATION: 10-36-164 : polymorphic amino acid Val or Ile

<400> SEQUENCE: 3

```
Met Asp Gln Glu Thr Val Gly Asn Val Val Leu Leu Ala Ile Val Thr
1               5                   10                  15

Leu Ile Ser Val Val Gln Asn Gly Phe Phe Ala His Lys Val Glu His
                20                  25                  30

Glu Ser Arg Thr Gln Asn Gly Arg Ser Phe Gln Arg Thr Gly Thr Leu
            35                  40                  45

Ala Phe Glu Arg Val Tyr Thr Ala Asn Gln Asn Cys Val Asp Ala Tyr
        50                  55                  60

Pro Thr Phe Leu Ala Val Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Xaa Ala
        115                 120                 125

Gly Ile Phe Asn Tyr Tyr Leu Ile Phe Phe Phe Gly Ser Asp Phe Glu
    130                 135                 140

Asn Tyr Ile Lys Thr Ile Ser Thr Thr Ile Ser Pro Leu Leu Leu Ile
145                 150                 155                 160
```

Pro

<210> SEQ ID NO 4
<211> LENGTH: 46
<212> TYPE: DNA
<213> ORGANISM: homo sapiens

<400> SEQUENCE: 4
ctacactgcc aagtgagtcc taaacctgat gttgctaata agtggg        46

<210> SEQ ID NO 5
<211> LENGTH: 46
<212> TYPE: DNA
<213> ORGANISM: homo sapiens

<400> SEQUENCE: 5
ctacactgcc aagtgagtcc taaccctgat gttgctaata agtggg        46

<210> SEQ ID NO 6
<211> LENGTH: 19
<212> TYPE: DNA
<213> ORGANISM: homo sapiens

<400> SEQUENCE: 6
ggacatttag ggttgcttg        19

<210> SEQ ID NO 7
<211> LENGTH: 19
<212> TYPE: DNA
<213> ORGANISM: homo sapiens

<400> SEQUENCE: 7
tgttttgaca ctagcactc        19

<210> SEQ ID NO 8
<211> LENGTH: 19
<212> TYPE: DNA
<213> ORGANISM: homo sapiens

<400> SEQUENCE: 8
actgccaagt gagtcctaa        19

<210> SEQ ID NO 9
<211> LENGTH: 48
<212> TYPE: DNA
<213> ORGANISM: homo sapiens

<400> SEQUENCE: 9
ctgactagga cctctgattc ttctctccct gagctttgaa ggctctga        48

<210> SEQ ID NO 10
<211> LENGTH: 48
<212> TYPE: DNA
<213> ORGANISM: homo sapiens

<400> SEQUENCE: 10
ctgactagga cctctgattc ttctttccct gagctttgaa ggctctga        48

<210> SEQ ID NO 11
<211> LENGTH: 18
<212> TYPE: DNA
<213> ORGANISM: homo sapiens

```
-continued

<400> SEQUENCE: 11
gaaggttctc aggtttcc                                                   18

<210> SEQ ID NO 12
<211> LENGTH: 18
<212> TYPE: DNA
<213> ORGANISM: homo sapiens

<400> SEQUENCE: 12
agctgtattt tcagagcc                                                   18

<210> SEQ ID NO 13
<211> LENGTH: 19
<212> TYPE: DNA
<213> ORGANISM: homo sapiens

<400> SEQUENCE: 13
taggacctct gattcttct                                                  19

<210> SEQ ID NO 14
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 14
tgtaaaacga cggccagt                                                   18

<210> SEQ ID NO 15
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 15
caggaaacag ctatgacc                                                   18
```

GENOMIC SEQUENCE OF THE 5-LIPOXYGENASE-ACTIVATING PROTEIN (FLAP), POLYMORPHIC MARKERS THEREOF AND METHODS FOR DETECTION OF ASTHMA

CROSS-REFERENCE TO RELATED APPLICATIONS

The present application is a divisional of U.S. application Ser. No. 10/359,512, filed Feb. 5, 2003, which is a divisional of U.S. application Ser. No. 09/292,542, filed Apr. 15, 1999, now U.S. Pat. No. 6,531,279, which claims priority from U.S. Provisional Application Ser. No. 60/081,893, filed Apr. 15, 1998; U.S. Provisional Application Ser. No. 60/091,314, filed Jun. 30, 1998; and U.S. Provisional Application Ser. No. 60/123,406, filed Mar. 8, 1999, all of which are hereby incorporated by reference herein in their entireties, including any figures, tables, nucleic acid sequences, amino acid sequences, or drawings.

FIELD OF INVENTION

The invention concerns the genomic sequence of the FLAP gene. The invention also concerns biallelic markers of a FLAP gene and the association established between these markers and diseases involving the leukotriene pathway such as asthma. The invention provides means to determine the predisposition of individuals to diseases involving the leukotriene pathway as well as means for the diagnosis of such diseases and for the prognosis/detection of an eventual treatment response to agents acting on the leukotriene pathway.

BACKGROUND OF THE INVENTION

The progression of inflammatory diseases in which the synthesis of leukotrienes plays an active role, such as asthma and arthritis, constitutes a major health problem in Western societies.

For example, the prevalence of asthma in Occidental countries has risen steadily over the last century, affecting about 10% of the population. In 1994, it afflicted more than 14 million people in the United States alone (including 4.8 million (6.9%) less than 18 years of age) whereas only 8 million people suffered from the same disease in 1982. It claims more than 5000 lives each year (including 342 deaths among persons aged less than 25 in 1993). Asthma affects one child in seven in Great Britain, and in the United States, it causes one-third of pediatric emergency-room visits. It is the most frequent chronic disease in childhood.

Bronchial asthma is a multifactorial syndrome rather than a single disease, defined as airway obstruction and characterized by inflammatory changes in the airways and bronchial hyper-responsiveness. Stimuli which cause the actual asthma attacks include allergens (in sensitized individuals), exercise (in which one stimulus may be cold air), respiratory infections and atmospheric pollutants such as sulphur dioxide. The asthmatic subject has intermittent attacks of dyspnoea (difficulty in breathing out), wheezing, and cough that can be life-threatening or even fatal.

The manifestation of asthma probably involves both genetic and environmental factors, and in most subjects the asthmatic attack consists of two phases which illustrate the pathophysiology of the condition:

an immediate phase, consisting mainly of bronchospasms due to spasms of the bronchial smooth muscle; the cells involved are mast cells releasing histamine, but also eosinophils, macrophages and platelets releasing leukotrienes, prostaglandins, and platelet-activating factor; these spasmogens added to chemotaxins and chemokins attract leukocytes into the area, setting the stage for the delayed phase;

a later phase consisting of a special type of inflammation comprising vasodilatation, oedema, mucus secretion and bronchospasm; it is caused by inflammatory mediators released from activated cytokine-releasing T cells and eosinophils, and, possibly, neuropeptides released by axon reflexes; these mediators cause damage and loss of bronchial epithelium.

The strongest identifiable predisposing factor for developing asthma is atopy, the predisposition for the development of an IgE-mediated response to common aeroallergens. When IgE binds to the IgE receptors on the cells, the system becomes primed so that subsequent re-exposure to the relevant allergen will cause an asthmatic attack. Most asthma cases (95%) are associated with atopy.

Further to their above-mentioned role in asthma, leukotrienes are more generally involved in host defense reactions and play an important role in immediate hypersensitivity as well as in inflammatory diseases other than asthma such as inflammatory bowel disease, psoriasis and arthritis.

The Leukotriene Pathway

Leukotrienes are products of the Lipoxygenase pathways. Lipoxygenases are soluble enzymes located in the cytosol and are found in lung, platelets, mast cells, and white blood cells. The main enzyme in this group is 5-Lipoxygenase which is the first enzyme in the biosynthesis of leukotrienes.

The first step in leukotriene biosynthesis is the release of arachidonic acid from membrane phospholipids upon cell stimulation (for example, by immune complexes and calcium ionophores). Arachidonic acid is then converted into leukotrienes A4 by a 5-Lipoxygenase (5-LO) which translocates to the cell membrane where it becomes associated to a protein called "five-Lipoxygenase activating protein" (FLAP), which is necessary for leukotriene synthesis in intact cells. 5-LO also has leukotriene A4 hydrolase activity.

Leukotriene A4 (LTA4), an unstable epoxide intermediate, is then hydrolyzed into leukotriene B4 (LTA4-hydrolase activity) or conjugated with glutathione to yield leukotriene C4 (LTC4-synthase activity) and its metabolites, leukotriene D4 and leukotriene E4. LTB4 is produced mainly by neutrophils, while cysteinyl-leukotrienes (LTC4, LTD4, and LTE4) are mainly produced by eosinophils, mast cells, basophils, and macrophages.

LTB4 is a powerful chemotactic agent for both neutrophils and macrophages. On neutrophils, it also causes up-regulation of membrane adhesion molecules and increases the production of toxic oxygen products and the release of granule enzymes. On macrophages and lymphocytes, it stimulates proliferation and cytokine release. Thus LTB4 is an important mediator in all types of inflammations.

Cysteinyl-leukotrienes act on the respiratory and cardiovascular systems. In the respiratory system, they are potent spasmogens causing a contraction of bronchiolar muscle and an increase in mucus secretion. In the cardiovascular system, they cause vasodilatation in most vessels, but they also act as coronary vasoconstrictors. The cysteinyl-leukotrienes are of particular importance in asthma.

FLAP (5-Lipoxygenase-Activating Protein)

FLAP is a 18-kD membrane-bound polypeptide which specifically binds arachidonic acid and activates 5-LO by acting as an arachidonic acid transfer protein. The FLAP gene spans greater than 31 kb and consists of five small exons and four large exons (See GenBank 182657, Kennedy et al. 1991 incorporated herein by reference, Genbank M60470 for exon 1, Genbank M63259 for exon 2, Genbank M63260 for exon 3, Genbank M63261 for exon 4, and Genbank M6322 for exon 5).

The nuclear envelope is the intracellular site at which 5-LO and FLAP act to metabolize arachidonic acid, and ionophore activation of neutrophils and monocytes results in the translocation of 5-LO from a nonsedimentable location to the nuclear envelope. Inhibitors of FLAP function prevent translocation of 5-LO from cytosol to the membrane and inhibit 5-LO activation. They are thus interesting anti-inflammatory drug candidates. Indeed, antagonists of FLAP can attenuate allergen-induced bronchoconstrictor responses which supports an important role for cysteinyl leukotrienes in mediating these asthmatic responses.

Pharmacogenomics

To assess the origins of individual variations in disease susceptibility or drug response, pharmacogenomics uses the genomic technologies to identify polymorphisms within genes that are part of biological pathways involved in disease susceptibility, etiology, and development, or more specifically in drug response pathways responsible for a drug's efficacy, tolerance, or toxicity, including but not limited to drug metabolism cascades.

In this regard, the inflammatory phenomena which are involved in numerous diseases present a high relevance to pharmacogenomics both because they are at the core of many widespread serious diseases, and because targeting inflammation pathways to design new efficient drugs includes numerous risks of potentiating serious side-effects. The leukotriene pathway is particularly interesting since its products are powerful inflammatory molecules.

The vast majority of common diseases, such as cancer, hypertension and diabetes, are polygenic (involving several genes). In addition, these diseases are modulated by environmental factors such as pollutants, chemicals and diet. This is why many diseases are called multifactorial; they result from a synergistic combination of factors, both genetic and environmental.

For example, in addition to the evidenced impact of environmental factors on the development of asthma, patterns of clustering and segregation analyzes in asthmatic families have suggested a genetic component to asthma. However, the lack of a defined and specific asthma phenotype is proving to be a major hurdle for reliably detecting asthma-associated genes.

Asthma is usually diagnosed through clinical examination and biological testing. The non-specific bronchial hyper-responsiveness that accompanies asthma is measured by the variation of airflow triggered in a patient by the administration of a bronchoconstrictor such as histamine or methacholine. Atopy is detected by skin prick tests that measure serum IgE titers. Standard symptom questionnaires are also commonly used to detect symptoms characteristic of, but not unique to, asthma (like nocturnal wheeze and breathlessness).

However, there is no straightforward physiological or biological blood test for the asthmatic state. Despite advances in understanding the pathophysiology of asthma and its development, evidence suggests that the prevalence of the asthmatic state and the severity of asthma attacks is underestimated. As a result, adequate asthma treatment is often delayed, thereby allowing the inflammation process to better establish itself. Thus, there is a need for an efficient and reliable asthma diagnostic test.

Drug efficacy and toxicity may also be considered as multifactorial traits that involve genetic components in much the same way as complex diseases. In this respect, there are three main categories of genes that may theoretically be expected to be associated with drug response, namely genes linked with the targeted disease, genes related to the drug's mode of action, and genes involved in the drug's metabolism.

The primary goal of pharmacogenomics in the study of asthma is to look for genes that are related to drug response. It can first provide tools to refine the design of drug development by decreasing the incidence of adverse events in drug tolerance studies, by better defining patient subpopulations of responders and non-responders in efficacy studies and, by combining the results obtained therefrom, to further allow for better individualized drug usage based on efficacy/tolerance prognosis.

Pharmacogenomics can also provide tools to identify new targets for drug design and to optimize the use of already existing drugs, in order to either increase their response rate and/or exclude non-responders from particular treatments, or decrease undesirable side-effects and/or exclude from corresponding treatment patients with significant risk of undesirable side-effects.

For this second application of pharmacogenomics, the leukotrienes pathway is also useful because many anti-asthmatic and anti-inflammatory agents which act through the leukotrienes pathway are under development, most of which show some incidence of severe side-effects.

For example, there are two major categories of anti-asthma drugs: bronchodilators and anti-inflammatory agents. Bronchodilators are effective in reversing the bronchospasm of the immediate phase of the disease. Drugs used as bronchodilators include the $\beta_2$-adrenoceptor agonists (dilating the bronchi by a direct action on the smooth muscle, e.g. salbutamol), the xanthines (e.g. theophylline) and the muscarinic-receptor antagonists (e.g. ipratropium bromide). These represent the short term attack symptomatic treatment.

Anti-inflammatory agents are effective in inhibiting or preventing the production of inflammatory components in both asthma phases. They include glucocorticoids, sodium cromoglycate and histamine H1-receptor antagonists. These agents represent the current long term treatment of the asthmatic state.

However, none of these currently used anti-asthmatic drugs is completely satisfactory as none actually "cures" all patients with the disease. Glucocorticoids are the most interesting active compounds in this regard but they have potentially serious unwanted side-effects (oropharyngeal candidiasis, dysphonia and osteoporosis for inhaled glucocorticoids, and mood disturbances, increased appetite and loss of glucose control in diabetics for systemic glucocorticoids).

In recent years, more effective and selective leukotriene biosynthesis inhibitors (e.g., 5-LO and FLAP-binding inhibitors) have been developed and used as novel therapies for bronchial asthma and other inflammatory disorders. For example, Zileuton (Zyflo®), an inhibitor of 5-LO commercialized by Abbott Laboratories (Abbott Park, Ill.), has been shown to improve airway function and to reduce asthma-related symptoms.

Unfortunately, undesirable side-effects such as acute exacerbation of asthma, dyspepsia and elevated liver enzymes have been reported in clinical trials for Zileuton. There is also concern about drug interactions with hepatically cleared medicaments.

Thus, in addition to the need for the development of an efficient and reliable asthma diagnostic test, there is also a need to develop more effective and better targeted therapeutic strategies acting on the leukotrienes pathway with reduced side-effects and low toxicity for the user. One way to achieve this in the relative short term would be through the use of pharmacogenomics results, to better define the use of existing drugs or drug candidates in order to enhance the benefit/risk ratio on target subpopulations of patients.

SUMMARY OF THE INVENTION

The present invention stems from the isolation and characterization of the whole genomic sequence of the FLAP gene including its regulatory regions. Oligonucleotide probes and primers hybridizing specifically with a genomic sequence of FLAP are also part of the invention. A further object of the invention consists of recombinant vectors comprising any of the nucleic acid sequences described in the present invention, and in particular recombinant vectors comprising the regulatory region of FLAP or a sequence encoding the FLAP enzyme, as well as cell hosts comprising said nucleic acid sequences or recombinant vectors. The invention also encompasses methods of screening of molecules which modulate or inhibit the expression of the FLAP gene. The invention also comprises a new allelic variant of the FLAP protein.

The invention is also directed to biallelic markers that are located within the FLAP genomic sequence, these biallelic markers representing useful tools in order to identify a statistically significant association between specific alleles of the FLAP gene and diseases involving the leukotriene pathway such as inflammatory diseases, or between specific alleles of FLAP gene and either side-effects resulting from the administration of agents acting on the leukotriene pathway, preferably Zileuton, or a beneficial response to treatment with agents acting on the leukotriene pathway. These associations are within the scope of the invention.

More particularly, the present invention stems from the identification of genetic associations between alleles of biallelic markers of the FLAP gene and asthma, as confirmed and characterized in a panel of human subjects.

Methods and products are provided for the molecular detection of a genetic susceptibility in humans to diseases involving the leukotriene pathway such as inflammatory diseases and comprising, among others, asthma, arthritis, psoriasis and inflammatory bowel disease. They can be used for diagnosis, staging, prognosis, and monitoring of such diseases, which processes can be further included within treatment approaches. The invention also provides for the efficient design and evaluation of suitable therapeutic solutions including individualized strategies for optimizing drug usage, and screening of potential new medicament candidates.

BRIEF DESCRIPTION OF THE DRAWINGS

FIG. 2 is a graph demonstrating the association between some of the biallelic markers of the invention and asthma with the absolute value of the logarithm (base 10) of the p-value of the chi-square values for each marker shown on the y-axis and a rough estimate of the position of each marker with respect to the FLAP gene elements on the x-axis.

FIG. 3 is a table demonstrating the results of a haplotype association analysis between asthma and haplotypes which consist of biallelic markers of the invention. (297 cases vs 286 Caucasian US controls)

FIG. 4 is a table demonstrating the results of a haplotype frequency analysis including permutation testing with more than 1000 iterations.

BRIEF DESCRIPTION OF THE SEQUENCES PROVIDED IN THE SEQUENCE LISTING

Figure 1:
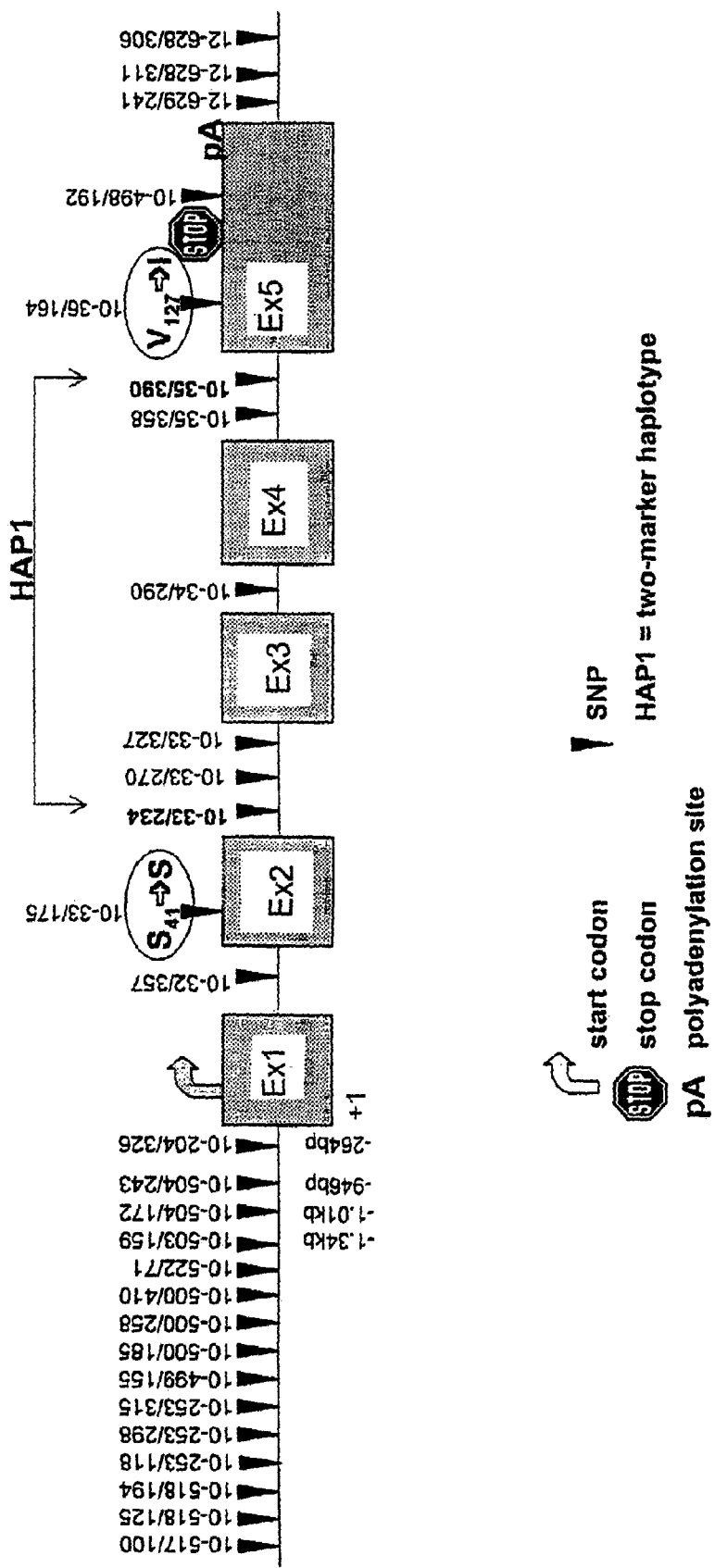
FIG. 1 is a diagram of the FLAP gene with an indication of the relative position of the biallelic markers of the present invention.

SEQ ID No 1 contains a genomic sequence of FLAP comprising the 5' regulatory region (upstream untranscribed region), the exons and introns, and the 3' regulatory region (downstream untranscribed region).

SEQ ID No 2 contains a complete human FLAP cDNA with 5' and 3' UTRs.

SEQ ID No 3 contains the FLAP protein encoded by the cDNA of SEQ ID No 2.

SEQ ID Nos 4 and 5 contain either allele 1 or 2 of the biallelic marker A14 and its surrounding sequence.

SEQ ID Nos 6 and 7 contain the sequence of amplification primers for the biallelic marker A14.

SEQ ID No 8 contains the sequence of a microsequencing primer of the biallelic marker A14.

SEQ ID Nos 9 and 10 contain either allele 1 or 2 of the biallelic A19 and its surrounding sequence.

SEQ ID Nos 11 and 12 contain the sequence of amplification primers for the biallelic marker A19.

SEQ ID No 13 contains the sequence of a microsequencing primer of the biallelic marker A19.

SEQ ID No 14 contains a primer containing the additional PU 5' sequence described further in Example 2.

SEQ ID No 15 contains a primer containing the additional RP 5' sequence described further in Example 2.

DETAILED DESCRIPTION OF THE INVENTION

5-LO is associated with FLAP for leukotriene synthesis. Indeed, it appears that regulation of the production of leukotrienes can be achieved either through the action of direct 5-LO inhibitors or indirect leukotriene biosynthesis inhibitors which bind to FLAP.

The present invention concerns the identification and characterization of biallelic markers in a FLAP encoding gene, as well as the identification of significant polymorphisms associated with diseases involving the leukotriene pathway. Preferably, the polymorphisms are associated with asthma.

The identified polymorphisms are used in the design of assays for the reliable detection of genetic susceptibility to diseases involving the leukotriene pathway. They can also be used in the design of drug screening protocols to provide an accurate and efficient evaluation of the therapeutic and side-effect potential of new or already existing medicaments.

I. Definitions

Before describing the invention in greater detail, the following definitions are set forth to illustrate and define the meaning and scope of the terms used to describe the invention herein.

The term "FLAP gene", when used herein, encompasses genomic, mRNA and cDNA sequences encoding the FLAP protein. In the case of a genomic sequence, the FLAP gene also includes native regulatory regions which control the expression of the coding sequence of the FLAP gene.

As used interchangeably herein, the terms "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "purified" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50, preferably 60 to 75% of a sample exhibits a single polynucleotide sequence and conformation (linear versus covalently closed). A substantially pure polynucleotide typically comprises about 50 , preferably 60 to 90% weight/weight of a nucleic acid sample, more usually about 95%, and preferably is over about 99% pure. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

As used herein, the term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "purified" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as agarose or polyacrylamide gel electrophoresis of a sample, followed by visualizing a single polypeptide band upon staining the gel. For certain purposes higher resolution can be provided by using HPLC or other means well known in the art.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments.

As used herein, an "antigenic determinant" is the portion of an antigen molecule, in this case a FLAP polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984; PCT Publication No WO 84/03564; and PCT Publication No WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., 1995).

The terms "complementary" or "complement thereof" are used herein to refer to the sequences of polynucleotides which are capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "allele" is used herein to refer to variants of a nucleotide sequence. Diploid organisms may be homozygous or heterozygous for an allelic form.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined hereinbelow) which can be used to identify a specific polynucleotide sequence present in samples, said nucleic acid segment comprising a nucleotide sequence complementary of the specific polynucleotide sequence to be identified.

The term "heterozygosity rate" is used herein to refer to the incidence of individuals in a population, which are heterozygous at a particular allele. In a biallelic system the heterozygosity rate is on average equal to $2P_a(1-P_a)$, where $P_a$ is the frequency of the least common allele. In order to be useful in genetic studies a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. Typically, between different genomes or between different individuals, the polymorphic site may be occupied by two different nucleotides.

"Biallelic markers" consist of a single base polymorphism. Each biallelic marker therefore corresponds to two forms of a polynucleotide sequence included in a gene, which, when compared with one another, present a nucleotide modification at one position. Usually, the nucleotide modification involves the substitution of one nucleotide for another (for example C instead of T). Typically the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker."

As used herein the terminology "defining a biallelic marker" means that a sequence includes a polymorphic base from a biallelic marker. The sequences defining a biallelic marker may be of any length consistent with their intended use, provided that they contain a polymorphic base from a biallelic marker. The sequence has between 1 and 500 nucleotides in length, preferably between 5, 10, 15, 20, 25, or 40 and 200 nucleotides and more preferably between 30 and 50 nucleotides in length. Preferably, the sequences defining a biallelic marker include a polymorphic base selected from the group consisting of biallelic markers A1 to A28. In some embodiments the sequences defining a biallelic marker comprise one of the sequences selected from the group consisting of P1 to P28. Likewise, the term "marker" or "biallelic marker" requires that the sequence is of sufficient length to practically (although not necessarily unambiguously) identify the polymorphic allele, which usually implies a length of at least 4, 5, 6, 10, 15, 20, 25, or 40 nucleotides.

The invention also concerns FLAP-related biallelic markers. The term "FLAP-related biallelic marker" and "biallelic marker of the FLAP gene" are used interchangeably herein to relate to all biallelic markers in linkage disequilibrium with the FLAP gene. The term FLAP-related biallelic marker includes, but is not limited to, both the genic and non-genic biallelic markers described in FIG. 1.

The term "non-genic" is used herein to describe FLAP-related biallelic markers, as well as polynucleotides and primers which occur outside the nucleotide positions shown in the human FLAP genomic sequence of SEQ ID No 1. The term "genic" is used herein to describe FLAP-related biallelic markers as well as polynucleotides and primers which do occur in the nucleotide positions shown in the human FLAP genomic sequence of SEQ ID No 1.

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease involving the leukotriene pathway; or to refer to an individual's response to an agent acting on the leukotriene pathway; or to refer to symptoms of, or susceptibility to side-effects to an agent acting on the leukotriene pathway.

The term "disease involving the leukotriene pathway" refers to a condition linked to disturbances in expression, production or cellular response to leukotrienes. The diseases involving the leukotriene pathway include, but are not limited to, such as angina, endotoxic shock, psoriasis, atopic eczema, rheumatoid arthritis, inflammatory bowel disease, osteoarthritis, tendinitis, bursitis, ulcerative colitis, allergic bronchoasthma, allergic rhinitis, allergic conjunctivitis, glomerulonephritis, migraine headaches, and more particularly asthma.

The terms "response to an agent acting on the leukotriene pathway" refer to drug efficacy, including but not limited to ability to metabolize a compound, to the ability to convert a pro-drug to an active drug, and to the pharmacokinetics (absorption, distribution, elimination) and the pharmacodynamics (receptor-related) of a drug in an individual. In the context of the present invention, a "positive response" to a medicament can be defined as comprising a reduction of the symptoms related to the disease or condition to be treated. In the context of the present invention, a "negative response" to a medicament can be defined as comprising either a lack of positive response to the medicament which does not lead to a symptom reduction or to a side-effect observed following administration of the medicament.

The terms "side-effects to an agent acting on the leukotriene pathway" refer to adverse effects of therapy resulting from extensions of the principal pharmacological action of the drug or to idiosyncratic adverse reactions resulting from an interaction of the drug with unique host factors. The side-effects related to treatment with agents acting on the leukotriene pathway are preferably an acute exacerbation of an inflammatory disease such as asthma, infection and headache, and more preferably an increase in liver transaminase levels.

The terms "agents acting on the leukotriene pathway" preferably refer to a drug or a compound which modulates the activity or concentration of any enzyme or regulatory molecule involved in the leukotriene pathway in a cell or animal. Preferably these agents can be selected from the following group: FLAP inhibitors such as BAYx 1005, MK-886, and MK-0591; 5-Lipoxygenase inhibitors such as Zileuton, BAY-G576, RS-43,179, Wy-47,288, vitamin A, and BW A4C; Leukotriene LTD4 receptor antagonists such as zafirlukast, ICI 204,219, MK-571, MK-679, ONO-RS-411, SK&F 104,353, and Wy-48,252; Leukotriene B4 receptor antagonists; Leukotriene C4 synthase inhibitors; and, Leukotriene A4 hydrolase inhibitors. "Agents acting on the leukotriene pathway" further refers to non-steroidal antiinflammatory drugs (NSAIDs), leukotriene receptor antagonists and leukotriene analogs. "Agents acting on the leukotriene pathway" also refers to compounds modulating the formation and action of leukotrienes.

Some of the compounds cited above are described in U.S Pat. Nos. 4,873,259; 4,970,215; 5,310,744; 5,225,421; and U.S. Pat. No. 5,081,138; or in EP 0 419 049, the disclosures of which are incorporated herein by reference.

The term "individual" as used herein refers to vertebrates, particularly members of the mammalian species and includes but is not limited to domestic animals, sports animals, laboratory animals, primates and humans. Preferably, an individual is a human.

Variants and Fragments

Polynucleotides

The invention also relates to variants and fragments of the polynucleotides described herein, particularly of a FLAP gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Changes in the nucleotide of a variant may be silent, which means that they do not alter the amino acids encoded by the polynucleotide.

However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature FLAP protein.

A polynucleotide fragment is a polynucleotide having a sequence that entirely is the same as part but not all of a given nucleotide sequence, preferably the nucleotide sequence of a FLAP gene, and variants thereof. The fragment can be a portion of an exon or of an intron of a FLAP gene. It can also be a portion of the regulatory sequences of the FLAP gene. Preferably, such fragments comprise the polymorphic base of at least one of the biallelic markers A1 to A28, the complement therefor, or a biallelic marker in linkage disequillibrium with one or more of the biallelic markers A1 to A28.

Such fragments may be "free-standing", i.e. not part of or fused to other polynucleotides, or they may be comprised within a single larger polynucleotide of which they form a part or region. However, several fragments may be comprised within a single larger polynucleotide.

As representative examples of polynucleotide fragments of the invention, there may be mentioned those which have from about 4, 6, 8, 15, 20, 25, 40, 10 to 20, 10 to 30, 30 to 55, 50 to 100, 75 to 100 or 100 to 200 nucleotides in length. Preferred are those fragments having about 47 nucleotides in length, such as those of P1 to P28, and containing at least one of the biallelic markers of a FLAP gene which are described herein. It will of course be understood that the polynucleotides P1 to P28 can be shorter or longer, although it is preferred that they at least contain the polymorphic base of the biallelic marker which can be located at one end of the fragment.

Polypeptides

The invention also relates to variants, fragments, analogs and derivatives of the polypeptides described herein, including mutated FLAP proteins.

The variant may be 1) one in which one or more of the amino acid residues are substituted with a conserved or non-conserved amino acid residue (preferably a conserved amino acid residue) and such substituted amino acid residue may or may not be one encoded by the genetic code, or 2) one in which one or more of the amino acid residues includes a substituent group, or 3) one in which the mutated FLAP is fused with another compound, such as a compound to increase the half-life of the polypeptide (for example, polyethylene glycol), or 4) one in which the additional amino acids are fused to the mutated FLAP, such as a leader or secretory sequence or a sequence which is employed for purification of the mutated FLAP or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a FLAP gene and variants thereof. Preferred fragments include those of the active region of the FLAP protein that play a role in leukotriene biosynthesis and those regions possessing antigenic properties and which can be used to raise antibodies against the FLAP protein.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred are those fragments containing at least one amino acid mutation in the FLAP protein.

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989, are incorporated herein in their entirety. These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al. (1989).

Identity between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990; Altschul et al., 1993; Altschul et al., 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

II. Genomic Sequences of FLAP

Although the FLAP gene is of high relevance to pharmaceutical research, we still have scant knowledge concerning the extent and nature of sequence variation in this gene and its regulatory elements. The cDNA and part of the genomic sequence for human FLAP have been cloned and sequenced (Kennedy et al. 1991; Dixon et al, 1988). But, the complete genomic sequence of FLAP, including its regulatory elements, have not been described.

The present invention encompasses the genomic sequence of the FLAP gene of SEQ ID No 1 or a variant thereof or the complementary sequence thereto. This polynucleotide of nucleotide sequence of SEQ ID No 1, or a variant thereof or the complementary sequence thereto, may be purified, isolated, or recombinant. The FLAP genomic sequences comprise exons and introns. The nucleic acids derived from the FLAP intronic polynucleotides may be used as oligonucleotide primers or probes in order to detect the presence of a copy of the FLAP gene in a test sample, or alternatively in order to amplify a target nucleotide sequence within the FLAP sequences.

The invention also encompasses a purified, isolated, or recombinant polynucleotides comprising a nucleotide sequence having at least 70, 75, 80, 85, 90, or 95% nucleotide identity with a nucleotide sequence of SEQ ID No 1 or a complementary sequence thereto or a fragment thereof. The nucleotide differences as regards to the nucleotide sequence of SEQ ID No 1 may be generally randomly distributed throughout the entire nucleic acid. Nevertheless, preferred nucleic acids are those wherein the nucleotide differences as regards to the nucleotide sequence of SEQ ID No 1 are predominantly located outside the coding sequences contained in the exons. These nucleic acids, as well as their fragments and variants, may be used as oligonucleotide primers or probes in order to detect the presence of a copy of the FLAP gene in a test sample, or alternatively in order to amplify a target nucleotide sequence within the FLAP sequences.

The FLAP genomic nucleic acid comprises 5 exons. Exon 1 starts at the nucleotide in position 7709 and ends at the nucleotide in position 7852 of the nucleotide sequence of SEQ ID No 1; Exon 2 starts at the nucleotide in position 16236 and ends at the nucleotide in position 16335 of the nucleotide sequence of SEQ ID No 1; Exon 3 starts at the nucleotide in position 24227 and ends at the nucleotide in position 24297 of the nucleotide sequence of SEQ ID No 1; Exon 4 starts at the nucleotide in position 28133 and ends at the nucleotide in position 28214 of the nucleotide sequence of SEQ ID No 1; Exon 5 starts at the nucleotide in position 36128 and ends at the nucleotide in position 36605 of the nucleotide sequence of SEQ ID No 1. The invention also deals with purified, isolated, or recombinant nucleic acids comprising a combination of at least two exons of the FLAP gene, wherein the polynucleotides are arranged within the nucleic acid, from the 5'-end to the 3'-end of said nucleic acid, in the same order than in SEQ ID No 1.

The present invention also concerns a purified and/or isolated nucleic acid encoding a FLAP protein, preferably comprising at least one of the biallelic polymorphisms described herewith, and more preferably a FLAP gene comprising the trait-causing mutation determined using the below-noted method. In some embodiments, the FLAP gene comprises one or more of the sequences of P1 to P13, P15, and P17 to P28, or the complementary sequence thereto, or a fragment or a variant thereof. Preferred polynucleotides comprise at least one biallelic marker selected from the group consisting of A1 to A13, A15, A17 to A28, and the complements thereof. The present invention also provides polynucleotides which, may be used as primers and probes in order to amplify fragments carrying biallelic markers or in order to detect biallelic marker alleles.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises at least 1, 2, 3, 5, or 10 of the following nucleotide positions of SEQ ID No 1: 1-7007, 8117-15994, 16550-24058, 24598-27872, 28413-35976, and 36927-43069. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises a C at position 16348, of SEQ ID No 1. Further preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises the following nucleotide positions of SEQ ID No 1: 7612-7637, 24060-24061, 24067-24068, 27903-27905, and 28327-28329. It should be noted that nucleic acid fragments of any size and sequence may also be comprised by the polynucleotides described in this section. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises a nucleotide selected from the group consisting of an A at position 7445, an A at position 7870, a T at position 16288, an A at position 16383, a T at position 24361, a G at position 28336, a T at position 28368, an A at position 36183, and a G at position 36509 of SEQ ID No 1.

While this section is entitled "Genomic Sequences of FLAP," it should be noted that nucleic acid fragments of any size and sequence may also be comprised by the polynucleotides described in this section, flanking the genomic sequences of FLAP on either side or between two or more such genomic sequences.

Regulatory Regions of the FLAP Gene

The genomic sequence of the FLAP gene contains regulatory sequences both in the non-coding 5'-flanking region and in the non-coding 3'-flanking region that border the FLAP transcribed region containing the 5 exons of this gene. 5'-regulatory sequences of the FLAP gene comprise the polynucleotide sequences located between the nucleotide in position 1 and the nucleotide in position 7708 of the nucleotide sequence of SEQ ID No 1, more preferably between positions 1 and 7007 of SEQ ID No 1. 3'-regulatory sequences of the FLAP gene comprise the polynucleotide sequences located between the nucleotide in position 36606 and the nucleotide in position 43069 of the nucleotide sequence of SEQ ID No 1.

Polynucleotides carrying the regulatory elements located both at the 5' end and at the 3' end of the FLAP coding region may be advantageously used to control the transcriptional and translational activity of a heterologous polynucleotide of interest, said polynucleotide being heterologous as regards to the FLAP regulatory region.

Thus, the present invention also concerns a purified, isolated, and recombinant nucleic acid comprising a polynucleotide which is selected from the group consisting of the polynucleotide sequences located between the nucleotide in position 1 and the nucleotide in position 7708 of the nucleotide sequence of SEQ ID No 1, more preferably between positions 1 and 7007 of SEQ ID No 1 and the polynucleotide sequences located between the nucleotide in position 36606 and the nucleotide in position 43069 of SEQ ID No 1; or a sequence complementary thereto or a biologically active fragment thereof.

The invention also pertains to a purified or isolated nucleic acid comprising a polynucleotide having at least 95% nucleotide identity, advantageously 99% nucleotide identity, preferably 99.5% nucleotide identity and most preferably 99.8% nucleotide identity with a polynucleotide selected from the group consisting of the polynucleotide sequences located between the nucleotide in position 1 and the nucleotide in position 7708 of the nucleotide sequence of SEQ ID No 1, more preferably between positions 1 and 7007 of SEQ ID No 1 and the polynucleotide sequences located between the nucleotide in position 36606 and the nucleotide in position 43069 of SEQ ID No 1 or a variant thereof or a biologically active fragment thereof.

Another object of the invention consists of purified, isolated or recombinant nucleic acids comprising a polynucleotide that hybridizes, under the stringent hybridization conditions defined therein, with a polynucleotide selected from the group consisting of the polynucleotide sequences located between the nucleotide in position 1 and the nucleotide in position 7007 of SEQ ID No 1 and the polynucleotide sequences located between the nucleotide in position 36606 and the nucleotide in position 43069 of SEQ ID No, or a sequence complementary thereto or a variant thereof or a biologically active fragment thereof.

Furthermore, the present invention also concerns a purified, isolated, and recombinant nucleic acid comprising a polynucleotide which is selected from the group consisting of:
the polynucleotide sequences located between the nucleotide in position 1 and the nucleotide in position 7708 of the nucleotide sequence of SEQ ID No 1, more preferably between positions 1 and 7007 of SEQ ID No 1, and comprising a biallelic marker selected from the group consisting of A1 to A11 and A25 to A28, or a sequence complementary thereto or a biologically active fragment thereof; and the polynucleotide sequences located between the nucleotide in position 36606 and the nucleotide in position 43069 of SEQ ID No 1 and comprising a biallelic marker selected from the group consisting of A22 to A24 and the complements thereof, or a sequence complementary thereto or a biologically active fragment thereof.

By a "biologically active" fragment of SEQ ID No 1 according to the present invention is intended a polynucleotide comprising or alternatively consisting of a fragment of said polynucleotide which is functional as a regulatory region for expressing a recombinant polypeptide or a recombinant polynucleotide in a recombinant cell host.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

Preferred fragments of the 5'- or 3'-regulatory sequences have a length of about 1500 or 1000 nucleotides, preferably of about 500 nucleotides, more preferably about 400 nucleotides, even more preferably 300 nucleotides and most preferably about 200 nucleotides.

The regulatory polynucleotides of the invention may be prepared from the polynucleotide of SEQ ID No 1 by cleavage using suitable restriction enzymes, as described for example in the book of Sambrook et al. (1989). The regulatory polynucleotides may also be prepared by digestion of the polynucleotide of SEQ ID No 1 by an exonuclease enzyme, such as Bal31 (Wabiko et al., 1986). These regulatory polynucleotides can also be prepared by nucleic acid chemical synthesis, as described elsewhere in the specification.

The regulatory polynucleotides according to the invention may be advantageously part of a recombinant expression vector that may be used to express a coding sequence in a desired host cell or host organism.

A preferred 5'-regulatory polynucleotide of the invention includes the 5'-untranslated region (5'-UTR) of the FLAP cDNA, or a biologically active fragment or variant thereof.

A preferred 3'-regulatory polynucleotide of the invention includes the 3'-untranslated region (3'-UTR) of the FLAP cDNA, or a biologically active fragment or variant thereof.

A further object of the invention consists of an isolated, purified or recombined polynucleotide comprising:

a) a nucleic acid comprising a regulatory nucleotide sequence selected from the group consisting of:

(i) a polynucleotide beginning at position 1 and ending at position 7708 of SEQ ID No 1, more preferably beginning at position 1 and ending at position 7007 of SEQ ID No 1, or a sequence complementary thereto;

(ii) a polynucleotide having at least 95% of nucleotide identity with the nucleotide sequence beginning at position 1 and ending at position 7708 of SEQ ID No 1, more preferably beginning at position 1 and ending at position 7007 of SEQ ID No 1, or a sequence complementary thereto;

(iii) a polynucleotide that hybridizes under stringent hybridization conditions with the nucleotide sequence beginning at position 1 and ending at position 7007 of SEQ ID No 1, or a sequence complementary thereto;

(iv) a biologically active fragment or variant of the polynucleotides in (i), (ii) and (iii);

b) a polynucleotide encoding a desired polypeptide or a nucleic acid of interest, operably linked to the nucleic acid defined in (a) above;

c) Optionally, a nucleic acid comprising a 3'-regulatory polynucleotide, preferably a 3'-regulatory polynucleotide of the FLAP gene.

In a specific embodiment of the nucleic acid defined above, said nucleic acid includes the 5'-untranslated region (5'-UTR) of the FLAP cDNA, or a biologically active fragment or variant thereof.

In a second specific embodiment of the nucleic acid defined above, said nucleic acid includes the 3'-untranslated region (3'-UTR) of the FLAP cDNA, or a biologically active fragment or variant thereof.

The regulatory sequences may comprise a biallelic marker selected from the group consisting of A1 to A11 and A22 to A28, and the complements thereof.

The polypeptide encoded by the nucleic acid described above may be of various nature or origin, encompassing proteins of prokaryotic or eukaryotic origin. Among the polypeptides expressed under the control of a FLAP regulatory region, there may be cited bacterial, fungal or viral antigens. Also encompassed are eukaryotic proteins such as intracellular proteins, for example "house keeping" proteins, membrane-bound proteins, for example receptors, and secreted proteins, for example cytokines. In a specific embodiment, the desired polypeptide may be the FLAP protein, especially the protein of the amino acid sequence of SEQ ID No 3.

The desired nucleic acids encoded by the above described polynucleotide, usually a RNA molecule, may be complementary to a desired coding polynucleotide, for example to the FLAP coding sequence, and thus useful as an antisense polynucleotide.

Such a polynucleotide may be included in a recombinant expression vector in order to express the desired polypeptide or the desired nucleic acid in host cell or in a host organism.

III. FLAP cDNA Sequences

The present invention provides a FLAP cDNA of SEQ ID No 2. The cDNA of SEQ ID No 2 also includes a 5'-UTR region and a 3'-UTR region. The 5'-UTR region starts at the nucleotide at position 1 and ends at the nucleotide in position 74 of SEQ ID No 2. The 3'-UTR region starts at the nucleotide at position 561 and ends at the nucleotide at position 875 of SEQ ID No 2. The polyadenylation site starts at the nucleotide at position 851 and ends at the nucleotide in position 856 of SEQ ID No 2.

Consequently, the invention concerns a purified, isolated, and recombinant nucleic acids comprising a nucleotide sequence of the 5'-UTR and the 3'UTR of the FLAP cDNA, a sequence complementary thereto, or an allelic variant thereof.

Another object of the invention is a purified, isolated, or recombinant nucleic acid comprising the nucleotide sequence of SEQ ID No 2, complementary sequences thereto or a variant or fragment thereof. Moreover, preferred polynucleotides of the invention include purified, isolated, or recombinant FLAP cDNAs consisting of, consisting essentially of, or comprising the sequence of SEQ ID No 2. A particular preferred embodiment of the invention includes isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or a complementary sequence thereto, wherein said contiguous span comprises a T at position 197 (A13), an A at position 453 (A20), or a G at position 779 (A21) of SEQ ID No 2.

Most biallelic polymorphisms represent silent nucleotide substitutions but biallelic marker A20 is associated with amino acid changes from valine to isoleucine in position 127 in the corresponding FLAP polypeptide.

The polynucleotide disclosed above that contains the coding sequence of the FLAP gene of the invention may be expressed in a desired host cell or a desired host organism, when this polynucleotide is placed under the control of suitable expression signals. The expression signals may be either the expression signals contained in the regulatory regions in the FLAP gene of the invention or may be exogenous regulatory nucleic sequences. Such a polynucleotide, when placed under the suitable expression signals, may also be inserted in a vector for its expression.

While this section is entitled "FLAP cDNA Sequences," it should be noted that nucleic acid fragments of any size and sequence may also be comprised by the polynucleotides described in this section, flanking the genomic sequences of FLAP on either side or between two or more such genomic sequences.

Coding Regions

The FLAP open reading frame is contained in the corresponding mRNA of SEQ ID No 2. More precisely, the effective FLAP coding sequence (CDS) spans from the nucleotide in position 75 (first nucleotide of the ATG codon) to the nucleotide in position 560 (end nucleotide of the TGA codon) of the polynucleotide sequence of SEQ ID No 2. The present invention also embodies isolated, purified, and recombinant polynucleotides which encode a polypeptide comprising a contiguous span of at least 6 amino acids, preferably at least 8 or 10 amino acids, more preferably at least 12, 15, 20, 25, 30, 40, 50, or 100 amino acids of SEQ ID No 3, wherein said contiguous span includes a isoleucine residue at amino acid position 127 in SEQ ID No 3.

The above disclosed polynucleotide that contains the coding sequence of the FLAP gene may be expressed in a desired host cell or a desired host organism, when this polynucleotide is placed under the control of suitable expression signals. The expression signals may be either the expression signals contained in the regulatory regions in the FLAP gene of the invention or in contrast the signals may be exogenous regulatory nucleic sequences. Such a polynucleotide, when placed under the suitable expression signals, may also be inserted in a vector for its expression and/or amplification.

IV. Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial FLAP Gene Expression in Recombinant Cell Hosts and in Transgenic Animals.

In order to study the physiological and phenotypic consequences of a lack of synthesis of the FLAP protein, both at the cell level and at the multi cellular organism level, the invention also encompasses DNA constructs and recombinant vectors enabling a conditional expression of a specific allele of the FLAP genomic sequence or cDNA and also of a copy of this genomic sequence or cDNA harboring substitutions, deletions, or additions of one or more bases as regards to the FLAP nucleotide sequence of SEQ ID Nos 1 and 2, or a fragment thereof, these base substitutions, deletions or additions being located either in an exon, an intron or a regulatory sequence, but preferably in the 5'-regulatory sequence or in an exon of the FLAP genomic sequence or within the FLAP cDNA of SEQ ID No 2. In a preferred embodiment, the FLAP sequence comprises a biallelic marker of the present invention, preferably one of the biallelic markers A1 to A28.

The present invention embodies recombinant vectors comprising any one of the polynucleotides described in the present invention.

A first preferred DNA construct is based on the tetracycline resistance operon tet from *E. coli* transposon Tn110 for controlling the FLAP gene expression, such as described by Gossen et al. (1992, 1995) and Furth et al. (1994). Such a DNA construct contains seven tet operator sequences from Tn10 (tetop) that are fused to either a minimal promoter or a 5'-regulatory sequence of the FLAP gene, said minimal promoter or said FLAP regulatory sequence being operably linked to a polynucleotide of interest that codes either for a sense or an antisense oligonucleotide or for a polypeptide, including a FLAP polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the FLAP genomic sequence; (b) a nucleotide sequence comprising a positive selection marker, such as the marker for neomycine resistance (neo); and (c) a second nucleotide sequence that is comprised in the FLAP genomic sequence, and is located on the genome downstream the first FLAP nucleotide sequence (a).

In a preferred embodiment, this DNA construct also comprises a negative selection marker located upstream the nucleotide sequence (a) or downstream the nucleotide sequence (c). Preferably, the negative selection marker consists of the thymidine kinase (tk) gene (Thomas et al., 1986), the hygromycine beta gene (Te Riele et al., 1990), the hprt gene (Van der Lugt et al., 1991; Reid et al., 1990) or the Diphteria toxin A fragment (Dt-A) gene (Nada et al., 1993; Yagi et al. 1990). Preferably, the positive selection marker is located within a FLAP exon sequence so as to interrupt the sequence encoding a FLAP protein. These replacement vectors are described, for example, by Thomas et al. (1986; 1987), Mansour et al. (1988) and Koller et al. (1992).

The first and second nucleotide sequences (a) and (c) may be indifferently located within a FLAP regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the FLAP gene by homologous recombination is constructed in such a way that selectable markers are flanked by loxP sites of the same orientation, it is possible, by treatment by the Cre enzyme, to eliminate the selectable markers while leaving the FLAP sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the FLAP genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the FLAP genomic sequence, and is located on the genome downstream of the first FLAP nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may be the result of the breeding of two transgenic animals, the first transgenic animal bearing the FLAP-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a FLAP genomic sequence or a FLAP cDNA sequence, and most preferably an altered copy of a FLAP genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a FLAP genomic sequence or a FLAP cDNA sequence comprising at least one biallelic marker of the present invention, preferably at least one biallelic marker selected from the group consisting of A1 to A28 and the complements thereof, more preferably at least one biallelic marker selected from the group consisting of A1 to A13, A15, and A17 to A28 and the complements thereof.

Nuclear Antisense DNA Constructs

Other compositions containing a vector of the invention comprise an oligonucleotide fragment of the nucleic sequence SEQ ID No 2 comprising a biallelic marker of the invention, preferably a fragment including the start codon of the FLAP gene, as an antisense tool that inhibits the expression of the corresponding FLAP gene. Preferred methods using antisense polynucleotide according to the present invention are the procedures described by Sczakiel et al. (1995) or those described in PCT Application No WO 95/24223.

Preferably, the antisense tools are chosen among the polynucleotides (15-200 bp long) that are complementary to the 5'end of the FLAP mRNA. In one embodiment, a combination of different antisense polynucleotides complementary to different parts of the desired targeted gene are used.

Preferred antisense polynucleotides according to the present invention are complementary to a sequence of the mRNAs of FLAP that contains either the translation initiation codon ATG or a splicing site. Further preferred antisense polynucleotides according to the invention are complementary of the splicing site of the FLAP mRNA.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these FLAP antisense polynucleotides also comprise, within the ribozyme cassette, a histone stem-loop structure to stabilize cleaved transcripts against 3'-5' exonucleolytic degradation, such as the structure described by Eckner et al. (1991).

V. Biallelic Markers of the FLAP Gene

The invention also concerns FLAP-related biallelic markers, preferably a biallelic marker associated with a disease involving the leukotriene pathway, most preferably asthma. The term FLAP-related biallelic marker includes the biallelic markers designated A1 to A28. The invention also concerns sets of these biallelic markers.

28 biallelic markers have been identified in the genomic sequence of FLAP. These biallelic markers are disclosed in Table 2 of Example 3. Their location on the FLAP genomic sequence and cDNA is indicated in Table 2 and also as a single base polymorphism in the features of SEQ ID No 1. Table 2 also discloses the position in SEQ ID No 1 of polynucleotides of 47 nucleotides in length, designated P1 to P28, which comprise a biallelic marker of the FLAP gene and define said biallelic marker. The pairs of primers allowing the amplification of a nucleic acid containing the polymorphic base of one FLAP biallelic marker are listed in Table 1 of Example 2. Three biallelic markers, namely A13, A20 and A21, are located in exonic regions. Two of them do not modify the amino acid sequence of the FLAP protein. However, the biallelic marker A20 changes a valine into a isoleucine in the FLAP protein.

The invention also relates to a purified and/or isolated nucleotide sequence comprising a polymorphic base of a biallelic marker located in the sequence of the FLAP gene, preferably of a biallelic marker selected from the group consisting of A1 to A28, preferably from the group consisting of A1 to A13, A15, and A17 to A28, and the complements thereof; optionally, said biallelic marker is selected from the group consisting of A1 to A10 and A22 to A28; optionally, said biallelic marker is selected from the group consisting of A11 to A13, A15, A17 to A21; optionally, said biallelic marker is either A14 or A16. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides of a nucleotide sequence selected from the group consisting of SEQ ID Nos 1 and 2 or a variant thereof or a complementary sequence thereto. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide. Optionally, the 3' end of said contiguous span may be present at the 3' end of said polynucleotide. Optionally, the biallelic marker may be present at the 3' end of said polynucleotide. Optionally, the 3' end of said polynucleotide may be located within or at least 2, 4, 6, 8, 10, 12, 15, 18, 20, 25, 50, 100, 250, 500, or 1000 nucleotides upstream of a biallelic marker of the FLAP gene in said sequence. Optionally, the 3' end of said polynucleotide may be located 1 nucleotide upstream of a biallelic marker of the FLAP gene in said sequence. Optionally, said polynucleotide may further comprise a label. Optionally, said polynucleotide can be attached to solid support. In a further embodiment, the polynucleotides defined above can be used alone or in any combination.

The invention further concerns a nucleic acid encoding the FLAP protein, wherein said nucleic acid comprises a polymorphic base of a biallelic marker selected from the group consisting of A1 to A28 and the complements thereof, preferably from the group consisting of A1 to A13, A15, and A17 to A28 and the complements thereof.

The invention also relates to a nucleotide sequence, preferably a purified and/or isolated nucleotide sequence comprising a sequence defining a biallelic marker of the FLAP gene, a fragment or variant thereof or a sequence complementary thereto, said fragment comprising the polymorphic base. Preferably, the sequences defining a biallelic marker include the polymorphic base of one of the polynucleotides P1 to P13, P15 and P17 to P28 or the complements thereof. In some embodiments, the sequences defining a biallelic marker comprise a nucleotide sequence selected from the group consisting of P1 to P13, P15 and P17 to P28, and the complementary sequence thereto or a fragment thereof, said fragment comprising the polymorphic base.

The invention also concerns a set of the purified and/or isolated nucleotide sequences defined above. More particularly, the set of purified and/or isolated nucleotide sequences comprises a group of sequences defining a combination of biallelic markers of the FLAP gene. Preferably, the combination of alleles of biallelic markers is associated with asthma.

In a preferred embodiment, the invention relates to a set of purified and/or isolated nucleotide sequences, each sequence comprising a sequence defining a biallelic marker of the FLAP gene, wherein the set is characterized in that between about 30 and 100%, preferably between about 40 and 60%, more preferably between 50 and 60%, of the sequences defining a biallelic marker are selected from the group consisting of P1 to P28, preferably of P1 to P13, P15 and P17 to P28, or a fragment or variant thereof or the complementary sequence thereto, said fragment comprising the polymorphic base.

More particularly, the invention concerns a set of purified and/or isolated nucleotide sequences, each sequence comprising a sequence defining a different biallelic marker of the FLAP gene, said biallelic marker being either included in a nucleotide sequence selected from the group consisting of P1 to P28 and the complementary sequence thereto, preferably of P1 to P13, P15 and P17 to P28 and the complementary sequence thereto, or a biallelic marker, preferably one located in the sequence of the FLAP gene, biallelic markers A1 to A28, or markers in linkage disequilibrium with one of the markers of the set defined herewith.

The invention also relates to a set of at least two, preferably four, five, six, seven, eight or more nucleotide sequences selected from the group consisting of P1 to P28, preferably of P1 to P13, P15 and P17 to P28, and the complementary sequence thereto, or a fragment or variant thereof, said fragment comprising the polymorphic base. Preferably, this set comprises at least one nucleotide sequence defining a biallelic marker for each linkage disequilibrium region of the FLAP gene.

The invention further concerns a nucleotide sequence selected from the group consisting of P1 to P13, P15 and P17 to P28, or a complementary sequence thereto or a fragment or a variant thereof, said fragment comprising the polymorphic base.

In a further embodiment, the sequences comprising a polymorphic base of one of the biallelic markers listed in Table 2 are selected from the group consisting of the nucleotide sequences that have a contiguous span of, that consist of, that are comprised in, or that comprises a polynucleotide selected from the group consisting of the nucleic acids of the sequences set forth as Nos. 10-517, 10-518, 10-253, 10-499, 10-500, 10-522, 10-503, 10-504, 10-204, 10-32, 10-33, 10-34, 10-35, 10-36, 10-498, 12-628, and 12-629 (listed in Table 1) or a variant thereof or a complementary sequence thereto.

VI. Oligonucleotide Probes and Primers

Polynucleotides derived from the FLAP gene are useful in order to detect the presence of at least a copy of a nucleotide sequence of SEQ ID No 1 or 2, or a fragment or a variant thereof in a test sample.

Particularly preferred probes and primers comprise a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises at least 1, 2, 3, 5, or 10 of the following nucleotide positions of SEQ ID No 1: 1-7007, 8117-15994, 16550-24058, 24598-27872, 28413-35976, and 36927-43069. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises a C at position 16348, of SEQ ID No 1. Further preferred nucleic acids of the invention include isolated, purified, or recombinant polynucleotides comprising a contiguous span of at least 26, 30, 35, 40, 50, 60, 70, 80, 90, 100, 150, 200, 500, or 1000 nucleotides of SEQ ID No 1 or the complementary sequence thereof, wherein said contiguous span comprises of the following nucleotide positions of SEQ ID No 1: 7612-7637, 24060-24061, 24067-24068, 27903-27905, and 28327-28329. Additional preferred probes and primers comprise a contiguous span of at least 12, 15, 18, 20, 25, 30, 35, 40, 50, 60, 70, 80, 90, 100, 150, 200, 500, or 1000 nucleotides of SEQ ID No 1 or the complementary sequence thereof, wherein said contiguous span comprises a nucleotide selected from the group consisting of an A at position 7445, an A at position 7870, a T at position 16288, an A at position 16383, a T at position 24361, a G at position 28336, a T at position 28368, an A at position 36183, and a G at position 36509 of SEQ ID No 1.

Thus, the invention also relates to nucleic acid probes or primers characterized in that they hybridize specifically, under the stringent hybridization conditions defined above, with a nucleic acid selected from the group consisting of the nucleotide sequences 1-7007, 8117-15994, 16550-24058, 24598-27872, 28413-35976, and 36927-43069 of SEQ ID No 1 or a variant thereof or a sequence complementary thereto.

Particularly preferred probes and primers comprise a contiguous span of at least 12, 15, 18, 20, 25, 30, 35, 40, 50, 60, 70, 80, 90, 100, 150, 200, 500, or 1000 nucleotides of SEQ ID No 2 or a complementary sequence thereto, wherein said contiguous span comprises a T at position 197 (A13), an A at position 453 (A20), or a G at position 779 (A21) of SEQ ID No 2.

The present invention also concerns oligonucleotides and groups of oligonucleotides for the detection of alleles associated with a modified leukotriene metabolism, preferably alleles associated with a FLAP gene polymorphism, and more preferably alleles of a FLAP gene associated with a disease involving the leukotriene pathway, for example asthma. These oligonucleotides are characterized in that they can hybridize with a FLAP gene, preferably with a polymorphic FLAP gene and more preferably with a region of a FLAP gene comprising the polymorphic site of which specific alleles are associated with a disease involving the leukotriene pathway such as asthma. The oligonucleotides are useful either as primers for use in various processes such as DNA amplification and microsequencing or as probes for DNA recognition in hybridization analyses. In some embodiments, the oligonucleotides contain the polymorphic base of a sequence selected from the group consisting of P1 to P28 and the complementary sequence thereto, more preferably from the group consisting of P1 to P13, P15, P17 to P28 and the complementary sequence thereto. In other embodiments, the oligonucleotides have a 3' terminus immediately adjacent to a polymorphic base in the FLAP gene, such as a polymorphic base in one of P1 to P28 and the complementary sequence thereto, optionally of P1 to P13, P15, and P17 to P28 and the complementary sequence thereto. In other embodiments, the oligonucleotide is capable of discriminating between different alleles of a biallelic marker in the FLAP gene, said biallelic marker being selected from the group consisting of A1 to A28 and the complements thereof, optionally of A1 to A13, A15, and A17 to A28 and the complements thereof. For example, the oligonucleotide may be capable of specifically hybridizing to one allele of a biallelic marker, including one of the biallelic markers A1 to A28 and the complements thereof, optionally of A1 to A13, A15, and A17 to A28 and the complements thereof. In another embodiment, the oligonucleotides comprise one of the sequences of B1 to B17, C1 to C17, D1 to D28, E1 to E28, and P1 to P28, and the complementary sequence thereto. Optionally, the oligonucleotides comprise one of the sequences of B1 to B17, C1 to C17, D1 to D13, D15, D17 to D28, E1 to E13, E15, E17 to E28, P1 to P13, P15, and P17 to P28, and the complementary sequence thereto.

In one embodiment the invention encompasses isolated, purified, and recombinant polynucleotides consisting of, or consisting essentially of a contiguous span of 8 to 50 nucleotides of SEQ ID No 1 or 2 and the complement thereof, wherein said span includes a FLAP-related biallelic marker in said sequence; optionally, wherein said FLAP-related biallelic marker is selected from the group consisting of A1 to A28, and the complements thereof, or optionally the biallelic markers in linkage disequilibrium therewith; optionally, wherein said FLAP-related biallelic marker is selected from the group consisting of A1 to A13, A15, A17 to A28, and the complements thereof, or optionally the biallelic markers in linkage disequilibrium therewith; optionally, wherein said FLAP-related biallelic marker is selected from the group consisting of A1 to A10 and A22 to A28, and the complements thereof, or optionally the biallelic markers in linkage disequilibrium therewith; optionally, wherein said FLAP-related biallelic marker is selected from the group consisting of A11 to A13, A15, A17 to A21, and the complements thereof, or optionally the biallelic markers in linkage disequilibrium therewith; optionally, wherein said FLAP-related biallelic marker is selected from the group consisting of A14 and A16, and the complements thereof, or optionally the biallelic markers in linkage disequilibrium therewith; optionally, wherein said contiguous span is 18 to 47 nucleotides in length and said biallelic marker is within 6, 5, 4, 3, 2, or 1 nucleotides of the center of the polynucleotide and preferably within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide.

In another embodiment the invention encompasses isolated, purified and recombinant polynucleotides consisting of, or consisting essentially of a contiguous span of 8 to 50 nucleotides of SEQ ID No 1 or 2 or the complement thereof, wherein the 3' end of said contiguous span is located at the 3' end of said polynucleotide. In one embodiment, the 3' end of said polynucleotide is located within or at least 2, 4, 6, 8, 10, 12, 15, 18, 20, 25, 50, 100, 250, 500, or 1000 nucleotides upstream of a biallelic marker of FLAP in said sequence or at any other location which is appropriate for their intended use in sequencing, amplification or the location of novel sequences or markers. In a particular embodiment, the 3' end of said polynucleotide is located within 20 nucleotides upstream of a FLAP-related biallelic marker in said sequence; optionally, wherein said FLAP-related biallelic marker is selected from the group consisting of A1 to A28, and the complements thereof, or optionally the biallelic markers in linkage disequilibrium therewith; optionally, wherein said FLAP-related biallelic marker is selected from the group consisting of A1 to A13, A15, A17 to A28, and the complements thereof, or optionally the biallelic markers in linkage disequilibrium therewith; optionally, wherein said FLAP-related biallelic marker is selected from the group consisting of A1 to A10 and A22 to A28, and the complements thereof, or optionally the biallelic markers in linkage disequilibrium therewith; optionally, wherein said FLAP-related biallelic marker is selected from the group consisting of A11 to A13, A15, A17 to A21, and the complements thereof, or optionally the biallelic markers in linkage disequilibrium therewith; optionally, wherein said FLAP-related biallelic marker is either A14 or A16, and the complements thereof, or optionally the biallelic markers in linkage disequilibrium therewith; optionally, wherein the 3' end of said polynucleotide is located 1 nucleotide upstream of said FLAP-related biallelic marker in said sequence; and optionally, wherein said polynucleotide consists essentially of a sequence selected from the following sequences: D1 to D28 and E1 to E28; and optionally, wherein said polynucleotide consists essentially of a sequence selected from the following sequences: D1 to D13, D15, D17 to D28, E1 to E13, E15, and E17 to E28. In a further embodiment, the invention encompasses isolated, purified, or recombinant polynucleotides consisting of, or consisting essentially of a sequence selected from the following sequences: B1 to B17, and C1 to C17. To these primers can be added, at either end thereof, a further polynucleotide useful for sequencing. Preferably, primers PU contain the additional PU 5' sequence of SEQ ID No 14 and primers RP contain the RP 5' sequence of SEQ ID No 15.

In an additional embodiment, the invention encompasses polynucleotides for use in hybridization assay sequencing assays, microsequencing assays and enzyme-based mismatch detection assays for determining the identity of the nucleotide at a FLAP-related biallelic marker in SEQ ID No 1 or 2, or the complement thereof, as well as polynucleotides for use in amplifying segments of nucleotides comprising a FLAP-related biallelic marker in SEQ ID No 1 or 2, or the complement thereof; optionally, wherein said FLAP-related biallelic marker is selected from the group consisting of A1 to A28, and the complements thereof, or optionally the biallelic markers in linkage disequilibrium therewith; optionally from the group consisting of A1 to A13, A15, and A17 to A28, and the complements thereof, or optionally the biallelic markers in linkage disequilibrium therewith; optionally from the group consisting of A1 to A10 and A22 to A28, and the complements thereof, or optionally the biallelic markers in linkage disequilibrium therewith; optionally from the group consisting of A11 to A13, A15, A17 to A21, and the complements thereof, or optionally the biallelic markers in linkage disequilibrium therewith; optionally from the group consisting of A14 and A16, and the complements thereof, or optionally the biallelic markers in linkage disequilibrium therewith. Optionally, said polynucleotide may comprise a sequence disclosed in the present specification; Optionally, said polynucleotide may consist of, or consist essentially of any polynucleotide described in the present specification. A preferred polynucleotide may be used in a hybridization assay for determining the identity of the nucleotide at a biallelic marker of the FLAP gene. Another preferred polynucleotide may be used in a sequencing or microsequencing assay for determining the identity of the nucleotide at a biallelic marker of the FLAP gene. A third preferred polynucleotide may be used in an enzyme-based mismatch detection assay for determining the identity of the nucleotide at a biallelic marker of the FLAP gene. A fourth preferred polynucleotide may be used in amplifying a segment of polynucleotides comprising a biallelic marker of the FLAP gene; Optionally, said amplifying may be performed by a PCR or LCR. Optionally, said polynucleotide may be attached to a solid support, array, or addressable array; Optionally, said polynucleotide may be labeled.

Primers and probes according to the invention are therefore synthesized to be "substantially" complementary to a strand of the FLAP gene to be amplified. The primer sequence does not need to reflect the exact sequence of the DNA template. Minor mismatches can be accommodated by reducing the stringency of the hybridization conditions. Among the various methods available to design useful primers, the OSP computer software can be used by the skilled person (see Hillier & Green, 1991).

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the primers and probes of the invention usually ranges between 10 and 75%, preferably between 35 and 60%, and more preferably between 40 and 55%.

Preferably, the length of the primer and probe can range from 10 to 100 nucleotides, preferably from 10 to 50, 10 to 30 or more preferably 10 to 25 nucleotides. Shorter primers and probes tend to lack specificity for a target nucleic acid sequence and generally require cooler temperatures to form sufficiently stable hybrid complexes with the template. Longer primers and probes are expensive to produce and can sometimes self-hybridize to form hairpin structures. The appropriate length for primers and probes under a particular set of assay conditions may be empirically determined by one of skill in the art.

The probes of the present invention are useful for a number of purposes. They can be used in Southern hybridization to genomic DNA or Northern hybridization to mRNA. The probes can also be used to detect PCR amplification products. They may also be used to detect mismatches in the FLAP gene or mRNA using other techniques. Generally, the probes are complementary to the FLAP gene coding sequences, although probes to introns and regulatory sequences are also contemplated.

Primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592. The disclosures of all these documents are incorporated herein by reference.

Detection probes are generally nucleic acid sequences or uncharged nucleic acid analogs such as, for example peptide nucleic acids which are disclosed in International Patent Application WO 92/20702; morpholino analogs which are described in U.S. Pat. Nos. 5,185,444, 5,034,506, and 5,142, 047; and the like. The disclosures of each of these patents is incorporated herein by reference. Depending upon the type of label carried by the probe, the probe is employed to capture or detect the amplicon generated by the amplification reaction. The probe is not involved in amplification of the target sequence and therefore may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No 07/049,061 filed Apr. 19, 1993 describes modifications which can be used render a probe non-extendable.

The probes are preferably directly labeled such as with isotopes, reporter molecules or fluorescent labels or indirectly labeled such as with biotin to which a streptavidin complex may later bind. Probe labeling techniques are well-known to the skilled technician. By assaying the presence of the probe, one can detect the presence or absence of the targeted DNA sequence in a given sample. The same labels can be used with primers. For example, useful labels include radioactive substances ($^{32}$P, $^{35}$S, $^{3}$H, $^{125}$I), fluorescent dyes (5-bromodesoxyuridin, fluorescein, acetylaminofluorene, digoxigenin). Preferably, polynucleotides are labeled at their 3' and 5' ends. Examples of non-radioactive labeling of nucleic acid fragments are described in the French patent No FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in the European patent No EP 0 225 807 (Chiron).

Any of the primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The "solid phase" is not critical and can be selected by one skilled in the art. Thus, latex particles, microparticies, magnetic or non-magnetic beads, membranes, plastic tubes, walls of microtiter wells, glass or silicon chips, sheep (or other suitable animal's) red blood cells and duracytes are all suitable examples.

Suitable methods for immobilizing nucleic acids on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent.

Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent.

As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes and other configurations known to those of ordinary skill in the art.

The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also deals with a method for detecting the presence of a nucleic acid comprising a nucleotide sequence selected from a group consisting of SEQ ID Nos 1 and 2, a fragment or a variant thereof or a complementary sequence thereto in a sample, said method comprising the following steps of:
 a) bringing into contact a nucleic acid probe or a plurality of nucleic acid probes which can hybridize with a nucleotide sequence included in a nucleic acid selected form the group consisting of the nucleotide sequences of SEQ ID Nos 1 and 2, a fragment or a variant thereof or a complementary sequence thereto and the sample to be assayed.
 b) detecting the hybrid complex formed between the probe and a nucleic acid in the sample.

The invention further concerns a kit for detecting the presence of a nucleic acid comprising a nucleotide sequence selected from a group consisting of SEQ ID Nos 1 and 2, a fragment or a variant thereof or a complementary sequence thereto in a sample, said kit comprising:
 a) a nucleic acid probe or a plurality of nucleic acid probes which can hybridize with a nucleotide sequence included in a nucleic acid selected form the group consisting of the nucleotide sequences of SEQ ID Nos 1 and 2, a fragment or a variant thereof or a complementary sequence thereto;
 b) optionally, the reagents necessary for performing the hybridization reaction.

In a first preferred embodiment of the detection method and kit, the nucleic acid probe or the plurality of nucleic acid probes are labeled with a detectable molecule. In a second preferred embodiment of the detection method and kit, the nucleic acid probe or the plurality of nucleic acid probes has been immobilized on a substrate. In a third preferred embodiment of the detection method and kit, the nucleic acid probe or the plurality of nucleic acid probes comprise either a sequence which is selected from the group consisting of the nucleotide sequences: B1 to B17, C1 to C17, D1 to D28, E1 to E28, P1 to P28 or a biallelic marker selected from the group consisting of A1 to A28 or the complements thereto or the biallelic markers in linkage disequilibrium therewith.

Oligonucleotide Arrays

A substrate comprising a plurality of oligonucleotide primers or probes of the invention may be used either for detecting or amplifying targeted sequences in the FLAP gene and may also be used for detecting mutations in the coding or in the non-coding sequences of the FLAP gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the FLAP gene. For this particular purpose, probes are specifically designed to have a nucleotide sequence allowing their hybridization to the genes that carry known mutations (either by deletion, insertion or substitution of one or several nucleotides). By known mutations, it is meant, mutations on the FLAP gene that have been identified according, for example to the technique used by Huang et al. (1996) or Samson et al. (1996).

Another technique that is used to detect mutations in the FLAP gene is the use of a high-density DNA array. Each oligonucleotide probe constituting a unit element of the high density DNA array is designed to match a specific subsequence of the FLAP genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the FLAP gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996, which is herein incorporated by reference.

Consequently, the invention concerns an array of nucleic acid molecules comprising at least one polynucleotide described above as probes and primers. Preferably, the invention concerns an array of nucleic acid comprising at least two polynucleotides described above as probes and primers.

A further object of the invention consists of an array of nucleic acid sequences comprising either at least one of the sequences selected from the group consisting of P1 to P28, B1 to B17, C1 to C17, D1 to D28 and E1 to E28 or the sequences complementary thereto or a fragment thereof of at least 8, 10, 12, 15, 18, 20, 25, 30, or 40 consecutive nucleotides thereof, or at least one sequence comprising a biallelic marker selected from the group consisting of A1 to A28, and the complements thereto, or optionally the biallelic markers in linkage disequilibrium therewith.

The invention also pertains to an array of nucleic acid sequences comprising either at least two of the sequences selected from the group consisting of P1 to P28, B1 to B17, C1 to C17, D1 to D28 and E1 to E28 or the sequences complementary thereto or a fragment thereof of at least 8 consecutive nucleotides thereof, or at least two sequences comprising a biallelic marker selected from the group consisting of A1 to A28, and the complements thereto, or optionally the biallelic markers in linkage disequilibrium therewith.

VII. Identification of Biallelic Markers

There are two preferred methods through which the biallelic markers of the present invention can be generated. In a first method, DNA samples from unrelated individuals are pooled together, following which the genomic DNA of interest is amplified and sequenced. The nucleotide sequences thus obtained are then analyzed to identify significant polymorphisms.

One of the major advantages of this method resides in the fact that the pooling of the DNA samples substantially reduces the number of DNA amplification reactions and sequencing reactions which must be carried out. Moreover, this method is sufficiently sensitive so that a biallelic marker obtained therewith usually shows a sufficient degree of informativeness for conducting association studies.

In a second method for generating biallelic markers, the DNA samples are not pooled and are therefore amplified and sequenced individually. The resulting nucleotide sequences obtained are then also analyzed to identify significant polymorphisms.

It will readily be appreciated that when this second method is used, a substantially higher number of DNA amplification reactions and sequencing reactions must be carried out. Moreover, a biallelic marker obtained using this method may show a lower degree of informativeness for conducting association studies, e.g. if the frequency of its less frequent allele may be less than about 10%. It will further be appreciated that including such less informative biallelic markers in association studies to identify potential genetic associations with a trait may allow in some cases the direct identification of causal mutations, which may, depending on their penetrance, be rare mutations. This method is usually preferred when biallelic markers need to be identified in order to perform association studies within candidate genes.

The following is a description of the various parameters of a preferred method used by the inventors to generate the markers of the present invention.

1. DNA Extraction

The genomic DNA samples from which the biallelic markers of the present invention are generated are preferably obtained from unrelated individuals corresponding to a heterogeneous population of known ethnic background.

The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the skilled technician. Details of a preferred embodiment are provided in Example 1.

Once genomic DNA from every individual in the given population has been extracted, it is preferred that a fraction of each DNA sample is separated, after which a pool of DNA is constituted by assembling equivalent amounts of the separated fractions into a single one. However, the person skilled in the art can choose to amplify the pooled or unpooled sequences 2. DNA Amplification The identification of biallelic markers in a sample of genomic DNA may be facilitated through the use of DNA amplification methods. DNA samples can be pooled or unpooled for the amplification step.

DNA amplification techniques are well-known to those skilled in the art. Amplification techniques that can be used in the context of the present invention include, but are not limited to, the ligase chain reaction (LCR) described in EP-A-320 308, WO 9320227 and EP-A-439 182, the disclosures of which are incorporated herein by reference, the polymerase chain reaction (PCR, RT-PCR) and techniques such as the nucleic acid sequence based amplification (NASBA) described in Guatelli J. C., et al. (1990) and in Compton J. (1991), Q-beta amplification as described in European Patent Application No 4544610, strand displacement amplification as described in Walker et al. (1996) and EP A 684 315 and, target mediated amplification as described in PCT Publication WO 9322461, the disclosures of which are incorporated herein by reference.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al. (1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference.

The PCR technology is the preferred amplification technique used to identify new biallelic markers. A typical example of a PCR reaction suitable for the purposes of the present invention is provided in Example 2.

One of the aspects of the present invention is a method for the amplification of the human FLAP gene, particularly of the genomic sequence of SEQ ID No 1 or of the cDNA sequence of SEQ ID No 2, or a fragment or a variant thereof in a test sample, preferably using the PCR technology. This method comprises the steps of contacting a test sample suspected of containing the target FLAP encoding sequence or portion thereof with amplification reaction reagents comprising a pair of amplification primers, and eventually in some instances a detection probe that can hybridize with an internal region of amplicon sequences to confirm that the desired amplification reaction has taken place.

Thus, the present invention also relates to a method for the amplification of a human FLAP gene sequence, particularly of a portion of the genomic sequences of SEQ ID No 1 or of the cDNA sequence of SEQ ID No 2, or a variant thereof in a test sample, said method comprising the steps of:

a) contacting a test sample suspected of containing the targeted FLAP gene sequence comprised in a nucleotide sequence selected from a group consisting of SEQ ID Nos 1 and 2, or fragments or variants thereof with amplification reaction reagents comprising a pair of amplification primers as described above and located on either side of the polynucleotide region to be amplified, and b) optionally, detecting the amplification products.

The invention also concerns a kit for the amplification of a human FLAP gene sequence, particularly of a portion of the genomic sequence of SEQ ID No 1 or of the cDNA sequence of SEQ ID No 2, or a variant thereof in a test sample, wherein said kit comprises:

a) a pair of oligonucleotide primers located on either side of the FLAP region to be amplified;

b) optionally, the reagents necessary for performing the amplification reaction.

In one embodiment of the above amplification method and kit, the amplification product is detected by hybridization with a labeled probe having a sequence which is complementary to the amplified region. In another embodiment of the above amplification method and kit, primers comprise a sequence which is selected from the group consisting of the nucleotide sequences of B1 to B17, C1 to C17, D1 to D28 and E1 to E28. In a preferred embodiment of the above amplification method and kit, the amplification product comprises a polymorphic base of a biallelic marker of the present invention, more particularly a polymorphic base of a biallelic marker selected from the group of A1 to A28, optionally from the group consisting of A1 to A13, A15 and A17 to A28, and the complements thereof, or optionally the biallelic markers in linkage disequilibrium therewith. The primers are more particularly characterized in that they have sufficient complementarity with any sequence of a strand of the genomic sequence close to the region to be amplified, for example with a non-coding sequence adjacent to exons to amplify.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences B1 to B17 and the nucleotide sequences C1 to C17 disclosed in Example 2.

3. Sequencing of Amplified Genomic DNA and Identification of Polymorphisms

The amplification products generated as described above with the primers of the invention are then sequenced using methods known and available to the skilled technician. Preferably, the amplified DNA is subjected to automated dideoxy terminator sequencing reactions using a dye-primer cycle sequencing protocol.

Following gel image analysis and DNA sequence extraction, sequence data are automatically processed with software to assess sequence quality.

The sequence data obtained as described above are subjected to quality control and validation steps based on the shape of the peak, the inter-peak resolution, the number of unreliable peaks in a particular stretch of sequence and the noise level. Sequence data that is considered unreliable is discarded.

After this first sequence quality analysis, polymorphisms are detected among individual or pooled amplified fragment sequences. The polymorphism search is based on the presence of superimposed peaks in the electrophoresis pattern. These peaks, which present two distinct colors, correspond to two different nucleotides at the same position on the sequence. In order for peaks to be considered significant, peak height has to satisfy conditions of ratio between the peaks and conditions of ratio between a given peak and the surrounding peaks of the same color.

However, since the presence of two peaks can be an artifact due to background noise, two controls are utilized to exclude these artifacts:
- the two DNA strands are sequenced and a comparison between the peaks is carried out. The polymorphism has to be detected on both strands for validation.
- all the sequencing electrophoresis patterns of the same amplification product provided from distinct pools and/or individuals are compared. The homogeneity and the ratio of homozygous and heterozygous peak height are controlled through these distinct DNAs.

The detection limit for the frequency of biallelic polymorphisms detected by sequencing pools of 100 individuals is about 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele, preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

4. Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bonafide biallelic marker at a particular position in a sequence.

5. Evaluation of the Frequency of the Biallelic Markers of the Present Invention The validated biallelic markers are further evaluated for their usefulness as genetic markers by determining the frequency of the least common allele at the biallelic marker site. The higher the frequency of the less common allele the greater the usefulness of the biallelic marker is in association studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. For an indication of the frequency for the less common allele of a particular biallelic marker of the invention see Table 2. A biallelic marker wherein the frequency of the less common allele is 30% or more is termed a "high quality biallelic marker."

The invention also relates to methods of estimating the frequency of an allele of a FLAP-related biallelic marker in a population comprising: a) genotyping individuals from said population for said biallelic marker according to the method of the present invention; b) determining the proportional representation of said biallelic marker in said population. In addition, the methods of estimating the frequency of an allele in a population of the invention encompass methods with any further limitation described in this disclosure, or those following, specified alone or in any combination; Optionally, said FLAP-related biallelic marker may be selected from the group consisting of A1 to A28, and the complements thereof; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16, and the complements thereof, or optionally the biallelic markers in linkage disequilibrium therewith;

Optionally, determining the proportional representation of a nucleotide at a FLAP-related biallelic marker may be accomplished by determining the identity of the nucleotides for both copies of said biallelic marker present in the genome of each individual in said population and calculating the proportional representation of said nucleotide at said FLAP-related biallelic marker for the population; Optionally, determining the proportional representation may be accomplished by performing a genotyping method of the invention on a pooled biological sample derived from a representative number of individuals, or each individual, in said population, and calculating the proportional amount of said nucleotide compared with the total.

VIII. Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a FLAP biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed on nucleic acid samples derived from a single individual or pooled DNA samples.

The identification of biallelic markers described previously allows the design of appropriate oligonucleotides, which can be used as probes and primers, to amplify a FLAP gene containing the polymorphic site of interest and for the detection of such polymorphisms.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

The invention also pertains to a method of genotyping comprising determining the identity of a nucleotide at a biallelic marker of the FLAP gene in a biological sample. Optionally, the biological sample is derived from a single subject; Optionally, the identity of the nucleotides at said biallelic marker is determined for both copies of said biallelic marker present in said individual's genome. Optionally, said method is performed in vitro; Optionally, the biological sample is derived from multiple subjects. Optionally, the method of genotyping described above further comprises amplifying a portion of said sequence comprising the biallelic marker prior to said determining step; Optionally, wherein said amplifying is performed by PCR, LCR, or replication of a recombinant vector comprising an origin of replication and said portion in a host cell. The determining step of the above genotyping method may be performed either by a hybridization assay, a sequencing assay, an enzyme-based mismatch detection assay and by a microsequencing assay. Thus, the invention also encompasses methods of genotyping a biological sample comprising determining the identity of a nucleotide at a FLAP-related biallelic marker. In addition, the genotyping methods of the invention encompass methods with any further limitation described in this disclosure, or those following, specified alone or in any combination. Optionally, said biallelic marker is selected from the group consisting of A1 to A28, and the complements thereof, or optionally the biallelic markers in linkage disequilibrium therewith; optionally, said biallelic marker is selected from the group consisting of A1 to A13, A15, and A17 to A28, and the complements thereof, or optionally the biallelic markers in linkage disequilibrium therewith; optionally, said biallelic marker is selected from the group consisting of A1 to A10 and A22 to A28, and the complements thereof, or optionally the biallelic markers in linkage disequilibrium therewith; optionally, said biallelic marker is selected from the group consisting of A11 to A13, A15, A17 to A21, and the complements thereof, or optionally the biallelic markers in linkage disequilibrium therewith; optionally, said biallelic marker is either A14 or A16, and the complements thereof, or optionally the biallelic markers in linkage disequilibrium therewith.

Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "Identification of biallelic markers" VII. (2).

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. In some embodiments, the primer pair is adapted for amplifying a sequence containing the polymorphic base of one of the sequences of P1 to P28, optionally P1 to P13, P15, P17 to P28, and the complementary sequence thereto. Preferred amplification primers are listed in Example 2. It will be appreciated that the primers listed are merely exemplary and that any other set of primers which produce amplification products containing one or more biallelic markers of the present invention.

The spacing of the primers determines the length of the segment to be amplified. In the context of the present invention, amplified segments carrying biallelic markers can range in size from at least about 25 bp to 35 kbp. Amplification fragments from 25-3000 bp are typical, fragments from 50-1000 bp are preferred and fragments from 100-600 bp are highly preferred. In a preferred embodiment of the invention, the pairs of primers for amplification and sequencing are sufficiently complementary with a region of a FLAP gene located at less than 500 bp, preferably at less than 100 bp, and more preferably at less than 50 bp of a polymorphic site corresponding to one of the markers of the present invention. Amplification primers may be labeled or immobilized on a solid support as described in "Oligonucleotide probes and primers".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by a sequencing assay, an enzyme-based mismatch detection assay, or a hybridization assay. The following is a description of some preferred methods. A highly preferred method is the microsequencing technique. The term "sequencing" is used herein to refer to polymerase extension of duplex primer/template complexes and includes both traditional sequencing and microsequencing.

1) Sequencing Assays

The amplification products generated above with the primers of the invention can be sequenced using methods known and available to the skilled technician. Preferably, the amplified DNA is subjected to automated dideoxy terminator sequencing reactions using a dye-primer cycle sequencing protocol. A sequence analysis can allow the identification of the base present at the polymorphic site.

2) Microsequencing Assays

Polymorphism analyses on pools or selected individuals of a given population can be carried out by conducting microsequencing reactions on candidate regions contained in amplified fragments obtained by PCR performed on DNA or RNA samples taken from these individuals.

To do so, DNA samples are subjected to PCR amplification of the candidate regions under conditions similar to those described above. These genomic amplification products are then subjected to automated microsequencing reactions using ddNTPs (specific fluorescence for each ddNTP) and appropriate oligonucleotide microsequencing primers which can hybridize just upstream of the polymorphic base of interest. Once specifically extended at the 3' end by a DNA polymerase using a complementary fluorescent dideoxynucleotide analog (thermal cycling), the primer is precipitated to remove the unincorporated fluorescent ddNTPs. The reaction products in which fluorescent ddNTPs have been incorporated are then analyzed by electrophoresis on ABI 377 sequencing machines to determine the identity of the incorporated base, thereby identifying the polymorphic marker presnet in the sample.

An example of a typical microsequencing procedure that can be used in the context of the present invention is provided in example 4. It is to be understood that certain parameters of this procedure such as the electrophoresis method or the labeling of ddNTPs could be modified by the skilled person without substantially modifying its result.

The extended primer may also be analyzed by MALDI-TOF Mass Spectrometry. The base at the polymorphic site is identified by the mass added onto the microsequencing primer (see Haff and Smirnov, 1997).

As a further alternative to the process described above, several solid phase microsequencing reactions have been developed. The basic microsequencing protocol is the same as described previously, except that either the oligonucleotide microsequencing primers or the PCR-amplified products of the DNA fragment of interest are immobilized. For example, immobilization can be carried out via an interaction between biotinylated DNA and streptavidin-coated microtitration wells or avidin-coated polystyrene particles.

In such solid phase microsequencing reactions, incorporated ddNTPs can either be radiolabeled (see Syvänen, 1994, incorporated herein by reference) or linked to fluorescein (see Livak & Hainer, 1994, incorporated herein by reference). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible of reporter-detection couples include: ddNTP linked to dinitrophenyl (DNP) and anti-DNP alkaline phosphatase conjugate (see Harju et al., 1993, incorporated herein by reference); and biotinylated ddNTP and horseradish peroxidase-conjugated streptavidin with o-phenylenediamine as a substrate (see WO 92/15712, incorporated herein by reference).

A diagnosis kit based on fluorescein-linked ddNTP with antifluorescein antibody conjugated with alkaline phosphatase is commercialized under the name PRONTO by GamidaGen Ltd.

As yet another alternative microsequencing procedure, Nyren et al. (1993) presented a concept of solid-phase DNA sequencing that relies on the detection of DNA polymerase activity by an enzymatic luminometric inorganic pyrophosphate detection assay (ELIDA). The PCR-amplified products are biotinylated and immobilized on beads. The microsequencing primer is annealed and four aliquots of this mixture are separately incubated with DNA polymerase and one of the four different ddNTPs. After the reaction, the resulting fragments are washed and used as substrates in a primer extension reaction with all four dNTPs present. The progress of the DNA-directed polymerization reactions are monitored with the ELIDA. Incorporation of a ddNTP in the first reaction prevents the formation of pyrophosphate during the subsequent dNTP reaction. In contrast, no ddNTP incorporation in the first reaction gives extensive pyrophosphate release during the dNTP reaction and this leads to generation of light throughout the ELIDA reactions. From the ELIDA results, the first base after the primer is easily deduced.

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferably, the biallelic markers are selected from the group consisting of A1 to A28, and the complements thereof, or optionally the biallelic markers in linkage disequilibrium therewith. Optionally, the biallelic markers are selected from the group consisting of A1 to A13, A15, A17 to A28, and the complements thereof, or optionally the biallelic markers in linkage disequilibrium therewith. Preferred microsequencing primers include the nucleotide sequences: D1 to D28 and E1 to E28. Optionally, microsequencing primers include the nucleotide sequences: D1 to D13, D15, D17 to D28, E1 to E13, E15, and E17 to E28. More preferred microsequencing primers are selected from the group consisting of the nucleotide sequences: E11, D12, D13, D14, D15, D16, E18, D19, and E20. It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by allele-specific amplification assays. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a FLAP gene comprising the polymorphic base of a biallelic marker of the present invention to hybridize therewith. Such primers are able to discriminate between the two alleles of a biallelic marker.

This can be accomplished by placing the polymorphic base at the 3' end of one of the amplification primers. Such allele specific primers tend to selectively prime an amplification or sequencing reaction so long as they are used with a nucleic acid sample that contains one of the two alleles present at a biallelic marker because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "Identification Of Biallelic Markers" (2). LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

The invention also relates to a group of probes characterized in that they preferably comprise between 10 and 50 nucleotides, and in that they are sufficiently complementary to a polymorphic sequence defined by a biallelic marker located in the genomic sequence of a FLAP gene to hybridize thereto and preferably sufficiently specific to be able to discriminate the targeted sequence for only one nucleotide variation.

The length of these probes can range from 10, 15, 20, or 30 to 100 nucleotides, preferably from 10 to 50, more preferably from 40 to 50 nucleotides. A particularly preferred probe is 25 nucleotides in length. Another preferred probe is 47 nucleotides in length. It includes a central nucleotide complementary to a polymorphic site of the FLAP gene, preferably a polymorphic site corresponding to one of the biallelic markers of the present invention, and a 23 nucleotide sequence spanning on each side of the central nucleotide and substantially complementary to the nucleotide sequences of the FLAP gene spanning on each side of the polymorphic site. Optionally, the biallelic markers of the present invention comprise the polymorphic bases in the sequences of P1 to P28 and the complementary sequences thereto. Optionally, the biallelic markers of the present invention comprise the polymorphic bases in the sequences of P1 to P13, P15, and P17 to P28, and the complementary sequences thereto.

Polymorphisms can be analyzed and the frequency of corresponding alleles quantified through hybridization reactions on amplified FLAP encoding sequences. The amplification reaction can be carried out as described previously. The hybridization probes which can be conveniently used in such reactions preferably include the probes defined above as being sufficiently complementary to a polymorphic site defined by one of the biallelic markers located in the genomic sequence of a FLAP gene to hybridize thereto and sufficiently specific to be able to discriminate between the targeted allele and an allele differing by only one base.

The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

5) Hybridization to Addressable Arrays of Oligonucleotides

Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime. These DNA chips are detailed in "oligonucleotides primers and probes", section "Oligonucleotide array".

The chip technology has already been applied with success in numerous cases. For example, the screening of mutations has been undertaken in the BRCA1 gene, in *S. cerevisiae* mutant strains, and in the protease gene of HIV-1 virus (see Hacia et al., 1996; Shoemaker et al., 1996; Kozal et al., 1996, incorporated herein by reference).

At least, three companies propose chips able to detect biallelic polymorphisms: Affymetrix (GeneChip), Hyseq (HyChip and HyGnostics), and Protogene Laboratories.

One of the limitations encountered when using DNA chip technology is that hybridization of nucleic acids with the probes attached to the chip in arrays is not simply a solution-phase reaction. A possible improvement consists in using polyacrylamide gel pads isolated from one another by hydrophobic regions in which the DNA probes are covalently linked to an acrylamide matrix.

For the detection of polymorphisms, probes which contain at least a portion of one of the biallelic markers of the present invention, such as the bialielic markers of P1 to P28, optionally P1 to P13, P15, and P17 to P28, and the complementary sequences thereto, are synthesized either in situ or by conventional synthesis and immobilized on an appropriate chip using methods known to the skilled technician. The solid surface of the chip is often made of silicon or glass but it can be a polymeric membrane. Thus, in some embodiments, the chips may comprise an array of nucleic acid sequences or fragments thereof at least 15 nucleotides in length, preferably at least 20 nucleotides in length, and more preferably at least 25 nucleotides in length. In further embodiments, the chip may comprise an array including at least one of the sequences selected from the group consisting of P1 to P28, D1 to D28, and E1 to E28, or the sequences complementary thereto, or a fragment thereof at least 15 consecutive nucleotides. Optionally, the chip may comprise an array including at least one of the sequences selected from the group consisting of P1 to P13 , P15, P17 to P28, D1 to D13, D15, D17 to D28, E1 to E13, E15, and E17 to E28, or the sequences complementary thereto, or a fragment thereof at least 15 consecutive nucleotides. In some embodiments, the chip may comprise an array of at least 2, 3, 4, 5, 6, 7, 8 or more sequences selected from the group consisting of P1 to P28, D1 to D28, and E1 to E28, or the sequences complementary thereto, or a fragment thereof at least 15 consecutive nucleotides. Optionally, the chip may comprise an array of at least 2, 3, 4, 5, 6, 7, 8 or more sequences selected from the group consisting of P1 to P13, P15, P17 to P28, D1 to D13, D15, D17 to D28, E1 to E13, E15, and E17 to E28, or the sequences complementary thereto, or a fragment thereof at least 15 consecutive nucleotides.

The nucleic acid sample which includes the candidate region to be analyzed is isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) describe the fabrication of fluidics devices and particularly microcapillary devices, in silicon and glass substrates.

After the reaction is completed, the chip is inserted into a scanner and patterns of hybridization are detected. The hybridization data is collected, as a signal emitted from the reporter groups already incorporated into the nucleic acid, which is now bound to the probes attached to the chip. Probes that perfectly match a sequence of the nucleic acid sample generally produce stronger signals than those that have mismatches. Since the sequence and position of each probe immobilized on the chip is known, the identity of the nucleic acid hybridized to a given probe can be determined.

For single-nucleotide polymorphism analyses, sets of four oligonucleotide probes (one for each base type), preferably sets of two oligonucleotide probes (one for each base type of the biallelic marker) are generally designed that span each position of a portion of the candidate region found in the nucleic acid sample, differing only in the identity of the polymorphic base. The relative intensity of hybridization to each series of probes at a particular location allows the identification of the base corresponding to the polymorphic base of the probe. Since biallelic polymorphism detection involves identifying single-base mismatches on the nucleic acid sample, greater hybridization stringencies are required (at lower salt concentration and higher temperature over shorter time periods).

The use of direct electric field control improves the determination of single base mutations (Nanogen). A positive field increases the transport rate of negatively charged nucleic acids and results in a 10-fold increase of the hybridization rates. Using this technique, single base pair mismatches are detected in less than 15 sec (see Sosnowski et al., 1997).

5) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection. In a first step, the DNA samples are amplified, preferably by PCR. Then, the amplification products are subjected to automated microsequencing reactions using ddNTPs (specific fluorescence for each ddNTP) and the appropriate oligonucleotide microsequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. This microchip can be used to process at least 96 to 384 samples in parallel. It can use the usual four color laser induced fluorescence detection of the ddNTPs.

IX. Association Studies

The identification of genes associated with a particular trait such as asthma susceptibility or individual response to antiasthmatic drugs can be carried out through two main strategies currently used for genetic mapping: linkage analysis and association studies. Linkage analysis involves the study of families with multiple affected individuals and is now useful in the detection of mono- or oligogenic inherited-traits. Conversely, association studies examine the frequency of marker alleles in unrelated trait positive (T+) individuals compared with control individuals who are randomly selected or preferably trait negative (T−) controls, and are generally employed in the detection of polygenic inheritance.

Association studies as a method of mapping genetic traits rely on the phenomenon of linkage disequilibrium. If two genetic loci lie on the same chromosome, then sets of alleles of these loci on the same chromosomal segment (called haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium (LD).

If a specific allele in a given gene is directly involved in causing a particular trait T, its frequency will be statistically increased in a T+population when compared to the frequency in a T−population. As a consequence of the existence of linkage disequilibrium, the frequency of all other alleles present in the haplotype carrying the trait-causing allele (TCA) will also be increased in T+individuals compared to T−individuals. Therefore, association between the trait and any allele in linkage disequilibrium with the trait-causing allele will suffice to suggest the presence of a trait-related gene in that particular allele's region. Linkage disequilibrium allows the relative frequencies in T+ and T− of a limited number of genetic polymorphisms (specifically biallelic markers) to be analyzed as an alternative to screening all possible functional polymorphisms in order to find trait-causing alleles.

Two alternative approaches can be employed to perform association studies: a genome-wide association study and a candidate gene association study. The genome-wide association study relies on the screening of genetic markers evenly spaced and covering the entire genome. The candidate gene approach is based on the study of genetic markers specifically located in genes potentially involved in a biological pathway related to the trait of interest. The candidate gene analysis clearly provides a short-cut approach to the identification of genes and gene polymorphisms related to a particular trait when some information concerning the biology of the trait is available.

The general strategy to perform association studies using biallelic markers derived from a candidate gene is to scan two group of individuals (trait+and trait−control individuals which are characterized by a well defined phenotype as described below) in order to measure and statistically compare the allele frequencies of such biallelic markers in both groups.

If a statistically significant association with a trait is identified for at least one or more of the analyzed biallelic markers, one can assume that: either the associated allele is directly responsible for causing the trait (the associated allele is the TCA), or the associated allele is in linkage disequilibrium with the TCA. The specific characteristics of the associated allele with respect to the candidate gene function usually gives further insight into the relationship between the associated allele and the trait (causal or in linkage disequilibrium). If the evidence indicates that the associated allele within the candidate gene is most probably not the TCA but is in linkage disequilibrium with the real TCA, then the TCA can be found by sequencing the vicinity of the associated marker.

It is another object of the present invention to provide a method for the identification and characterization of an association between alleles for one or several biallelic markers of the sequence of the FLAP gene and a trait. The method of detecting an association between a genotype and a trait, comprising the steps of: a) determining the frequency of at least one FLAP-related biallelic marker in trait positive population according to a method of the invention; b) determining the frequency of at least one FLAP-related biallelic marker in a control population according to a method of the invention; and c) determining whether a statistically significant association exists between said genotype and said trait; Optionally, said biallelic markers are selected from the group consisting of A1 to A28, and the complements thereof, or optionally the biallelic markers in linkage disequilibrium therewith; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16, and the complements thereof, or optionally the biallelic markers in linkage disequilibrium therewith. Optionally, the trait is either a disease, preferably a disease involving the leukotriene pathway, most preferably asthma, a beneficial response to treatment with agents acting on the leukotriene pathway or side-effects related to treatment with agents acting on the leukotriene pathway. Optionally, said genotyping steps a) and b) may be performed on a pooled biological sample derived from each of said populations; Optionally, said genotyping steps a) and b) are performed separately on biological samples derived from each individual in said population or a subsample thereof; Optionally, said control individuals are trait negative or random controls.

The invention also encompasses methods of estimating the frequency of a haplotype for a set of biallelic markers in a population, comprising the steps of: a) genotyping at least one FLAP-related biallelic marker according to a method of the invention for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, particularly in "Statistical methods", or those following, specified alone or in any combination; Optionally, said biallelic markers are selected from the group consisting of A1 to A28, and the complements thereof, or optionally the biallelic markers in linkage disequilibrium therewith; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16, and the complements thereof, or optionally the biallelic markers in linkage disequilibrium therewith. Optionally, said haplotype determination method is performed by asymmetric PCR amplification, double PCR amplification of specific alleles, the Clark algorithm, or an expectation-maximization algorithm.

The present invention also provides a method for the identification and characterization of an association between a haplotype comprising alleles for several biallelic markers of the genomic sequence of the FLAP gene and a trait. The method comprises the steps of: a) genotyping a group of biallelic markers according to the invention in trait positive and control individuals; and b) establishing a statistically significant association between a haplotype and the trait. In a further embodiment, a method for the identification and characterization of an association between a haplotype comprising alleles for several biallelic markers of the genomic sequence of the FLAP gene and a trait comprises the steps of: a) estimating the frequency of at least one haplotype in a trait positive population according to a method of the invention; b) estimating the frequency of said haplotype in a control population according to a method of the invention; and c) determining whether a statistically significant association exists between said haplotype and said trait. In addition, the methods of detecting an association between a haplotype and a phenotype of the invention encompass methods with any further limitation described in this disclosure, or those following; Optionally, said biallelic markers are selected from the group consisting of A1 to A28, and the complements thereof, or optionally the biallelic markers in linkage disequilibrium therewith; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16, and the complements thereof, or optionally the biallelic markers in linkage disequilibrium therewith. Optionally, the trait is a disease, preferably a disease involving the leukotriene pathway, most preferably asthma, a beneficial response to treatment with agents acting on the leukotriene pathway or side-effects related to treatment with agents acting on the leukotriene pathway; Optionally, said control individuals are trait negative or random controls. Optionally, said method comprises the additional steps of determining the phenotype in said trait positive and said control populations prior to step c).

If the trait is a beneficial response or conversely a side-effect to treatment with an agent acting on the leukotriene pathway, the method of the invention referred to above further comprises some or all of the following steps: a) selecting a population or cohort of subjects diagnosed as suffering from a specified disease involving the leukotriene pathway; b) administering a specified agent acting on the leukotriene pathway to said cohort of subjects; c) monitoring the outcome of drug administration and identifying those individuals that are trait positive or trait negative relative to the treatment; d) taking from said cohort biological samples containing DNA and testing this DNA for the presence of a specific allele or of a set of alleles for biallelic markers of the FLAP gene; e) analyzing the distribution of alleles for biallelic markers between trait positive and trait negative individuals; and, f) performing a statistical analysis to determine if there is a statistically significant association between the presence or absence of alleles of biallelic markers of the FLAP gene and the treatment related trait. Optionally, said biallelic markers are selected from the group consisting of A1 to A28, and the complements thereof, or optionally the biallelic markers in linkage disequilibrium therewith; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16 and the complements thereof. The step of testing for and detecting the presence of DNA comprising specific alleles of a biallelic marker or a group of biallelic markers of the present invention can be carried out as described in the present invention.

The invention also encompasses methods of determining whether an individual is at risk of developing asthma, comprising the steps of: a) genotyping at least one FLAP-related biallelic marker according to a method of the present invention; and b) correlating the result of step a) with a risk of developing asthma; optionally wherein said FLAP-related biallelic marker is selected from the group consisting of A1 to A28; optionally, wherein said FLAP-related biallelic marker is selected from the following list of biallelic markers: A2, A14, A16, A18, A19, A22, and A23; and optionally, wherein said FLAP-related biallelic marker is the biallelic marker A19.

1) Collection of DNA Samples from Trait Positive (Trait +) and Control Individuals (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected or trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. In the following "trait positive population", "case population" and "affected population" are used interchangeably.

In order to perform efficient and significant association studies such as those described herein, the trait under study should preferably follow a bimodal distribution in the population under study, presenting two clear non-overlapping phenotypes, trait+ and trait−.

Nevertheless, even in the absence of such bimodal distribution (as may in fact be the case for more complex genetic traits), any genetic trait may still be analyzed by the association method proposed here by carefully selecting the individuals to be included in the trait+ and trait− phenotypic groups. The selection procedure involves selecting individuals at opposite ends of the non-bimodal phenotype spectra of the trait under study, so as to include in these trait+ and trait− populations individuals which clearly represent extreme, preferably non-overlapping phenotypes.

The definition of the inclusion criteria for the trait+ and trait− populations is an important aspect of the present invention.

Typical examples of inclusion criteria include a disease involving the leukotriene pathway such as asthma or the evaluation of liver transaminase levels following treatment with an anti-asthma drug such as Zileuton. From a statistical viewpoint, if one considers that in a given population liver transaminase levels follow a standard distribution curve, individuals with extreme phenotypes according to the optimal inclusion criteria would correspond respectively to those exhibiting the lowest liver transaminase levels and those exhibiting the highest liver transaminase levels.

The selection of those drastically different but relatively uniform phenotypes enables efficient comparisons in association studies and the possible detection of marked differences at the genetic level, provided that the sample sizes of the populations under study are significant enough.

Generally, trait+ and trait− populations to be included in association studies such as those described in the present application consist of phenotypically homogenous populations of individuals each representing 100% of the corresponding trait if the trait distribution is bimodal.

If the trait distribution is non-bimodal, trait+ and trait− populations consist of phenotypically uniform populations of individuals representing between 1 and 98%, preferably between 1 and 80%, more preferably between 1 and 50%, and most preferably between 4 and 35% of the total population under study, and selected from individuals exhibiting the extreme phenotypes of the group. The clearer is the difference between the two trait phenotypes, the greater is the probability to observe an association with biallelic markers.

A first group of between 50 and 300 trait+ individuals, preferably about 100 individuals, are recruited according to clinical inclusion criteria based on either 1) affection by disease(s) involving the leukotriene pathway, preferably asthma, 2) evidence of side-effects observed following administration of an agent acting on the leukotriene pathway, preferably increased liver transaminase levels following administration of Zileuton, or 3) evidence of particular responses to treatment with agents acting on the leukotriene pathway.

In each case, a similar number of trait negative individuals are included in such studies. They are checked for the absence of the clinical criteria defined above. Both trait+and trait−individuals should be unrelated cases.

In the context of the present invention, one association study were carried out. The considered trait was asthma. Collection of DNA samples from trait+and trait−individuals is described in Example 5.

2) Genotyping of Trait+and Trait−Individuals

Allelic frequencies of the biallelic markers in each of the above described populations can be determined using one of the methods described above under the heading "Methods of Genotyping DNA samples for Biallelic Markers ". Analyses are preferably performed on amplified fragments obtained by genomic PCR performed on the DNA samples from each individual in similar conditions as those described above for the generation of biallelic markers.

In a preferred embodiment, amplified DNA samples are subjected to automated microsequencing reactions using fluorescent ddNTPs (specific fluorescence for each ddNTP) and the appropriate oligonucleotide microsequencing primers which hybridize just upstream of the polymorphic base. Genotyping is further described in Example 5.

3) Single Marker Association Studies and Haplotype Frequency Analysis

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if there is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

In preferred embodiments, significance for diagnosis purposes, either as a positive basis for further diagnostic tests or as a preliminary starting point for early preventive therapy, the p value related to a biallelic marker association is preferably about $1\times10^{-2}$ or less, more preferably about $1\times10^{-4}$ or less, for a single biallelic marker analysis and about $1\times10^{-3}$ or less, still more preferably $1\times10^{10-6}$ or less and most preferably of about $1\times10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and a disease involving the leukotriene pathway can be revealed and used for diagnosis and drug screening purposes.

To address the problem of false positives similar analysis may be performed with the same case-control populations in random genomic regions. Results in random regions and the candidate region are compared as described in a co-pending U.S. Provisional Patent Application entitled "Methods, Software And Apparati For Identifying Genomic Regions Harboring A Gene Associated With A Detectable Trait," U.S. Ser. No. 60/107,986, filed Nov. 10, 1998, the contents of which are incorporated herein by reference.

Single Marker Association

Association studies are usually run in two successive steps. In a first phase, the frequencies of a reduced number of biallelic markers, usually between 2 and 10 markers, is determined in the trait+and trait−populations. In a second phase of the analysis, the position of the genetic loci responsible for the given trait is further refined using a higher density set of markers. However, if the candidate gene under study is relatively small in length, as it is the case for the FLAP gene, it is believed that a single phase is sufficient to establish significant associations.

In one preferred embodiment of the invention in which a correlation was found between a set of biallelic markers of the FLAP gene and a disease involving the leukotriene pathway, more particularly asthma, results of the first step of the association study, further details of which are provided in example 7, seem to indicate that asthma is associated most strongly with the biallelic marker A19 (10-35/390, allele T). Further details concerning these associations are provided in Example 7.

Similar association studies can also be carried out with other biallelic markers within the scope of the invention, preferably with biallelic markers in linkage disequilibrium with the markers associated with asthma, including the biallelic markers A1 to A28.

Similar associations studies can be routinely carried out by the skilled technician using the biallelic markers of the invention which are defined above with different trait+and trait−populations. Suitable further examples of possible association studies using biallelic markers of the FLAP gene, including the biallelic markers A1 to A28, involve studies on the following populations:
- a trait+population suffering from a disease involving the leukotriene pathway and a healthy unaffected population; or
- a trait+population treated with agents acting on the leukotriene pathway suffering from side-effects resulting from the treatment and an trait−population treated with same agents without any side-effects; or
- a trait+population treated with agents acting on the leukotriene pathway showing a beneficial response and a trait−population treated with same agents without any beneficial response.

Haplotype Frequency Analysis

A haplotype analysis is interesting in that it increases the statistical significance of an analysis involving individual markers. Indeed, by combining the informativeness of a set of biallelic markers, it increases the value of the results obtained through association analyses, allowing false positive and/or negative data that may result from the single marker studies to be eliminated.

In a first stage of a haplotype frequency analysis, the frequency of the possible haplotypes based on various combinations of the identified biallelic markers of the invention is determined and compared for distinct populations of trait+ and trait−individuals. The number of trait+individuals which should be subjected to this analysis to obtain statistically significant results usually ranges between 30 and 300, with a preferred number of individuals ranging between 50 and 150. The same considerations apply to the number of unaffected controls used in the study.

The results of this first analysis provide haplotype frequencies for the tested trait+and trait−individuals, and the estimated p value for each evaluated haplotype.

In the association of the biallelic markers of FLAP gene with the asthma, several haplotypes were also shown to be significant (see FIG. 3). For example, the preferred haplotypes comprise the allele T of the biallelic marker A19 (10-35/390). The more preferred haplotype (HAP 1 of FIG. 3) comprise the allele A of the marker A14 (10-33/234) and the allele T of the marker A19 (10-35/390). This haplotype is considered to be highly significant of an association with asthma. The other significant haplotypes are detailed in Example 8.

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the probability to obtain by chance the tested haplotype.

For the association between asthma and the three considered haplotypes, a randomized haplotype analysis was reiterated 1000 times or 10000 times and the results are shown in FIG. 4. These results demonstrate that among 1000 iterations none and among 10,000 iterations only 1 of the obtained haplotypes had a p-value comparable to the one obtained for the haplotype HAP1. These results clearly validate the statistical significance of the association between this haplotype and asthma.

Using the method described above and evaluating the associations for single marker alleles or for haplotypes permits an estimation of the risk a corresponding carrier has to develop a given trait, and particularly in the context of the present invention, a disease, preferably a disease involving the leukotriene pathway, more preferably asthma. Significance thresholds of relative risks are to be adapted to the reference sample population used. The evaluation of the risk factors is detailed in "Statistical methods".

It will of course be understood by practitioners skilled in the treatment of diseases involving the leukotriene pathway listed above, and in particular asthma, that the present invention does not intend to provide an absolute identification of individuals who could be at risk of developing a particular disease involving the leukotriene pathway or who will or will not respond or exhibit side-effects to treatment with agents acting on the leukotriene pathway but rather to indicate a certain degree or likelihood of developing a disease or of observing in a given individual a response or a side-effect to treatment with said agents.

However, this information is extremely valuable as it can, in certain circumstances, be used to initiate preventive treatments or to allow an individual carrying a significant haplotype to foresee warning signs such as minor symptoms. In diseases such as asthma, in which attacks may be extremely violent and sometimes fatal if not treated on time, the knowledge of a potential predisposition, even if this predisposition is not absolute, might contribute in a very significant manner to treatment efficacy. Similarly, a diagnosed predisposition to a potential side-effect could immediately direct the physician toward a treatment for which such side-effects have not been observed during clinical trials.

X. Statistical Methods

In general, any method known in the art to test whether a trait and a genotype show a statistically significant correlation may be used.

1) Methods to Estimate Haplotype Frequencies in a Population

The gametic phase of haplotypes is unknown when diploid individuals are heterozygous at more than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosomes by limit dilution followed by PCR amplification (see Ruano et al., 1990). Further, a sample may be haplotyped for sufficiently close biallelic markers by double PCR amplification of specific alleles (Sarkar, G. and Sommer S. S., 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark, A. G. (1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. The EM algorithm can be applied using for example the EM-HAPLO program (Hawley M. E. et al., 1994) or the Arlequin program (Schneider et al., 1997). Any other method known in the art to determine or to estimate the frequency of a haplotype in a population may be used (see Lange K., 1997; Weir, B. S., 1996). The EM algorithm is briefly described below.

A sample of N unrelated individuals is typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \quad \text{Equation 1}$$

where Pj is the probability of the phenotype j, $h_k$ and $h_l$ are the two haplotypes constituent the genotype i. Under the Hardy-Weinberg equilibrium, $pr(h_k, h_l)$ becomes:

$pr(h_k,h_l)=pr(h_k)^2$ if $h_k=h_l$, $pr(h_k,h_l)=2pr(h_k).pr(h_l)$ if $h_k \neq h_l$. Equation 2

The successive steps of the E-M algorithm can be described as follows:

Starting with initial values of the of haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

At a given iteration s, the Expectation step consists in calculating the genotypes frequencies by the following equation:

$$pr(genotype_i)^{(s)} = pr(phenotype_j) \cdot \quad \text{Equation 3}$$
$$pr(genotype_i \mid phenotype_j)^{(s)}$$
$$= \frac{n_j}{N} \cdot \frac{pr(h_k, h_l)^{(s)}}{P_j^{(s)}}$$

where genotype i occurs in phenotype j, and where $h_k$ and $h_l$ constitute genotype i. Each probability is derived according to eq. 1, and eq. 2 described above.

Then the Maximization step simply estimates another set of haplotype frequencies given the genotypes frequencies. This approach is also known as the gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \quad \text{Equation 4}$$

Where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

2) Methods to Calculate Linkage Disequilibrium between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j$; $a_i,b_j$; $b_i,a_j$ and $b_i,b_j$), according to the Piazza formula:

$\Delta_{aiaj}=\sqrt{\theta 4} - \sqrt{(\theta 4+\theta 3)(\theta 4+\theta 2)}$, where:

θ4=−−=frequency of genotypes not having allele $a_i$ at $M_i$ and not having allele $a_j$ at $M_j$ θ3=−+=frequency of genotypes not having allele as at $M_i$ and having allele $a_j$ at $M_j$ θ2=+−=frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination (ai,aj; ai,bj; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$D_{aiaj}=(2n_1+n_2+n_3+n_4/2)/N-2(pr(a_i).pr(a_j))$

Where $n_1=\Sigma$ phenotype ($a_i/a_i, a_j/a_j$), $n_2=\Sigma$ phenotype ($a_i/a_i, a_j/b_j$), $n_3=\Sigma$ phenotype ($a_i/b_i, a_j/a_j$), n4=$\Sigma$ phenotype ($a_i/b_i, a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i(a_i/b_i)$ and $M_j(a_j/b_j)$, fitting the Hardy-Weinberg equilibrium, one can estimate the four possible haplotype frequencies in a given population according to the approach described above.

The estimation of gametic disequilibrium between ai and aj is simply:

$D_{aiaj}=pr(\text{haplotype}(a_i,a_j))-pr(a_i).pr(a_j)$.

Where $pr(a_i)$ is the probability of allele $a_i$ and $pr(a_j)$ is the probability of allele $a_j$ and where pr(haplotype ($a_i, a_j$)) is estimated as in Equation 3 above.

For a couple of biallelic markers only one measure of disequilibrium is necessary to describe the association between $M_i$ and $M_j$.

Then a normalized value of the above is calculated as follows:

$D'_{aiaj}=D_{aiaj}/\max(-pr(a_i).pr(a_j), -pr(b_i).pr(b_j))$ with $D_{aiaj}<0$ $D'_{aiaj}=D_{aiaj}/\max(pr(b_i).pr(a_j), pr(a_i).pr(b_j))$ with $D_{aija}>0$ The skilled person will readily appreciate that other linkage disequilibrium calculation methods can be used.

Linkage disequilibrium among a set of biallelic markers having an adequate heterozygosity rate can be determined by genotyping between 50 and 1000 unrelated individuals, preferably between 75 and 200, more preferably around 100.

3) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR=P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR=(F^+/(1-F^+))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive . . . ).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR=P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

XI. Identification of Biallelic Markers in Linkage Disequilibrium with the Biallelic Markers of the Present Invention.

Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

The invention also concerns a method for the identification and characterization of a biallelic marker in linkage disequilibrium with a biallelic marker of a FLAP gene, preferably a biallelic marker of a FLAP gene of which one allele is associated with a trait. In one embodiment, the biallelic marker in linkage disequilibrium with a biallelic marker of the FLAP gene is in the genomic region harboring the FLAP gene, but outside of the FLAP gene itself. In another embodiment, the biallelic marker in linkage disequilibrium with a biallelic marker of the FLAP gene is itself located within the FLAP gene. The method comprises the following steps: a) amplifying a genomic fragment comprising a first biallelic marker from a plurality of individuals; b) identifying second biallelic markers in the genomic region harboring the first biallelic marker; c) conducting a linkage disequilibrium analysis between said first biallelic marker and second biallelic markers; and d) selecting said second biallelic markers in linkage disequilibrium with said first marker.

In one embodiment, the step of sequencing and identifying second biallelic markers comprises sequencing second biallelic markers within the FLAP gene. In a further embodiment, the step of sequencing and identifying second biallelic markers comprises sequencing second biallelic markers within the amplified region of the FLAP gene.

Once identified, the sequences in linkage disequilibrium with a biallelic marker of the FLAP gene may be used in any of the methods described herein, including methods for determining an association between biallelic marker and a trait, methods for identifying individuals having a predisposition for a trait, methods of disease treatment, methods of identifying individuals likely to respond positively or negatively to drug treatment, and methods of using drugs. In particular, biallelic markers in linkage disequilibrium with a biallelic marker in the FLAP gene may be used to identify individuals having a predisposition to asthma or to positive or negative responses to treatment with anti-asthma drugs such as Zileuton.

Methods to identify biallelic markers and to conduct linkage disequilibrium analysis are described herein in "Statistical methods" and can be carried out by the skilled person without undue experimentation. The present invention then also concerns biallelic markers which are in linkage disequilibrium with the specific biallelic markers A1 to A28 and which are expected to present similar characteristics in terms of their respective association with a given trait.

XII. Identification of Trait-Causing Mutations in the FLAP Gene

Mutations in the FLAP gene which are responsible for a detectable phenotype may be identified by comparing the sequences of the FLAP genes from trait-positive and trait-negative individuals. Preferably, trait+individuals to be sequenced carry the haplotype shown to be associated to the trait and trait−individuals to be sequenced do not carry the haplotype associated to the trait. The detectable phenotype may comprise a variety of manifestations of altered FLAP function, including a disease involving the leukotriene pathway, a response to an agent acting on the leukotriene pathway or side-effects linked to a treatment with this agent. The mutations may comprise point mutations, deletions, or insertions in the FLAP gene. The mutations may lie within the coding sequence for the FLAP protein or within regulatory regions in the FLAP gene.

The method used to detect such mutations generally comprises the following steps: a) amplification of a region of the FLAP gene comprising a biallelic marker or a group of biallelic markers associated with the trait from DNA samples of trait positive patients and trait negative controls; b) sequencing of the amplified region; c) comparison of DNA sequences from trait-positive patients and trait-negative controls; and, d) determination of mutations specific to trait-positive patients.

Oligonucleotide primers are constructed as described previously to amplify the sequences of each of the exons, introns or the promoter region of the FLAP gene.

Each primer pair is used to amplify the exon or promoter region from which it is derived. Amplification is carried out on genomic DNA samples from trait positive patients and trait negative controls, preferably using the PCR conditions described in the examples. Amplification products from the genomic PCRs are then subjected to sequencing, preferably through automated dideoxy terminator sequencing reactions and electrophoresed, preferably on ABI 377 sequencers. Following gel image analysis and DNA sequence extraction, ABI sequence data are automatically analyzed to detect the presence of sequence variations among trait positive and trait negative individuals. Sequences are verified by determining the sequences of both DNA strands for each individual.

Candidate polymorphisms suspected of being responsible for the detectable phenotype, such as a disease, a beneficial response to an agent acting on the leukotriene pathway or side-effects linked to a treatment with this agent, are then verified by screening a larger population of trait positive and trait negative individuals using polymorphism analysis techniques such as the techniques described above. Polymorphisms which exhibit a statistically significant correlation with the detectable phenotype are deemed responsible for the detectable phenotype.

Most of the biallelic polymorphisms of the FLAP gene observed in the context of the present invention do not appear to drastically modify the amino acid sequence of the FLAP protein. Also, they do not seem to be located in splicing sequences. However, they may be associated with changes in basic FLAP expression in one or more tissues. Such polymorphisms may eventually modify the transcription rate of FLAP DNA, FLAP mRNA stability, or the translation rate of FLAP mRNA.

The biallelic polymorphisms may also be associated with changes in the modulation of FLAP expression through expression modifiers. The term "expression modifier" is intended to encompass chemical agents that modulate the action of FLAP through modulation of FLAP gene expression.

The basic FLAP expression levels in different tissues can be determined by analyses of tissue samples from individuals typed for the presence or absence of a specific polymorphism. Any convenient method can be used such as ELISA, RIA for protein quantitation, and such as Northern blot or other hybridization analyses, and quantitative RT-PCR for mRNA quantitation. The tissue specific expression can then be correlated with the genotype. More details on some of these methods are provided below under the heading "Screening of agents".

Furthermore, the strong association observed for the first time between the FLAP gene and asthma confirms the need to locate and study any mutation of the FLAP gene as such mutation is susceptible of having an incidence on leukotriene metabolism and hence on the therapeutic choices made when considering various treatment alternatives for an individual with a particular condition involving the leukotriene pathway.

There are numerous possibilities for causal mutations within the FLAP gene. One of the causal mutations can be an amino acid change in the FLAP protein which can lead to alterations in FLAP substrate specificity and/or activity. Methods for analyzing protein-protein or protein-ligand interactions are detailed below under the heading "Screening of agents".

Another possible causal mutation of the FLAP gene is a modification in its regulatory region, and particularly in the sequence of its native promoter. This type of mutation can be studied through the determination of basic expression levels by expression assays for the particular promoter sequence. The assays may be performed with the FLAP coding sequence or with a detectable marker sequence. To determine tissue specificity, the assay is performed in cells from different sources. Some methods are discussed in more detail below under the heading "Screening of agents".

When used herein, the term "basic expression levels" intends to designate FLAP expression levels normally observed in individuals not bearing the associated allele of biallelic markers of the present invention.

In another embodiment, the mutant FLAP allele which causes a detectable phenotype can be isolated by obtaining a nucleic acid sample such as a genomic library or a cDNA library from an individual expressing the detectable phenotype. The nucleic acid sample can be contacted with one or more probes lying in the region of the FLAP gene where the associated biallelic marker or group of biallelic markers or with PCR-typeable primers specific to the amplification of this biallelic marker or group of biallelic markers. The mutation can be identified by conducting sequencing reactions on the nucleic acids which hybridize with the probes defined herein or which show amplification by PCR. The region of the FLAP gene containing the mutation responsible for the detectable phenotype may be used in diagnostic techniques such as those described below. For example, microsequencing oligonucleotides, or oligonucleotides containing the mutation responsible for the detectable phenotype for amplification, or hybridization based diagnostics, such as those described herein, may be used for detecting individuals suffering from the detectable phenotype or individuals at risk of developing the detectable phenotype at a subsequent time. In addition, the FLAP allele responsible for the detectable phenotype may be used in gene therapy. The FLAP allele responsible for the detectable phenotype may also be cloned into an expression vector to express the mutant FLAP protein as described herein.

XIII. Biallelic Markers of the Invention in Methods of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including a disease involving the leukotriene pathway, a beneficial response to treatment with agents acting on the leukotriene pathway or side-effects related to treatment with agents acting on the leukotriene pathway.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The present invention provides diagnostic methods to determine whether an individual is at risk of developing a disease or suffers from a disease resulting from a mutation or a polymorphism in the FLAP gene. The present invention also provides methods to determine whether an individual is likely to respond positively to an agent acting on the leukotriene pathway or whether an individual is at risk of developing an adverse side-effect to an agent acting on the leukotriene pathway.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular FLAP polymorphism or mutation (trait-causing allele).

Preferably, in such diagnostic methods, a nucleic acid sample is obtained from the individual and this sample is genotyped using methods described above in VIII. The diagnostics may be based on a single biallelic marker or on a group of biallelic markers.

In each of these methods, a nucleic acid sample is obtained from the test subject and the biallelic marker pattern of one or more of the biallelic markers A1 to A28, the complements thereof or a biallelic marker in linkage disequilibrium therewith is determined.

In one embodiment, a PCR amplification is conducted on the nucleic acid sample to amplify regions in which polymorphisms associated with a detectable phenotype have been identified. The amplification products are sequenced to determine whether the individual possesses one or more FLAP polymorphisms associated with a detectable phenotype. The primers used to generate amplification products may comprise the primers B1 to B17 and C1 to C17. Alternatively, the nucleic acid sample is subjected to microsequencing reactions as described above to determine whether the individual possesses one or more FLAP polymorphisms associated with a detectable phenotype resulting from a mutation or a polymorphism in the FLAP gene. The primers used in the microsequencing reactions may include the primers D1 to D28 and E1 to E28. In another embodiment, the nucleic acid sample is contacted with one or more allele specific oligonucleotide probes which, specifically hybridize to one or more FLAP alleles associated with a detectable phenotype. The probes used in the hybridization assay may include the probes P1 to P28, a complementary sequence thereto or a fragment thereof comprising the polymorphic base. In another embodiment, the nucleic acid sample is contacted with a second FLAP oligonucleotide capable of producing an amplification product when used with the allele specific oligonucleotide in an amplification reaction. The presence of an amplification product in the amplification reaction indicates that the individual possesses one or more FLAP alleles associated with a detectable phenotype.

In a preferred embodiment, the identity of the nucleotide present at, at least one biallelic marker selected from the group consisting of A2, A14, A16, A18, A19, A22, and A23, and the complements thereof, or optionally the biallelic markers in linkage disequilibrium therewith, is determined and the detectable trait is asthma. In another preferred embodiment the identity of the nucleotide present at, at least one of the polymorphic sites selected from the group consisting of A14 and A19, and the complements thereof, or optionally the biallelic markers in linkage disequilibrium therewith, is determined. In more preferred embodiment, the identity of the nucleotide present at the polymorphic site A19, and the complements thereof, or optionally the biallelic markers in linkage disequilibrium therewith, is determined. Diagnostic kits comprising polynucleotides of the present invention are further described in the present invention.

These diagnostic methods are extremely valuable as they can, in certain circumstances, be used to initiate preventive treatments or to allow an individual carrying a significant haplotype to foresee warning signs such as minor symptoms. In diseases in which attacks may be extremely violent and sometimes fatal if not treated on time, such as asthma, the knowledge of a potential predisposition, even if this predisposition is not absolute, might contribute in a very significant manner to treatment efficacy.

The present invention also encompasses diagnostic kits comprising one or more polynucleotides of the invention with a portion or all of the necessary reagents and instructions for genotyping a test subject by determining the identity of a nucleotide at a FLAP-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or a mismatch detection assay based on polymerases and/or ligases. The diagnostic kits can be manufactured to perform any of the genotyping methods described in the current application using manufacturing and formulation methods commonly in the art. Preferably such a kit may provide for the determination of the allele of a biallelic marker selected from FLAP-related biallelic markers. Optionally such a kit may include instructions for scoring the results of the determination with respect to the test subjects' risk of contracting a disease involving the leukotriene pathway, a beneficial response to treatment with agents acting on the leukotriene pathway or side-effects related to treatment with agents acting on the leukotriene pathway.

XIV. Treatment of Diseases Involving the Leukotriene Pathway

The invention also relates to a method of determining whether a subject is likely to respond positively to treatment with a medicament, preferably a medicament acting directly or indirectly on the leukotriene pathway.

The method comprises identifying a first population of individuals who response positively to said medicament and a second population of individuals who respond negatively to said medicament. One or more biallelic markers is identified in the first population which is associated with a positive response to said medicament or one or more biallelic markers is identified in the second population which is associated with a negative response to said medicament. The biallelic markers may be identified using the techniques described herein.

The DNA sample is then obtained form the subject tested. The DNA sample is analyzed to determine whether it comprises one or more alleles of biallelic markers associated with a positive response to a medicament or one or more alleles of biallelic markers associated with a negative response to treatment with the medicament. In some embodiments, the DNA sample is analyzed to identify subjects whose DNA comprises one or more alleles of biallelic markers associated with a positive response to the medicament and whose DNA lacks one or more alleles of biallelic markers associated with a negative response to treatment with the medicament.

In other embodiments, the medicament is administered to the subject in a clinical trial if the DNA sample contains one or more alleles of biallelic markers associated with positive response to the medicament and/or if the DNA sample lacks one or more alleles of biallelic markers associated with a negative response to treatment with the medicament. In preferred embodiments, the medicament is an anti-asthma drug such as Zileuton. In other embodiments, the negative response comprises one or more side-effects, such as increased liver transaminase levels. Using the methods of the present invention, the evaluation of drug efficacy may be conducted in a population of individuals likely to respond favorably to the medicament.

The invention also concerns a method for the clinical testing of a medicament, preferably a medicament acting directly or indirectly on the leukotriene pathway. The method comprises the following steps: a) administering a medicament, preferably a medicament capable of acting directly or indirectly on the leukotriene pathway to a heterogeneous population of individuals; b) identifying a first population of individuals who response positively to said medicament and a second population of individuals who respond negatively to said medicament; c) identifying biallelic markers in said first population which are associated with a positive response to said medicament and/or biallelic markers in said second population which are associated with a negative response to said medicament; d) selecting individuals whose DNA comprises one or more alleles of biallelic markers associated with a positive response to said medicament and/or whose DNA lacks one or more alleles of biallelic markers associated with a negative response to said medicament; and, d) administering said medicament to said individuals.

Such methods are deemed to be extremely useful to increase the benefit/risk ratio resulting from the administration of medicaments which may cause undesirable side-effects and/or be inefficacious to a portion of the patient population to which it is normally administered.

Once an individual has been diagnosed as suffering from a disease involving the leukotriene pathway such as asthma, selection tests are carried out to determine whether the DNA of this individual comprises alleles of a biallelic marker or of a group of biallelic markers associated a positive response to treatment or with a negative response to treatment which may include either side-effects or unresponsiveness.

The selection of the patient to be treated using the method of the present invention can be carried out through the detection methods described above. The individuals which are to be selected are preferably those whose DNA does not comprise alleles of a biallelic marker or of a group of biallelic markers associated with negative response to treatment.

Once the patient's genetic predispositions have been determined, the clinician can select appropriate treatment for which the particular side-effect observed for the patient has not been reported or has been reported only marginally and preferably from an allelic association which does not involve the same biallelic marker or markers as those found in the DNA of the patient. Several drugs useful in the treatment of diseases involving the leukotriene pathway may be chosen. Compounds acting on the leukotriene pathway are described for example in U.S. Pat. Nos. 4,873,259; 4,970,215; 5,310,744; 5,225,421; and 5,081,138, or in EP 0 419 049, the disclosures of which are incorporated by reference.

XV. FLAP Proteins and Polypeptide Fragments

The term "FLAP polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies FLAP proteins from humans, including isolated or purified FLAP proteins consisting, consisting essentially, or comprising the sequence of SEQ ID No 3 and comprising an isoleucine at position 127 in SEQ ID No 3. It should be noted the FLAP proteins of the invention are based on the naturally-occurring variant of the amino acid sequence of human FLAP, wherein the valine residue of amino acid position 127 in SEQ ID No 3 has been replaced with an isoleucine residue. This variant protein and the fragments thereof which contain amino acid position 127 of SEQ ID No 3 are collectively referred to herein as "127-Ile variants" or 127-Ile FLAP polypeptides".

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 3, wherein said contiguous span includes an isoleucine residue at amino acid position 127 in SEQ ID No 3. In other preferred embodiments the contiguous stretch of amino acids comprises the site of a mutation or functional mutation, including a deletion, addition, swap or truncation of the amino acids in the FLAP protein sequence.

FLAP proteins are preferably isolated from human or mammalian tissue samples or expressed from human or mammalian genes. The FLAP polypeptides of the invention can be made using routine expression methods known in the art. The polynucleotide encoding the desired polypeptide, is ligated into an expression vector suitable for any convenient host. Both eukaryotic and prokaryotic host systems are used in forming recombinant polypeptides, and a summary of some of the more common systems. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments are produced by chemical synthesis. Alternatively the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any FLAP cDNA, including SEQ ID No 2, is used to express FLAP proteins and polypeptides. The preferred FLAP cDNA comprises the allele A of the biallelic marker A21. The nucleic acid encoding the FLAP protein or polypeptide to be expressed is operably linked to a promoter in an expression vector using conventional cloning technology. The FLAP insert in the expression vector may comprise the full coding sequence for the FLAP protein or a portion thereof. For example, the FLAP derived insert may encode a polypeptide comprising at least 10 consecutive amino acids of the FLAP protein of SEQ ID No 3, where in said consecutive amino acids comprising an isoleucine residue in amino acid position 127.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767.

In one embodiment, the entire coding sequence of the FLAP cDNA through the poly A signal of the cDNA are operably linked to a promoter in the expression vector. Alternatively, if the nucleic acid encoding a portion of the FLAP protein lacks a methionine to serve as the initiation site, an initiating methionine can be introduced next to the first codon of the nucleic acid using conventional techniques. Similarly, if the insert from the FLAP cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the FLAP protein or a portion thereof is obtained by PCR from a bacterial vector containing the FLAP cDNA of SEQ ID No 3 using oligonucleotide primers complementary to the FLAP cDNA or portion thereof and containing restriction endonuclease sequences for Pst I incorporated into the 5' primer and BglII at the 5' end of the corresponding cDNA 3' primer, taking care to ensure that the sequence encoding the FLAP protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

Alternatively, the nucleic acids encoding the FLAP protein or a portion thereof is cloned into pED6dpc2 (Genetics Institute, Cambridge, Mass.). The resulting pED6dpc2 constructs is transfected into a suitable host cell, such as COS 1 cells. Methotrexate resistant cells are selected and expanded.

The above procedures may also be used to express a mutant FLAP protein responsible for a detectable phenotype or a portion thereof.

The expressed proteins are purified using conventional purification techniques such as ammonium sulfate precipitation or chromatographic separation based on size or charge. The protein encoded by the nucleic acid insert may also be purified using standard immunochromatography techniques. In such procedures, a solution containing the expressed FLAP protein or portion thereof, such as a cell extract, is applied to a column having antibodies against the FLAP protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the FLAP protein or a portion thereof, the proteins expressed from host cells containing an expression vector containing an insert encoding the FLAP protein or a portion thereof can be compared to the proteins expressed in host cells containing the expression vector without an insert. The presence of a band in samples from cells containing the expression vector with an insert which is absent in samples from cells containing the expression vector without an insert indicates that the FLAP protein or a portion thereof is being expressed. Generally, the band will have the mobility expected for the FLAP protein or portion thereof. However, the band may have a mobility different than that expected as a result of modifications such as glycosylation, ubiquitination, or enzymatic cleavage.

Antibodies capable of specifically recognizing the expressed FLAP protein or a portion thereof are described below.

If antibody production is not possible, the nucleic acids encoding the FLAP protein or a portion thereof is incorporated into expression vectors designed for use in purification schemes employing chimeric polypeptides. In such strategies the nucleic acid encoding the FLAP protein or a portion thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites is engineered between the β-globin gene or the nickel binding polypeptide and the FLAP protein or portion thereof. Thus, the two polypeptides of the chimera is separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind FLAP Polypeptides of the Invention

Any FLAP polypeptide or whole protein may be used to generate antibodies capable of specifically binding to expressed FLAP protein or fragments thereof as described. The antibody compositions of the invention are capable of specifically binding or specifically bind to the 127-Ile variant of the FLAP protein. For an antibody composition to specifically bind to the 127-Ile variant of FLAP it must demonstrate at least a 5%, 10%, 15%, 20%, 25%, 50%, or 100% greater binding affinity for full length 127-Ile variant of FLAP than for full length 127-Val variant of FLAP in an ELISA, RIA, or other antibody-based binding assay.

In a preferred embodiment of the invention antibody compositions are capable of selectively binding, or selectively bind to an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of SEQ ID No 3, wherein said epitope comprises an isoleucine residue at amino acid position 127 in SEQ ID No 3, wherein said antibody composition is optionally either polyclonal or monoclonal.

The present invention also contemplates the use of polypeptides comprising a contiguous span of at least 6 amino acids, preferably at least 8 to 10 amino acids, more preferably at least 12, 15, 20, 25, 50, or 100 amino acids of a FLAP polypeptide in the manufacture of antibodies, wherein said contiguous span comprises an isoleucine residue at amino acid position 127 of SEQ ID No 3. In a preferred embodiment such polypeptides are useful in the manufacture of antibodies to detect the presence and absence of the 127-Ile variant.

Non-human animals or mammals, whether wild-type or transgenic, which express a different species of FLAP than the one to which antibody binding is desired, and animals which do not express FLAP (i.e. a FLAP knock out animal as described in herein) are particularly useful for preparing antibodies. FLAP knock out animals will recognize all or most of the exposed regions of FLAP as foreign antigens, and therefore produce antibodies with a wider array of FLAP epitopes. Moreover, smaller polypeptides with only 10 to 30 amino acids may be useful in obtaining specific binding to the 127-Ile variant. In addition, the humoral immune system of animals which produce a species of FLAP that resembles the antigenic sequence will preferentially recognize the differences between the animal's native FLAP species and the antigen sequence, and produce antibodies to these unique sites in the antigen sequence. Such a technique will be particularly useful in obtaining antibodies that specifically bind to the 127-Ile variant.

XVI. Recombinant Vectors, Cell Hosts, and Transgenic Animals

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the FLAP genomic sequence, or a coding polynucleotide from the FLAP genomic sequence. Consequently, the present invention further deals with a recombinant vector comprising either a regulatory polynucleotide comprised in the nucleic acid of SEQ ID No 1 or a polynucleotide comprising the FLAP coding sequence or both.

Generally, a recombinant vector of the invention may comprise any of the polynucleotides described herein, including regulatory sequences and coding sequences, as well as any FLAP primer or probe as defined above.

In a first preferred embodiment, a recombinant vector of the invention is used to amplify the inserted polynucleotide derived from a FLAP genomic sequence of SEQ ID No 1 or a FLAP cDNA, for example the cDNA of SEQ ID No 2 in a suitable cell host, this polynucleotide being amplified at every time that the recombinant vector replicates.

A second preferred embodiment of the recombinant vectors according to the invention consists of expression vectors comprising either a regulatory polynucleotide or a coding nucleic acid of the invention, or both. Within certain embodiments, expression vectors are employed to express the FLAP polypeptide which can be then purified and, for example be used in ligand screening assays or as an immunogen in order to raise specific antibodies directed against the FLAP protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a FLAP protein, preferably the FLAP protein of the amino acid sequence of SEQ ID No 3, more preferably the FLAP protein of the amino acid sequence of SEQ ID No 3 bearing an isoleucine residues in position 127 or variants or fragments thereof, under the control of a regulatory sequence selected among the FLAP regulatory polynucleotides, or alternatively under the control of an exogenous regulatory sequence.

Consequently, preferred expression vectors of the invention are selected from the group consisting of: (a) the FLAP regulatory sequence comprised therein drives the expression of a coding polynucleotide operably linked thereto; (b) the FLAP coding sequence is operably linked to regulation sequences allowing its expression in a suitable cell host and/or host organism.

Recombinant vectors comprising a nucleic acid containing a FLAP-related biallelic marker is also part of the invention. In a preferred embodiment, said biallelic marker is selected from the group consisting of A1 to A28, and the complements thereof, or optionally the biallelic markers in linkage disequilibrium therewith. Optionally, said biallelic marker is selected from the group consisting of A1 to A13, A15, A17 to A28, and the complements thereof, or optionally the biallelic markers in linkage disequilibrium therewith.

Some of the elements which can be found in the vectors of the present invention are described in further detail in the following sections.

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The in vivo expression of a FLAP polypeptide of SEQ ID No 3 or fragments or variants thereof may be useful in order to correct a genetic defect related to the expression of the native gene in a host organism or to the production of a biologically inactive FLAP protein.

Consequently, the present invention also deals with recombinant expression vectors mainly designed for the in vivo production of the FLAP polypeptide of SEQ ID No 3 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic egineering. For example, one may refer to the book of Sambrook et al. (1989) or also to the procedures described by Fuller et al. (1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably FLAP gene regulatory polynucleotide, a polynucleotide encoding the FLAP polypeptide selected from the group consisting of SEQ ID No 1 or a fragment or a variant thereof and SEQ ID No 2, or both of them, can be utilized to transform an appropriate host to allow the expression of the desired polypeptide or polynucleotide.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4. Preferred Vectors.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising FLAP nucleotide sequences may be designed for inserting large polynucleotides of more than 40 kb (Linton et al., 1993). To generate P1 DNA for transgenic experiments, a preferred protocol is the protocol described by McCormick et al. (1994).

Baculovirus Vectors

A suitable vector for the expression of the FLAP polypeptide of SEQ ID No 6 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of the FLAP polypeptide of SEQ ID No 6 or fragments or variants thereof in a baculovirus expression system include those described by Chai et al. (1993), Vlasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application N° FR-93. 05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos. VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100-300 kb) in *E. coli*. A preferred BAC vector consists of pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediate transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application N° WO 90/11092 (Vical Inc.) and also in PCT application No WO 95/11307 (Institut Pasteur, INSERM, Université d'Ottawa) as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987)

In a specific embodiment, the invention provides a composition for the in vivo production of the FLAP protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0,1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired FLAP polypeptide or the desired fragment thereof is reintroduced into the animal body in order to deliver the recombinant protein within the body either locally or systemically.

Cell Hosts

Another object of the invention consists of a host cell that has been transformed or transfected with one of the polynucleotides described therein. Are included host cells that are transformed (prokaryotic cells) or that are transfected (eukaryotic cells) with a recombinant vector such as one of those described above.

Generally, a recombinant host cell of the invention comprises any one of the polynucleotides or the recombinant vectors described therein.

A further recombinant cell host according to the invention comprises a polynucleotide containing a biallelic marker selected from the group consisting of A1 to A28, and the complements thereof, or optionally the biallelic markers in linkage disequilibrium therewith. Optionally, said biallelic marker is selected from the group consisting of A1 to A13, A15, A17 to A28, and the complements thereof, or optionally the biallelic markers in linkage disequilibrium therewith Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like *Pseudomonas, Streptomyces* and *Staphylococcus*.

b) Eukaryotic host cells: HeLa cells (ATCC N° CCL2; N° CCL2. 1; N°CCL2. 2), Cv 1 cells (ATCC N°CCL70), COS cells (ATCC N°CRL1650; N°CRL1651), Sf-9 cells (ATCC N°CRL1711), C127 cells (ATCC N° CRL-1804), 3T3 (ATCC N° CRL-6361), CHO (ATCC N° CCL-61), human kidney 293. (ATCC N° 45504; N° CRL-1573) and BHK (ECACC N° 84100501; N° 84111301).

c) Other mammalian host cells.

The FLAP gene expression in mammalian, and typically human, cells may be rendered defective, or alternatively it may be proceeded with the insertion of a FLAP genomic or cDNA sequence with the replacement of the FLAP gene counterpart in the genome of an animal cell by a FLAP polynucleotide according to the invention. These genetic alterations may be generated by homologous recombination events using specific DNA constructs that have been previously described.

One kind of cell host that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/µl—for P1 bacteriophage inserts—in 10 mM Tris-HCl, pH 7. 4,250 µM EDTA containing 100 mM NaCl, 30 µM spermine, and70 µM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC n° CRL-1821), ES-D3 (ATCC n° CRL1934 and n° CRL-11632),YS001 (ATCC n° CRL-11776), 36. 5 (ATCC n° CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells consist of primary embryonic fibroblasts that are established from tissue of day 13 to day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a FLAP gene disrupted by homologous recombination with a knock out vector.

The transgenic animals of the invention all include within a plurality of their cells a cloned recombinant or synthetic DNA sequence, more specifically one of the purified or isolated nucleic acids comprising a FLAP coding sequence, a FLAP regulatory polynucleotide or a DNA sequence encoding an antisense polynucleotide such as described in the present specification.

Generally, a transgenic animal according the present invention comprises any one of the polynucleotides, the recombinant vectors and the cell hosts described in the present invention.

A further transgenic animal according to the invention contains in their somatic cells and/or in their germ line cells a polynucleotide comprising a biallelic marker selected from the group consisting of A1 to A28, and the complements thereof, or optionally the biallelic markers in linkage disequilibrium therewith. Optionally said biallelic marker is selected from the group consisting of A1 to A13, A15, A17 to A28, and the complements thereof, or optionally the biallelic markers in linkage disequilibrium therewith.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native FLAP protein, or alternatively a mutant FLAP protein.

In a second preferred embodiment, these transgenic animals may express a desired polypeptide of interest under the control of the regulatory polynucleotides of the FLAP gene, leading to good yields in the synthesis of this protein of interest, and eventually a tissue specific expression of this protein of interest.

The design of the transgenic animals, including knock out animals, of the invention may be made according to the conventional techniques well known from the one skilled in the art. For more details regarding the production of transgenic animals, and specifically transgenic mice, it may be referred to U.S. Pat. Nos. 4,873,191, issued Oct. 10, 1989, 5,464,764 issued Nov. 7, 1995; 5,789,215, issued Aug. 4, 1998; Capecchi, M. R. (1989a); Capecchi, M. R. (1989b); and Tsuzuki, T. and Rancourt, D. E. (1998), these documents being hereby incorporated by reference.

The present invention encompasses knock out vectors comprising the novel polynucleotides of the invention, as well as mammalian host cells and non-human host mammals comprising a FLAP gene disrupted by homologous recombination with such a knock out vector Transgenic animals of the present invention are produced by the application of procedures which result in an animal with a genome that has incorporated exogenous genetic material. The procedure involves obtaining the genetic material, or a portion thereof, which encodes either a FLAP coding sequence, a FLAP regulatory polynucleotide or a DNA sequence encoding a FLAP antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein.

In one embodiment the invention encompasses cells derived from non-human host mammals and animals comprising a recombinant vector of the invention or a FLAP gene disrupted by homologous recombination with a knock out vector.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989) and Shay et al. (1991).

XVII. Screening of Agents Acting on the Leukotriene Pathway

In a further embodiment, the present invention also concerns a method for the screening of new agents, or candidate substances, acting on the leukotriene pathway and which may be suitable for the treatment of a patient whose DNA comprises an allele of the FLAP gene associated with a disease involving the leukotriene pathway, more particularly asthma.

In a preferred embodiment, the invention relates to a method for the screening of candidate substances for their ability to alter leukotriene biosynthesis, preferably to identify active candidate substances without undesired side-effects such as increased liver transaminase levels. The method comprises the following steps: a) providing a cell line, an organ, or a mammal expressing 5-LO and either a FLAP gene comprising alleles for one or more FLAP-related biallelic markers, preferably associated with a modified leukotriene pathway, more preferably with a disease involving the leukotriene pathway such as asthma, or a mutated FLAP gene comprising the trait cause mutation determined using the above-noted method; b) obtaining a candidate substance; and, c) testing the ability of the candidate substance to modify leukotriene biosynthesis, and particularly to interact with the 5-LO and/or with the FLAP produced by the cell line or the transgenic mammal and/or to modify the interaction between 5-LO and FLAP and/or to modulate the expression levels of FLAP.

In one embodiment of the above method, the method comprises providing a cell line, an organ, or a mammal expressing 5-LO, a FLAP gene comprising alleles for one or more FLAP-related biallelic markers, preferably associated with a modified leukotriene pathway, more preferably with a disease involving the leukotriene pathway such as asthma, and a mutated FLAP gene comprising the trait cause mutation determined using the above-noted method. Said biallelic markers may be selected from the group consisting of A1 to A28, and the complements thereof; Optionally, said FLAP-related biallelic marker may be selected from the group consisting of A1 to A13, A15, and A17 to A28, and the complements thereof, or optionally the biallelic markers in linkage disequilibrium therewith; optionally, said biallelic markers are selected from the group consisting of A1 to A10 and A22 to A28, and the complements thereof, or optionally the biallelic markers in linkage disequilibrium therewith; optionally, said biallelic markers are selected from the group consisting of A11 to A13, A15, A17 to A21, and the complements thereof, or optionally the biallelic markers in linkage disequilibrium therewith; optionally, said biallelic markers are selected from the group consisting of A14 or A16, and the complements thereof, or optionally the biallelic markers in linkage disequilibrium therewith. In a preferred embodiment, said biallelic markers are selected from the group consisting of A2, A14, A16, A18, A19, A22, and A23, and the complements thereof, or optionally the biallelic markers in linkage disequilibrium therewith. In another preferred embodiment said biallelic markers are selected from the group consisting of A14 and A19, and the complements thereof, or optionally the biallelic markers in linkage disequilibrium therewith. In more preferred embodiment, said biallelic markers comprise the biallelic marker A19, and the complement thereof, or optionally the biallelic markers in linkage disequilibrium therewith.

A candidate substance is a substance which can interact with or modulate, by binding or other intramolecular interactions, 5-LO or FLAP. Such substances may be potentially interesting for patients who are not responsive to existing drugs. Screening may be effected using either in vitro methods or in vivo methods.

In vitro methods can be carried out in numerous ways such as on transformed cells which express the considered alleles of the FLAP gene through 5-lipoxygenase activation and leukotriene synthesis measurement or on FLAP encoded by the considered allelic variant of FLAP through FLAP binding assays.

Screening assays of the present invention generally involve determining the ability of a candidate substance to affect the activity of 5-LO or FLAP, such as the screening of candidate substances to identify those that inhibit or otherwise modify the function of 5-LO or FLAP in the leukotriene pathway.

One method of drug screening utilizes eukaryotic host cells which are stably transformed with recombinant polynucleotides expressing 5-LO and the considered alleles of the FLAP gene. Such cells, either in viable or fixed form, can be used for standard binding assays. One can measure, for example, the formation of products of the leukotriene pathway such as $LTB_4$ synthesis or examine the degree to which the formation of such products is interfered with by the agent being tested.

Typically, this method includes preparing transformed cells which express 5-LO and different forms of FLAP encoded by DNA sequences containing particular alleles of one or more of the biallelic markers and/or mutations described above. This is followed by testing the cells expressing the 5-LO and FLAP with a candidate substance to determine the ability of the substance to affect the leukotriene pathway function, in order to identify those which affect the enzymatic activity of 5-LO or the activity of FLAP, and which thus can be suitable for use in humans.

Typical examples of such drug screening assays are provided below. It is to be understood that the parameters set forth in these examples can be modified by the skilled person without undue experimentation.

Screening for 5-LO Inhibitors

Drug effects can be evaluated by assessing the 5-LO products generated by cells expressing both the 5-LO gene and the considered allele of the FLAP gene. Eukaryotic cells previously transformed with appropriate vectors as described previously and expressing 5-LO and the allele of the FLAP gene under study are harvested by centrifugation (300 g, 5 min, and room temperature) and washed with an appropriate buffer. The cells are then resuspended in buffer, pre-warmed at 37° C., preferably at a cell density of $5 \times 10^6$ cells/ml. Aliquots of the cell suspension are incubated with the considered drug for preferably 5 min at 37° C. Reaction is initiated by the addition of calcium ionophore A23187 and arachidonic acid. Following incubation at 37° C., reaction is stopped by adding methanol containing prostaglandin B2 as an internal standard for HPLC analysis. 5-LO reaction products are extracted into chloroform, dried under a stream of nitrogen, and resuspended in HPLC solvent. The samples are analyzed by reverse-phase HPLC using preferably an isocratic solvent system of methanol/water/acetic acid (75:25:0.01). The elution is monitored at preferably 270 and 234 nm. 5-LO products are quantitated by comparison of peak areas to those of standard curves of authentic standards, and corrected for minor differences in extraction efficiency determined using the prostaglandin B2 internal standard. This method is described in more detail in Dixon et al. (1990) and Abramovitz et al. (1993), the disclosures of which are incorporated herein by reference.

Screening for FLAP Inhibitors

The FLAP protein or portions thereof described above may be used in drug screening procedures to identify molecules which are agonists, antagonists, or inhibitors of FLAP activity. The FLAP protein or portion thereof used in such analyses may be free in solution or linked to a solid support. Alternatively, FLAP protein or portions thereof can be expressed on a cell surface. The cell may naturally express the FLAP protein or portion thereof or, Alternatively, the cell may express the FLAP protein or portion thereof from an expression vector such as those described above.

In one method of drug screening, eucaryotic or procaryotic host cells which are stably transformed with recombinant polynucleotides in order to express the FLAP protein or a portion thereof are used in conventional competitive binding assays or standard direct binding assays. For example, the formation of a complex between the FLAP protein or a portion thereof and the agent being tested may be measured in direct binding assays. Alternatively, the ability of a test agent to prevent formation of a complex between the FLAP protein or a portion thereof and a known ligand may be measured.

For example, a FLAP inhibitor binding assay can be based on the observation that MK-886, an indole leukotriene biosynthesis inhibitor, binds with high affinity and specificity to FLAP. Binding of the considered drug to FLAP can be assessed by a competition experiments with a radiolabeled analog of MK-886, $^{125}$I-L-691-831. A suspension of cells expressing the considered allele of FLAP containing preferably $2 \, 10^7$ cells is centrifuged at 500×g for 10 min. The pelleted cells are then resuspended in lysis buffer. This suspension is sonicated on ice by three 20 sec bursts. Cell lysis is checked visually. Binding is initiated by addition of cell lysis samples to wells containing $^{125}$I-L-691-831 and either the considered drug or nothing (control). The plate is incubated for 20 min at room temperature. The samples are then filtered and washed. Bound $^{125}$I-L-691-831 is determined in a counter. Specific drug binding is defined as the difference between binding in the absence and the presence of the considered drug. This FLAP binding assay is described with more details in Charleson et al. (1992).

Alternatively, the high throughput screening techniques disclosed in published PCT application WO 84/03564 may be used. In such techniques, large numbers of small peptides to be tested for FLAP binding activity are synthesized on a surface and affixed thereto. The test peptides are contacted with the FLAP protein or a portion thereof, followed by a wash step. The amount of FLAP protein or portion thereof which binds to the test compound is quantitated using conventional techniques.

In some methods, FLAP protein or a portion thereof may be fixed to a surface and contacted with a test compound. After a washing step, the amount of test compound which binds to the FLAP protein or portion thereof is measured.

Screening for Inhibitors of the Interaction between 5-LO and FLAP

Drug effects can be evaluated through the assessment of the interaction between 5-LO and FLAP proteins.

Interaction between 5-LO and FLAP protein may be assessed using two hybrid systems such as the Matchmaker Two Hybrid System 2 (Catalog No K1604-1, Clontech). As described in the manual accompanying the Matchmaker Two Hybrid System 2 (Catalog No K1604-1, Clontech) nucleic acids encoding the FLAP protein or a portion thereof, are inserted into an expression vector such that they are in frame with DNA encoding the DNA binding domain of the yeast transcriptional activator GAL4. 5-LO cDNA or a portion thereof is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between FLAP and 5-LO proteins.

In another method, affinity columns containing the FLAP protein or a portion thereof can be constructed. In some versions of this method the affinity column contains chimeric proteins in which the FLAP protein or a portion thereof is fused to glutathione S-transferase. 5-LO protein is applied to the affinity column. The 5-LO protein retained on the affinity column can be measured and can allow assessment of the interaction between FLAP and 5-LO proteins.

Association between 5-LO and FLAP proteins can also be assessed by using an Optical Biosensor as described in Edwards et Leatherbarrow, (1997). The main advantage of the method is that it allows the determination of the association rate. Typically a FLAP molecule is linked to the sensor surface (through a carboxymethl dextran matrix) and a sample of 5-LO molecules is placed in contact with the FLAP molecules. The binding of a 5-LO molecule to the FLAP molecule causes a change in the refractive index and/or thickness. This change is detected by the Biosensor provided it occurs in the evanescent field (which extend a few hundred nanometers from the sensor surface). Hence, the effect of candidate drug on the association between FLAP and 5-LO proteins can be easily measured.

Screening for Expression Modifiers

The screening of expression modifiers is important as it can be used for detecting modifiers specific to one allele or a group of alleles of the FLAP gene. The alteration of FLAP expression in response to a modifier can be determined by administering or combining the candidate modifier with an expression system such as animal, or cell, and in in vitro transcription assay.

The effect of the modifier on FLAP transcription and/or steady state mRNA levels can also be determined. As with the basic expression levels, tissue specific interactions are of interest. Correlations are made between the ability of an expression modifier to affect FLAP activity, and the presence of the targeted polymorphisms. A panel of different modifiers may be screened in order to determine the effect under a number of different conditions.

Expression levels and patterns of FLAP may be analyzed by solution hybridization with long probes as described in International Patent Application No WO 97/05277, the entire contents of which are incorporated herein by reference. Briefly, the FLAP cDNA or the FLAP genomic DNA described above, or fragments thereof, is inserted at a cloning site immediately downstream of a bacteriophage (T3, T7 or SP6) RNA polymerase promoter to produce antisense RNA. Preferably, the FLAP insert comprises at least 100 or more consecutive nucleotides of the genomic DNA sequence or the cDNA sequences, particularly those comprising at least one of the biallelic markers of the present invention or those encoding mutated FLAP. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of FLAP gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the FLAP genomic DNA, the FLAP cDNA sequences or the sequences complementary thereto or fragments thereof, particularly those comprising at least one of the biallelic markers of the present invention or those encoding mutated FLAP. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of FLAP gene expression may be performed with a complementary DNA microarray as described by Schena et al. (1995 and 1996). Full length FLAP cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of FLAP gene expression may also be performed with full length FLAP cDNAs or fragments thereof in complementary DNA arrays as described by Pietu et al. (1996). The full length FLAP cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the FLAP genomic DNA, the FLAP cDNA, or fragments thereof can be done through high density nucleotide arrays as described by Lockhart et al. (1996) and Sosnowsky et al. (1997). Oligonucleotides of 15-50 nucleotides from the sequences of the FLAP genomic DNA, the FLAP cDNA sequences, particularly those comprising at least one of the biallelic markers of the present invention or those encoding mutated FLAP, or the sequences complementary thereto, are synthesized directly on the chip (Lockhart et al., 1996) or synthesized and then addressed to the chip (Sosnowsky et al., 1997). Preferably, the oligonucleotides are about 20 nucleotides in length.

FLAP cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997), the dyes or labeling compounds are detected and quantified. Duplicate hybridizations are performed. Comparative analysis of the intensity of the signal originating from cDNA probes on the same target oligonucleotide in different cDNA samples indicates a differential expression of FLAP mRNA.

Screening using Transgenic Animals

In vivo methods can utilize transgenic animals for drug screening. Nucleic acids including at least one of the biallelic polymorphisms of interest can be used to generate genetically modified non-human animals or to generate site specific gene modifications in cell lines. The term "transgenic" is intended to encompass genetically modified animals having a deletion or other knock-out of FLAP gene activity, having an exogenous FLAP gene that is stably transmitted in the host cells, or having an exogenous FLAP promoter operably linked to a reporter gene. Transgenic animals may be made through homologous recombination, where the FLAP locus is altered. Alternatively, a nucleic acid construct is randomly integrated into the genome. Vectors for stable integration include for example plasmids, retroviruses and other animal viruses, and YACs. Of interest are transgenic mammals e.g. cows, pigs, goats, horses, and particularly rodents such as rats and mice. Transgenic animals allow to study both efficacy and toxicity of the candidate drug.

XVIII. Computer-Related Embodiments

As used herein the term "nucleic acid codes of the invention" encompass the nucleotide sequences comprising, consisting essentially of, or consisting of any one of the following: a) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises at least 1 of the following nucleotide positions of SEQ ID No 1: 1-7007, 8117-15994, 16550-24058, 24598-27872, 28413-35976, and 36927-43069; b) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises a C at position 16348 of SEQ ID No 1; c) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises the following nucleotide positions of SEQ ID No 1: 7612-7637, 24060-24061, 24067-24068, 27903-27905, and 28327-28329; d) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises a nucleotide selected from the group consisting of an A at position 7445, an A at position 7870, a T at position 16288, an A at position 16383, a T at position 24361, a G at position 28336, a T at position 28368, an A at position 36183, and a G at position 36509 of SEQ ID No 1; e) a contiguous span of at least 12, 15, 18, 20, 25, 30, 35, 40, 50, 60, 70, 80, 90, 100, 150, 200, 500, or 1000 nucleotides of SEQ ID No 2, wherein said contiguous span comprises a T at position 197, an A at position 453, or a G at position 779 of SEQ ID No 2; and f) a nucleotide sequence complementary to any one of the preceding nucleotide sequences.

The "nucleic acid codes of the invention" further encompass nucleotide sequences homologous to a contiguous span of at least 30, 35, 40, 50, 60, 70, 80, 90, 100, 150, 200, 500, or 1000 nucleotides of the following nucleotide position range: 1-7007, 8117-15994, 16550-24058, 24598-27872, 28413-35976, and 36927-43069 of SEQ ID No 1, and sequences complementary to all of the preceding sequences. Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, 3$^{rd}$ edition. W. H Freeman & Co., New York.) or in any other format or code which records the identity of the nucleotides in a sequence.

As used herein the term "polypeptide codes of the invention" encompass the polypeptide sequences comprising a contiguous span of at least 6, 8, 10, 12, 15, 20, 25, 30, 40, 50, or 100 amino acids of SEQ ID No 3, wherein said contiguous span includes an isoleucine residue at amino acid position 127 of SEQ ID No 3. It will be appreciated that the polypeptide codes of the invention can be represented in the traditional single character format or three letter format (See the inside back cover of Stryer, Lubert. *Biochemistry*, 3$^{rd}$ edition. W. H Freeman & Co., New York.) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the sequence information described herein. As used herein, "a computer system" refers to the hardware components, software components, and data storage components used to store and/or analyze the nucleotide sequences of the nucleic acid codes of the invention, the amino acid sequences of the polypeptide codes of the invention, or other sequences. The computer system preferably includes the computer readable media described above, and a processor for accessing and manipulating the sequence data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acid codes of the invention, or the amino acid sequences of the polypeptide codes of the invention (such as search tools, compare tools, modeling tools, etc.) may reside in main memory during execution.

In some embodiments, the computer system may further comprise a sequence comparer for comparing the nucleic acid codes of the invention or polypeptide codes of the invention stored on a computer readable medium to reference nucleotide or polypeptide sequences stored on a computer readable medium. A "sequence comparer" refers to one or more programs which are implemented on the computer system to compare a nucleotide or polypeptide sequence with other nucleotide or polypeptide sequences and/or compounds including but not limited to peptides, peptidomimetics, and chemicals the sequences or structures of which are stored within the data storage means. For example, the sequence comparer may compare the nucleotide sequences of the nucleic acid codes of the invention, or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above.

The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, 1990), FASTA (Pearson and Lipman, 1988), FASTDB (Brutlag et al., 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Throughout this application, various publications, patents, and published patent applications are cited. The disclosures of the publications, patents, and published patent specifications referenced in this application are hereby incorporated by reference into the present disclosure to more fully describe the state of the art to which this invention pertains.

EXAMPLES

Example 1

Detection of FLAP Biallelic Markers: DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM MgCl$_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
- 3 ml TE 10-2 (Tris-HCl 10 mM, EDTA 2 mM)/NaCl 0.4 M;
- 200 µl SDS 10%; and
- 500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Detection of the Biallelic Markers: Amplification of Genomic DNA by PCR

The amplification of specific genomic sequences of the DNA samples of example 1 was carried out on the pool of DNA obtained previously. In addition, 50 individual samples were similarly amplified.

PCR assays were performed using the following protocol:

| | |
|---|---|
| Final volume | 25 µl |
| DNA | 2 ng/µl |
| MgCl$_2$ | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M Tris-HCl pH8.3 0.5M KCl) | 1x |

Each pair of first primers was designed using the sequence information of the FLAP gene (GenBank 182657, Kennedy et al. 1991 incorporated herein by reference) and the OSP software (Hillier & Green, 1991). These first primers had about 20 nucleotides in length and their respective sequences are disclosed in Table 1.

TABLE 1

| Amplicon | Position range of the amplicon in SEQ ID No 1 | | PU | Position range of amplification primer in SEQ ID No 1 | | RP | Complementary position range of amplification primer in SEQ ID No 1 | |
|---|---|---|---|---|---|---|---|---|
| 10-517 | 3851 | 4189 | B15 | 3851 | 3869 | C15 | 4171 | 4189 |
| 10-518 | 4120 | 4390 | B16 | 4120 | 4138 | C16 | 4372 | 4390 |
| 10-253 | 4373 | 4792 | B1 | 4373 | 4391 | C1 | 4773 | 4792 |
| 10-499 | 4814 | 5043 | B2 | 4814 | 4833 | C2 | 5026 | 5043 |
| 10-500 | 4956 | 5422 | B3 | 4956 | 4972 | C3 | 5405 | 5422 |
| 10-522 | 5524 | 5996 | B17 | 5524 | 5542 | C17 | 5978 | 5996 |
| 10-503 | 6218 | 6672 | B4 | 6218 | 6235 | C4 | 6652 | 6672 |
| 10-504 | 6522 | 6790 | B5 | 6522 | 6539 | C5 | 6772 | 6790 |
| 10-204 | 7120 | 7574 | B6 | 7120 | 7137 | C6 | 7557 | 7574 |
| 10-32 | 7513 | 7933 | B7 | 7513 | 7531 | C7 | 7914 | 7933 |
| 10-33 | 16114 | 16533 | B8 | 16114 | 16132 | C8 | 16515 | 16533 |
| 10-34 | 24072 | 24425 | B9 | 24072 | 24089 | C9 | 24408 | 24425 |
| 10-35 | 27978 | 28401 | B10 | 27978 | 27995 | C10 | 28384 | 28401 |
| 10-36 | 36020 | 36465 | B11 | 36020 | 36039 | C11 | 36446 | 36465 |
| 10-498 | 36318 | 36669 | B12 | 36318 | 36337 | C12 | 36652 | 36669 |
| 12-629 | 38441 | 38840 | B13 | 38441 | 38460 | C13 | 38820 | 38840 |
| 12-628 | 42233 | 42749 | B14 | 42233 | 42253 | C14 | 42731 | 42749 |

Preferably, the primers contained a common oligonucleotide tail upstream of the specific bases targeted for amplification which was useful for sequencing.

PU Amplification Primers contain the following additional PU 5' sequence: TGTAAAACGACGGCCAGT (SEQ ID No 14); RP amplification primers contain the following RP 5' sequence: CAGGAAACAGCTATGACC (SEQ ID No 15).

The synthesis of these primers was performed following the phosphoramidite method, on a GENSET UFPS 24.1 synthesizer.

DNA amplification was performed on a Genius II thermocycler. After heating at 94° C. for 10 min, 40 cycles were performed. Each cycle comprised: 30 sec at 94° C., 55° C. for 1 min, and 30 sec at 72° C. For final elongation, 7 min at 72° C. end the amplification. The quantities of the amplification products obtained were determined on 96-well microtiter plates, using a fluorometer and Picogreen as intercalant agent (Molecular Probes).

Example 3

Detection of the Biallelic Markers:

Seguencing of Amplified Genomic DNA and Identification of Polymorphisms

The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined.

The sequence data were further evaluated for polymorphisms by detecting the presence of biallelic markers among the pooled amplified fragments. The polymorphism search was based on the presence of superimposed peaks in the electrophoresis pattern resulting from different bases occurring at the same position.

17 fragments of amplification were analyzed. In these segments, 28 biallelic markers were detected. The localization of the biallelic markers was as shown in Table 2.

TABLE 2

| Amplicon | BM | Marker Name | Freq. of all2 | Localization in FLAP gene | Polymorphism | | BM position in SEQ ID | | Position of 47 mers in SEQ ID No 1 | | 47 mers name |
|---|---|---|---|---|---|---|---|---|---|---|---|
| | | | | | all1 | all2 | No 1 | No 2 | | | |
| 10-517 | A25 | 10-517-100 | | 5'regulatory | G | C | 3950 | | 3927 | 3973 | P25 |
| 10-518 | A26 | 10-518-125 | | 5'regulatory | G | T | 4243 | | 4220 | 4266 | P26 |
| 10-518 | A27 | 10-518-194 | | 5'regulatory | A | G | 4312 | | 4289 | 4335 | P27 |
| 10-253 | A1 | 10-253-118 | | 5'regulatory | A | G | 4490 | | 4467 | 4513 | P1 |
| 10-253 | A2 | 10-253-298 | 4.57 | 5'regulatory | G | C | 4670 | | 4647 | 4693 | P2 |
| 10-253 | A3 | 10-253-315 | | 5'regulatory | C | T | 4687 | | 4664 | 4710 | P3 |
| 10-499 | A4 | 10-499-155 | | 5'regulatory | A | G | 4968 | | 4945 | 4991 | P4 |
| 10-500 | A5 | 10-500-185 | | 5'regulatory | C | T | 5140 | | 5117 | 5163 | P5 |
| 10-500 | A6 | 10-500-258 | | 5'regulatory | G | T | 5213 | | 5190 | 5236 | P6 |
| 10-500 | A7 | 10-500-410 | | 5'regulatory | A | G | 5364 | | 5341 | 5387 | P7 |
| 10-522 | A28 | 10-522-71 | | 5'regulatory | A | G | 5594 | | 5571 | 5617 | P28 |
| 10-503 | A8 | 10-503-159 | | 5'regulatory | G | T | 6370 | | 6347 | 6393 | P8 |
| 10-504 | A9 | 10-504-172 | | 5'regulatory | A | T | 6693 | | 6670 | 6716 | P9 |
| 10-504 | A10 | 10-504-243 | | 5'regulatory | A | C | 6763 | | 6740 | 6786 | P10 |

TABLE 2-continued

| Amplicon | BM | Marker Name | Freq. of all2 | Localization in FLAP gene | Polymorphism all1 | Polymorphism all2 | BM position in SEQ ID No 1 | BM position in SEQ ID No 2 | Position of 47 mers in SEQ ID No 1 | | 47 mers name |
|---|---|---|---|---|---|---|---|---|---|---|---|
| 10-204 | A11 | 10-204-326 | 6.63 | 5'regulatory | A | G | 7445 | | 7422 | 7468 | P11 |
| 10-32 | A12 | 10-32-357 | 33.45 | Intron 1 | A | C | 7870 | | 7847 | 7893 | P12 |
| 10-33 | A13 | 10-33-175 | 2.3 | Exon 2 | C | T | 16288 | 197 | 16265 | 16311 | P13 |
| 10-33 | A14 | 10-33-234 | 43.98 | Intron 2 | A | C | 16347 | | 16324 | 16370 | P14 |
| 10-33 | A15 | 10-33-270 | | Intron 2 | A | G | 16383 | | 16360 | 16406 | P15 |
| 10-33 | A16 | 10-33-327 | 24.26 | Intron 2 | C | T | 16440 | | 16417 | 16463 | P16 |
| 10-34 | A17 | 10-34-290 | | Intron 3 | G | T | 24361 | | 24338 | 24384 | P17 |
| 10-35 | A18 | 10-35-358 | 31.25 | Intron 4 | G | C | 28336 | | 28313 | 28359 | P18 |
| 10-35 | A19 | 10-35-390 | 22.98 | Intron 4 | C | T | 28368 | | 28345 | 28391 | P19 |
| 10-36 | A20 | 10-36-164 | | Exon 5 V127→I | A | G | 36183 | 453 | 36160 | 36206 | P20 |
| 10-498 | A21 | 10-498-192 | | Exon 5 | A | G | 36509 | 779 | 36486 | 36532 | P21 |
| 12-629 | A22 | 12-629-241 | 28.3 | 3'regulatory | G | C | 38681 | | 38658 | 38704 | P22 |
| 12-628 | A24 | 12-628-311 | | 3'regulatory | T | C | 42440 | | 42417 | 42463 | P24 |
| 12-628 | A23 | 12-628-306 | 10.27 | 3'regulatory | G | A | 42445 | | 42422 | 42468 | P23 |

BM refers to "biallelic marker". All1 and all2 refer respectively to allele 1 and allele 2 of the biallelic marker. "Freq. Of all2" refers to the frequency of the allele 2 in percentage in Caucasian US control population, except for the biallelic marker 10-204/326 for which the population is the French Caucasian controls. Frequencies corresponded to a population of random blood donors from French Caucasian origin.

The polymorphisms A14 (10-33-234) and A16 (10-33-327) have been observed in Kennedy et al, 1991. However, their frequencies in the population was unknown, therefore they can not be considered validated biallelic markers, until the results of the present inventors were obtained.

Example 4

Validation of the Polymorphisms through Microsequencing

The biallelic markers identified in example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers (Table 1).

The preferred primers used in microsequencing had about 19 nucleotides in length and hybridized just upstream of the considered polymorphic base. Their sequences are disclosed in Table 3 below.

TABLE 3

| Marker Name | Biallelic Marker | Mis. 1 | Position range of microsequencing primer mis 1 in SEQ ID No 1 | | Mis. 2 | Complementary position range of misrosequencing primer mis. 2 in SEQ ID No 1 | |
|---|---|---|---|---|---|---|---|
| 10-517-100 | A25 | D25 | 3930 | 3949 | E25 | 3951 | 3970 |
| 10-518-125 | A26 | D26 | 4223 | 4242 | E26 | 4244 | 4263 |
| 10-518-194 | A27 | D27 | 4292 | 4311 | E27 | 4313 | 4332 |
| 10-253-118 | A1 | D1 | 4470 | 4489 | E1 | 4491 | 4510 |
| 10-253-298 | A2 | D2 | 4650 | 4669 | E2 | 4671 | 4690 |
| 10-253-315 | A3 | D3 | 4667 | 4686 | E3 | 4688 | 4707 |
| 10-499-155 | A4 | D4 | 4948 | 4967 | E4 | 4969 | 4988 |
| 10-500-185 | A5 | D5 | 5120 | 5139 | E5 | 5141 | 5160 |
| 10-500-258 | A6 | D6 | 5193 | 5212 | E6 | 5214 | 5233 |
| 10-500-410 | A7 | D7 | 5344 | 5363 | E7 | 5365 | 5384 |
| 10-522-71 | A28 | D28 | 5574 | 5593 | E28 | 5595 | 5614 |
| 10-503-159 | A8 | D8 | 6350 | 6369 | E8 | 6371 | 6390 |
| 10-504-172 | A9 | D9 | 6673 | 6692 | E9 | 6694 | 6713 |
| 10-504-243 | A10 | D10 | 6743 | 6762 | E10 | 6764 | 6783 |
| 10-204-326 | A11 | D11 | 7425 | 7444 | E11 | 7446 | 7465 |
| 10-32-357 | A12 | D12 | 7850 | 7869 | E12 | 7871 | 7890 |
| 10-33-175 | A13 | D13 | 16268 | 16287 | E13 | 16289 | 16308 |
| 10-33-234 | A14 | D14 | 16327 | 16346 | E14 | 16348 | 16367 |
| 10-33-270 | A15 | D15 | 16363 | 16382 | E15 | 16384 | 16403 |
| 10-33-327 | A16 | D16 | 16420 | 16439 | E16 | 16441 | 16460 |
| 10-34-290 | A17 | D17 | 24341 | 24360 | E17 | 24362 | 24381 |
| 10-35-358 | A18 | D18 | 28316 | 28335 | E18 | 28337 | 28356 |
| 10-35-390 | A19 | D19 | 28348 | 28367 | E19 | 28369 | 28388 |
| 10-36-164 | A20 | D20 | 36163 | 36182 | E20 | 36184 | 36203 |
| 10-498-192 | A21 | D21 | 36489 | 36508 | E21 | 36510 | 36529 |

TABLE 3-continued

| Marker Name | Biallelic Marker | Mis. 1 | Position range of microsequencing primer mis 1 in SEQ ID No 1 | | Mis. 2 | Complementary position range of misrosequencing primer mis. 2 in SEQ ID No 1 | |
|---|---|---|---|---|---|---|---|
| 12-629-241 | A22 | D22 | 38661 | 38680 | E22 | 38682 | 38701 |
| 12-628-311 | A24 | D24 | 42420 | 42439 | E24 | 42441 | 42460 |
| 12-628-306 | A23 | D23 | 42425 | 42444 | E23 | 42446 | 42465 |

Mis 1 and Mis 2 respectively refer to microsequencing primers which hybridized with the non-coding strand of the FLAP gene or with the coding strand of the FLAP gene.

The microsequencing reaction was performed as follows:

5 µl of PCR products were added to 5 µl purification mix 2U SAP (Shrimp alkaline phosphate) (Amersham E70092X)); 2U Exonuclease I (Amersham E70073Z); 1 µl SAP buffer (200 mM Tris-HCl pH8, 100 mM $MgCl_2$) in a microtiter plate. The reaction mixture was incubated 30 minutes at 37° C., and denatured 10 minutes at 94° C. afterwards. To each well was then added 20 µl of microsequencing reaction mixture containing: 10 pmol microsequencing oligonucleotide (19 mers, GENSET, crude synthesis, 5 OD), 1 U Thermosequenase (Amersham E79000G), 1.25 µl Thermosequenase buffer (260 mM Tris HCl pH 9.5, 65 mM $MgCl_2$), and the two appropriate fluorescent ddNTPs complementary to the nucleotides at the polymorphic site corresponding to both polymorphic bases (11.25 nM TAMRA-ddTTP; 16.25 nM ROX-ddCTP; 1.675 nM REG-ddATP; 1.25 nM RHO-ddGTP; Perkin Elmer, Dye Terminator Set 401095). After 4 minutes at 94° C., 20 PCR cycles of 15 sec at 55° C., 5 sec at 72° C., and 10 sec at 94° C. were carried out in a Tetrad PTC-225 thermocycler (MJ Research). The microtiter plate was centrifuged 10 sec at 1500 rpm. The unincorporated dye terminators were removed by precipitation with 19 µl $MgCl_2$ 2 mM and 55 µl 100% ethanol. After 15 minute incubation at room temperature, the microplate was centrifuged at 3300 rpm 15 minutes at 4° C. After discarding the supernatants, the microplate was evaporated to dryness under reduced pressure (Speed Vac); samples were resuspended in 2.5 µl formamide EDTA loading buffer and heated for 2 min at 95° C. 0.8 µl microsequencing reaction were loaded on a 10% (19:1) polyacrylamide sequencing gel. The data were collected by an ABI PRISM 377 DNA sequencer and processed using the GENESCAN software (Perkin Elmer).

Example 5

Association Study between Asthma and the Biallelic Markers of the FLAP Gene: Collection of DNA Samples from Affected and Non-affected Individuals The disease trait followed in this association study was asthma, a disease involving the leukotriene pathway.

The asthmatic population corresponded to 297 individuals that took part in a clinical study for the evaluation of the anti-asthmatic drug Zileuton. More than 90% of these 297 asthmatic individuals had a Caucasian ethnic background.

The control population corresponded to unaffected individuals. In this association study, either Caucasian French population (190 individuals) or Caucasian US population (286 individuals) is used as control population. The preferred control population is the Caucasian US population since the asthmatic population essentially comprises US individuals.

Example 6

Association Study between Asthma and the Biallelic Markers of the FLAP Gene:

Genotyping of Affected and Control Individuals

The general strategy to perform the association studies was to individually scan the DNA samples from all individuals in each of the populations described above in order to establish the allele frequencies of the above described biallelic markers in each of these populations.

Allelic frequencies of the above-described biallelic markers in each population were determined by performing microsequencing reactions on amplified fragments obtained by genomic PCR performed on the DNA samples from each individual. Genomic PCR and microsequencing were performed as detailed above in examples 2 and 4 using the described PCR and microsequencing primers.

Example 7

Association Study between Asthma and the Biallelic Markers of the FLAP Gene

A) Association Studies for Asthma Gene with Caucasian French Control Population

This association study uses 293 asthmatic individuals and 185 Caucasian French controls.

Figure 2:
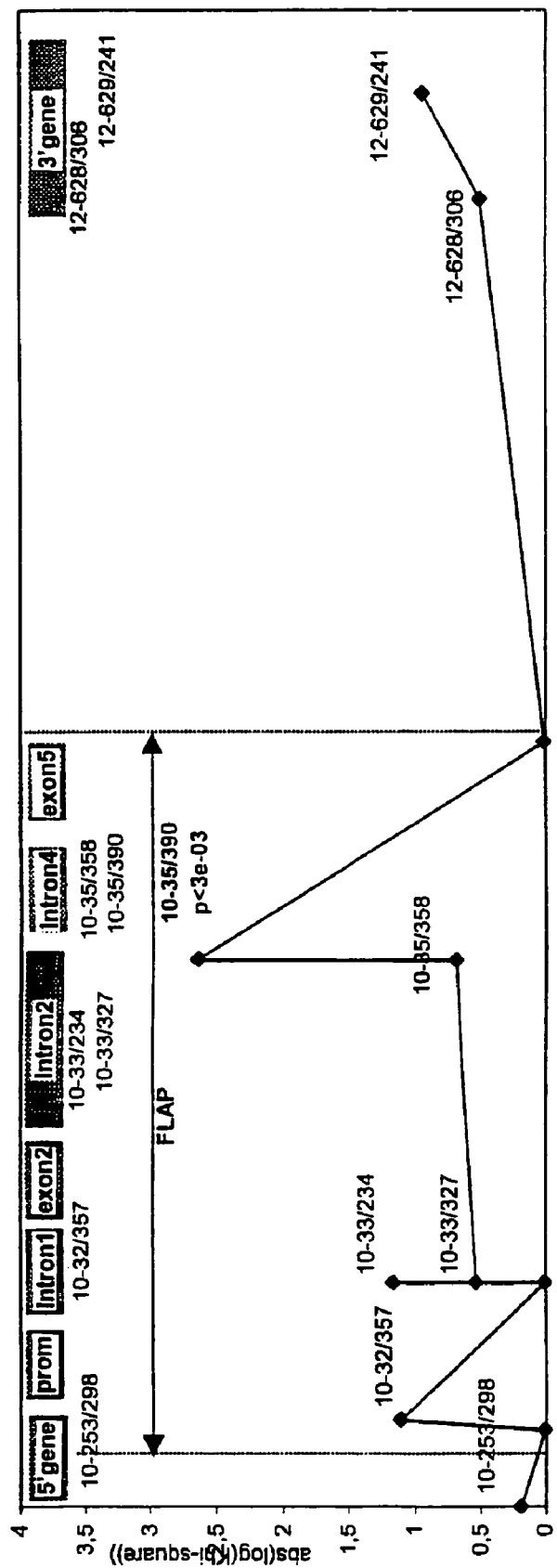
FIG. 2 show the results of an association study between the FLAP biallelic markers and asthma with 290 asthmatic individuals and 280 US Caucasian controls.

As shown in FIG. 2(A), markers 10-32/357 and 10-35/390 presented a strong association with asthma, this association being highly significant (pvalue=$1.95 \times 10^{-3}$ for marker 10-32/357 and $1.75 \times 10^{-3}$ for marker 10-35/390). The two markers 10-32/357 and 10-35/390 can be then used in diagnostics with a test based on each marker. Two other markers showed moderate association when tested independently, namely 33/234, and 35/358.

B) Association Studies for Asthma Gene with Caucasian US Control Population

This association study uses 297 asthmatic individuals and 286 Caucasian US controls.

As shown in FIG. 2(B), the biallelic marker 10-35/390 presented a strong association with asthma, this association being highly significant (pvalue=$2.29 \times 10^{-3}$). The two markers 10-32/357 and 10-33/234 showed weak association when tested independently.

The biallelic marker 10-35/390 is located in the genomic sequence of FLAP. Therefore, the association studies results show that a polymorphism of the FLAP gene seems to be related to asthma. The biallelic marker 10-35/390 can be then used in diagnostics with a test based on this marker or on a combination of biallelic markers comprising this marker.

Example 8

Association Studies: Haplotype Frequency Analysis

One way of increasing the statistical power of individual markers, is by performing haplotype association analysis.

Haplotype analysis for association of FLAP markers and asthma was performed by estimating the frequencies of all possible haplotypes comprising biallelic markers selected from the group consisting of 10-253/298, 10-32/357, 10-33/175, 10-33/234, 10-33/327, 10-35/358, 10-35/390, 12-628/306, and 12-629/241 in the asthmatic and Caucasian US control populations described in Example 7, and comparing these frequencies by means of a chi square statistical test (one degree of freedom). Haplotype estimations were performed by applying the Expectation-Maximization (EM) algorithm (Excoffier L & Slatkin M, 1995), using the EM-HAPLO program (Hawley M E, Pakstis A J & Kidd K K, 1994).

The most significant haplotypes obtained are shown in FIG. 3.

The preferred two-markers haplotypes, described in FIG. 3 as HAP1 to HAP7, comprise either the marker 10-33/234 (allele A) or the marker 10-35/390 (allele T). The more preferred two-markers haplotype HAP1 (A at 10-33/234 and T at 10-35/390) presented a p-value of $8.2 \times 10^{-4}$ and an odd-ratio of 1.61. Estimated haplotype frequencies were 28.3% in the cases and 19.7% in the US controls. Two other two-haplotypes HAP2 (A at 10-33/234 and G at 12-629/241) and HAP3 (T at 10-33/327 and T at 10-33/390) presented respectively a p-value of $1.6 \times 10^{-3}$ and $1.8 \times 10^{-3}$, an odd-ratio of 1.65 and 1.53 and haplotypes frequencies of 0.305 and 0.307 for asthmatic population and of 0.210 and 0.224 for US control population.

Preferred three-markers haplotypes comprise the marker 10-33/234 (allele A) and the marker 10-35/390 (allele T): HAP37, HAP38, HAP39 and HAP41. The more preferred three-markers haplotype HAP37 (A at 10-33/234, T at 10-33/390 and C at 12-628/306) presented a p-value of $8.6 \times 10^{-4}$ and an odd-ratio of 1.76. Estimated haplotype frequencies were 26.5% in the cases and 17.1% in the US controls. A further three-markers haplotype HAP40 (A at 10-33/234, G at 12-628/306 and G at 12-629/241) is also significant.

Four-markers haplotypes (HAP121 to HAP125), five-markers haplotypes (HAP 247 and 248) and a six-markers haplotype (HAP373) showed significant p-values. They all comprise the marker 10-33/234 (allele A) and the marker 10-35/390 (allele T), except the haplotype HAP124 which does not comprise the marker 10-35/390. The other markers are chosen from the group consisting of 10-235/298 (allele C), 10-35/358 (allele G), 12-628/306 (allele C) and 12-629/241 (allele G).

The more preferred haplotype comprising A at 10-33/234 and T at 10-35/390 (HAP1 in FIG. 3) is also significant in a haplotype frequency analysis with asthmatic population and Caucasian French controls. Indeed, this haplotype presented a p-value of $2.7 \times 10^{-3}$ and an odd-ratio of 1.67. Estimated haplotype frequencies were 28.3% in the cases and 19.2% in the French controls (see FIG. 4).

The haplotype HAP1 is the more preferred haplotype of the invention. It can be used in diagnosis of asthma. Moreover, most of the significant haplotypes associated with asthma comprise the biallelic marker 10-35/390 (allele A) and could also be used in diagnosis.

The statistical significance of the results obtained for the haplotype analysis was evaluated by a phenotypic permutation test reiterated 1000 or 10,000 times on a computer. For this computer simulation, data from the asthmatic and control individuals were pooled and randomly allocated to two groups which contained the same number of individuals as the case-control populations used to produce the data summarized in FIG. 3. A haplotype analysis was then run on these artificial groups for the 2 markers included in the haplotype HAP1 which, showed the strongest association with asthma. This experiment was reiterated 1000 and 10,000 times and the results are shown in FIG. 4. These results demonstrate that among 1000 iterations none and among 10,000 iterations only 1 of the obtained haplotypes had a p-value comparable to the one obtained for the haplotype HAP1. These results clearly validate the statistical significance of the association between this haplotype and asthma.

Example 9

Preparation of Antibody Compositions to the 127-Ile Variant of FLAP

Substantially pure protein or polypeptide is isolated from transfected or transformed cells containing an expression vector encoding the FLAP protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the FLAP protein or a portion thereof can be prepared from murine hybridomas according to the classical method of Kohler, G. and Milstein, C., (1975) or derivative methods thereof. Also see Harlow, E., and D. Lane. 1988.

Briefly, a mouse is repetitively inoculated with a few micrograms of the FLAP protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogeneous epitopes in the FLAP protein or a portion thereof can be prepared by immunizing suitable non-human animal with the FLAP protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for FLAP concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

While the preferred embodiment of the invention has been illustrated and described, it will be appreciated that various changes can be made therein by the one skilled in the art without departing from the spirit and scope of the invention.

REFERENCES

The following references are cited herein and are incorporated herein by reference in their entireties:

Abbondanzo S J et al., 1993, Methods in Enzymology, Academic Press, New York, pp. 803-823
Abramovitz M, Wong E, Cox M E, Richardson C D, Li C, & Vickers P J, *Eur J Biochem* 1993;215(1):105-111
Altschul et al., 1990, *J. Mol. Biol.* 215(3):403-410
Altschul et al., 1993, Nature Genetics 3:266-272
Altschul et al., 1997, Nuc. Acids Res. 25:3389-3402
Anton M. et al., 1995, J. Virol., 69 : 4600-4606
Araki K et al. (1995) *Proc. Natl. Acad. Sci. USA.* 92(1):160-4.
Ausubel et al. (1989) Current Protocols in Molecular Biology, Green Publishing Associates and Wiley Interscience, N.Y.
Baubonis W. (1993) *Nucleic Acids Res.* 21(9):2025-9.
Beaucage et al., *Tetrahedron Lett* 1981, 22: 1859-1862
Bradley A., 1987, Production and analysis of chimaeric mice. In: E. J. Robertson (Ed.), Teratocarcinomas and embryonic stem cells: A practical approach. IRL Press, Oxford, pp. 113.
Brown E L, Belagaje R, Ryan M J, Khorana H G, *Methods Enzymol* 1979;68:109-151
Brutlag et al. Comp. App. Biosci. 6:237-245, 1990
Capecchi, M. R. (1989a) *Science,* 244:1288-1292
Capecchi, M. R. (1989b) *Trends Genet.,* 5:70-76
Chai H. et al. (1993) *Biotechnol. Appl. Biochem.* 18:259-273.
Charleson S, Prasit P. Leger S, Gillard J W, Vickers P J, Mancini J A, Charleson P, Guay J, Ford-Hutchinson A W, Evans J F, *Mol Pharmacol* 1992;41(5):873-879
Chee et al. (1996) *Science.* 274:610-614.
Chen et al. (1987) *Mol. Cell. Biol.* 7:2745-2752.
Chou J. Y., 1989, Mol. Endocrinol., 3: 1511-1514.
Clark A. G. (1990) *Mol. Biol. Evol.* 7:111-122.
Compton J. (1991) *Nature.* 350(6313):91-92.
Davis L. G., M. D. Dibner, and J. F. Battey, Basic Methods in Molecular Biology, ed., Elsevier Press, NY, 1986
Dempster et al., (1977) *J. R. Stat. Soc.,* 39B:1-38.
Dixon et al., 1988, *PNAS* 85, pp. 416-420
Dixon R A, Diehl R E, Opas E, Rands E, Vickers P J, Evans J F, Gillard J W, & Miller D K, *Nature* 1990;343(6255):282-284
Eckner R. et al. (1991) *EMBO J.* 10:3513-3522.
Edwards et Leatherbarrow, *Analytical Biochemistry,* 246, 1-6 (1997)
Engvall, E., Meth. Enzymol. 70:419 (1980)
Excoffier L. and Slatkin M. (1995) Mol. Biol. Evol., 12(5): 921-927.
Feldman and Steg, 1996, Medecine/Sciences, synthese, 12:47-55
Fisher, D., Chap. 42 in: Manual of Clinical Immunology, 2d Ed. (Rose and Friedman, Eds.) Amer. Soc. For Microbiol., Washington, D.C. (1980)
Flotte et al. (1992) *Am. J. Respir. Cell Mol. Biol.* 7:349-356.
Fodor et al. (1991) *Science* 251:767-777.
Fraley et al. (1979) *Proc. Natl. Acad Sci. USA.* 76:3348-3352.
Fuller S. A. et al. (1996) *Immunology in Current Protocols in Molecular Biology, Ausubel et al. Eds, John Wiley & Sons, Inc., USA.*
Furth P. A. et al. (1994) *Proc. Natl. Acad. Sci USA.* 91:9302-9306.
Geysen H. Mario et al. 1984. Proc. Natl. Acad. Sci. U.S.A. 81:3998-4002
Ghosh and Bacchawat, 1991, *Targeting of liposomes to hepatocytes,* IN: *Liver Diseases, Targeted diagnosis and therapy using specific receptors and ligands.* Wu et al. Eds., Marcel Dekeker, New York, pp. 87-104.
Gonnet et al., 1992, Science 256:1443-1445
Gopal (1985) *Mol. Cell. Biol.,* 5:1188-1190.
Gossen M. et al. (1992) *Proc. Natl. Acad. Sci. USA.* 89:5547-5551.
Gossen M. et al. (1995) *Science.* 268:1766-1769.
Graham et al. (1973) *Virology* 52:456-457.
Grompe, M. (1993) *Nature Genetics.* 5:111-117.
Grompe, M. et al. (1989) *Proc. Natl. Acad. Sci. U.S.A.* 86:5855-5892.
Gu H. et al. (1993) *Cell* 73:1155-1164.
Gu H. et al. (1994) *Science* 265:103-106.
Guatelli J C et al. *Proc. Natl. Acad. Sci. USA.* 35:273-286.
Hacia J G, Brody L C, Chee M S, Fodor S P, Collins F S, *Nat Genet* 1996;14(4):441-447
Haff L. A. and Smirnov I. P. (1997) *Genome Research,* 7:378-388.
Hames B. D. and Higgins S. J. (1985) *Nucleic Acid Hybridization: A Practical Approach.* Hames and Higgins Ed., IRL Press, Oxford.
Harju L, Weber T, Alexandrova L, Lukin M, Ranki M, Jalanko A, *Clin Chem* 1993;39(11Pt 1):2282-2287
Harland et al. (1985) *J. Cell. Biol.* 101:1094-1095.

Harlow, E., and D. Lane. 1988. Antibodies A Laboratory Manual. Cold Spring Harbor Laboratory. pp. 53-242

Hawley M. E. et al. (1994) *Am. J. Phys. Anthropol.* 18:104.

Henikoff and Henikoff, 1993, Proteins 17:49-61

Higgins et al., 1996, Methods Enzymol. 266:383-402

Hillier L. and Green P. *Methods Appl.*, 1991, 1: 124-8.

Hoess et al. (1986) *Nucleic Acids Res.* 14:2287-2300.

Huang L. et al. (1996) *Cancer Res* 56(5):1137-1141.

Huygen et al. (1996) *Nature Medicine.* 2(8):893-898.

Julan et al. (1992) *J. Gen. Virol.* 73:3251-3255.

Kanegae Y. et al., *Nucl. Acids Res.* 23:3816-3821.

Karlin and Altschul, 1990, Proc. Natl. Acad. Sci. USA 87:2267-2268

Kennedy B P, Diehl R E, Boie Y, Adam M, Dixon R A, *J Biol Chem* 1991;266(13):8511-8516

Kim U-J. et al. (1996) *Genomics* 34:213-218.

Klein et al. (1987) *Nature.* 327:70-73.

Kohler, G. and Milstein, C., Nature 256:495 (1975)

Koller et al. (1992) *Annu. Rev. Immunol.* 10:705-730.

Kozal M J, Shah N, Shen N, Yang R, Fucini R, Merigan T C, Richman D D, Morris D, Hubbell E, Chee M, Gingeras T R, *Nat Med* 1996;2(7):753-759

Landegren U. et al. (1998) *Genome Research,* 8:769-776.

Lange K. (1997) *Mathematical and Statistical Methods for Genetic Analysis*. Springer, New York.

Lenhard T. et al. (1996) *Gene.* 169:187-190.

Linton M. F. et al. (1993) *J. Clin. Invest.* 92:3029-3037.

Liu Z. et al. (1994) *Proc. Natl. Acad. Sci. USA.* 91: 4528-4262.

Livak K J, Hainer J W, *Hum Mutat* 1994;3(4):379-385

Livak et al., *Nature Genetics,* 9:341-342, 1995

Lockhart et al. *Nature Biotechnology* 14: 1675-1680, 1996

Mansour S. L. et al. (1988) *Nature.* 336:348-352.

Manz et al., *Adv in Chromatogr* 1993; 33:1-66

Marshall R. L. et al. (1994) *PCR Methods and Applications.* 4:80-84.

McCormick et al. (1994) *Genet. Anal. Tech. Appl.* 11:158-164.

McLaughlin B. A. et al. (1996) *Am. J. Hum. Genet.* 59:561-569.

Muzyczka et al. (1992) *Curr. Topics in Micro. and Immunol.* 158:97-129.

Nada S. et al. (1993) *Cell* 73:1125-1135.

Nagy A. et al., 1993, Proc. Natl. Acad. Sci. USA, 90: 8424-8428.

Narang S A, Hsiung H M, Brousseau R, *Methods Enzymol* 1979;68:90-98

Neda et al. (1991) *J. Biol. Chem.* 266:14143-14146.

Newton et al. (1989) *Nucleic Acids Res.* 17:2503-2516.

Nickerson D. A. et al. (1990) *Proc. Natl Acad. Sci. U.S.A.* 87:8923-8927.

Nicolau C. et al., 1987, Methods Enzymol., 149:157-76.

Nicolau et al. (1982) *Biochim. Biophys. Acta.* 721:185-190.

Nyren P, Pettersson B, Uhlen M, *Anal Biochem* 1993;208(1):171-175

O'Reilly et al. (1992) *Baculovirus Expression Vectors: A Laboratory Manual*. W. H. Freeman and Co., New York.

Ohno et al. (1994) *Science.* 265:781-784.

Orita et al. (1989) *Proc. Natl. Acad. Sci. U.S.A.* 86: 2776-2770.

Ouchteilony, O. et al., Clap. 19 in: Handbook of Experimental Immunology D. Wier (ed) Blackwell (1973)

Pastinen et al., *Genome Research* 1997; 7:606-614

Pearson and Lipman, 1988, Proc. Natl. Acad. Sci. USA 85(8):2444-2448

Pease S. ans William R. S., 1990, Exp. Cell. Res., 190: 209-211.

Perlin et al. (1994) *Am. J. Hum. Genet.* 55:777-787.

Pietu et al. *Genome Research* 6:492-503, 1996

Potter et al. (1984) *Proc. Natl. Acad. Sci. U.S.A.* 81(22): 7161-7165.

Reid L. H. et al. (1990) Proc. Natl. Acad. Sci. U.S.A. 87:4299-4303.

Robertson E., 1987, Embryo-derived stem cell lines. In: E. J. Robertson Ed. *Teratocarcinomas and embrionic stem cells: a practical approach*. IRL Press, Oxford, pp. 71.

Roth J. A. et al. (1996) *Nature Medicine.* 2(9):985-991.

Roux et al. (1989) *Proc. Natl. Acad. Sci. U.S.A.* 86:9079-9083.

Ruano et al. (1990) *Proc. Natl. Acad Sci. U.S.A.* 87:6296-6300.

Sambrook, J., Fritsch, E. F., and T. Maniatis. (1989) *Molecular Cloning: A Laboratory Manual.* 2ed. Cold Spring Harbor Laboratory, Cold Spring Harbor, N.Y.

Samson M, et al. (1996) *Nature,* 382(6593):722-725.

Samulski et al. (1989) *J. Virol.* 63:3822-3828.

Sanchez-Pescador R. (1988) *J. Clin. Microbiol.* 26(10): 1934-1938.

Sarkar, G. and Sommer S. S. (1991) *Biotechniques.*

Sauer B. et al. (1988) *Proc. Natl. Acad. Sci. U.S.A.* 85:5166-5170.

Schedl A. et al., 1993a, Nature, 362: 258-261.

Schedl et al., 1993b, Nucleic Acids Res., 21: 4783-4787.

Schena et al. *Proc. Natl. Acad. Sci. U.S.A.* 93:10614-10619, 1996

Schena et al. *Science* 270:467-470, 1995

Schneider et al. (1997) *Arlequin: A Software For Population Genetics Data Analysis. University of Geneva.*

Schwartz and Dayhoff, eds., 1978, Matrices for Detecting Distance Relationships: Atlas of Protein Sequence and Structure, Washington: National Biomedical Research Foundation Sczakiel G. et al. (1995) *Trends Microbiol.* 3(6):213-217.

Shay J. W. et al., 1991, Biochem. Biophys. Acta, 1072: 1-7.

Sheffield, V. C. et al. (1991) *Proc. Natl. Acad. Sci. U.S.A.* 49:699-706.

Shizuya et al. (1992) *Proc. Natl. Acad. Sci. U.S.A.* 89:8794-8797.

Shoemaker D D, Lashkari D A, Morris D, Mittmann M, Davis R W, *Nat Genet* 1996;14(4):450-456

Smith (1957) *Ann. Hum. Genet.* 21:254-276.

Smith et al. (1983) *Mol. Cell. Biol.* 3:2156-2165.

Sosnowski R G, Tu E, Butler W F, O'C.onnell J P, Heller M J, *Proc Natl Acad Sci USA* 1997;94(4):1119-1123

Sternberg N. L. (1992) *Trends Genet.* 8:1-16.

Sternberg N. L. (1994) *Mamm. Genome.* 5:397-404.

Stryer, L., *Biochemistry,* 4th edition, 1995

Syvanen A C, *Clin Chim Acta* 1994;226(2):225-236

Tacson et al. (1996) *Nature Medicine.* 2(8):888-892.

Te Riele et al. (1990) Nature. 348:649-651.

Thomas K. R. et al. (1986) *Cell.* 44:419-428.

Thomas K. R. et al. (1987) *Cell.* 51:503-512.

Thompson et al., 1994, Nucleic Acids Res. 22(2):4673-4680

Tsuzuki, T. and Rancourt, D. E. (1998) Nucleic Acids Res., 26(4):988-993

Tur-Kaspa et al. (1986) *Mol. Cell. Biol.* 6:716-718.

Tyagi et al. (1998) *Nature Biotechnology.* 16:49-53.

Urdea M. S. (1988) *Nucleic Acids Research.* 11:4937-4957.

Urdea M. S. et al. (1991) *Nucleic Acids Symp. Ser.* 24:197-200.

Vaitukaitis, J. et al. J. Clin. Endocrinol. Metab. 33:988-991 (1971)
Van der Lugt et al. (1991) *Gene.* 105:263-267.
Vlasak R. et al. (1983) *Eur. J Biochem.* 135:123-126.
Wabiko et al. (1986) *DNA.*5(4):305-314.
Walker et al. (1996) *Clin. Chem.* 42:9-13.
Weir, B. S. (1996) *Genetic data Analysis II. Methods for Discrete population genetic Data*, Sinauer Assoc., Inc., Sunderland, Mass., U.S.A.
White, M. B. et al. (1992) *Genomics.* 12:301-306.
White, M. B. et al. (1997) *Genomics.* 12:301-306.
Wong et al. (1980) *Gene.* 10:87-94.
Wood S. A. et al., 1993, Proc. Natl. Acad. Sci. USA, 90: 4582-4585.
Wu and Wu (1987) *J. Biol. Chem.* 262:4429-4432.
Wu and Wu (1988) *Biochemistry.* 27:887-892.
Wu et al. (1989) *Proc. Natl. Acad. Sci. U.S.A.* 86:2757.
Yagi T. et al. (1990) *Proc. Natl. Acad. Sci. U.S.A.* 87:9918-9922.
Zou Y. R. et al. (1994) *Curr. Biol.* 4:1099-1103.

We claim:

1. A method of determining whether an individual is at risk of developing asthma comprising the steps of:
   (a) obtaining a biological sample comprising a nucleic acid from said individual;
   (b) determining the identity of a biallelic marker at position 16347 of SEQ ID NO: 1 and 38681 of SEQ ID NO: 1 within said biological sample; and
   (c) evaluating whether an individual is at increased risk of asthma; wherein the presence of both an A at position 16347 of SEQ ID NO: 1 and a T at position 38681 of SEQ ID NO: 1 is indicative of an increased risk for developing asthma.

2. The method according to claim 1, further comprising the step of amplifying a portion of the FLAP gene comprising said biallelic marker prior to determining the identity of said nucleotide.

3. The method according to claim 2, wherein said amplifying is performed by PCR.

4. The method according to claim 1, wherein said nucleotide is determined by performing a microsequencing assay.

5. The method according to claim 1, wherein said nucleotide is determined by performing a hybridization assay.

6. The method according to claim 1, wherein said nucleotide is determined by performing a sequencing assay.

* * * * *

UNITED STATES PATENT AND TRADEMARK OFFICE
CERTIFICATE OF CORRECTION

PATENT NO. : 7,494,777 B2
APPLICATION NO. : 11/512789
DATED : February 24, 2009
INVENTOR(S) : Marta Blumenfeld, Ilya Chumakov and Lydie Bougueleret It is certified that error appears in the above-identified patent and that said Letters Patent is hereby corrected as shown below:

Column 48,
Line 47, "T+ and T- of a" should read --T+ and T- populations of a--.

Column 53,
Line 59, "preferably $1 \times 10^{10-6}$" should read --preferably $1 \times 10^{-6}$--.

Column 57,
Line 21, "$pr(h_k, h_l)=pr(h_k)^2$ if $h_k=h_l$, $pr_{(k,} h_l)=2pr(h_k).pr(h_l)$ if" should read
--$pr(h_k, h_l)=pr(h_k)^2$ if $h_k=h_l$, $pr(h_{k,} h_l)=2pr(h_k).pr(h_l)$ if--.

Column 58,
Line 23, "having allele as at" should read --having allele $a_i$ at--.
Line 65, "$D_{aija}^{>0}$" should read --$D_{aiaj} >0$--.

Column 92,
Table 3, Column 6 Heading,
"Complementary position range of misrosequencing primer mis. 2 in SEQ ID No 1" should read
--Complementary position range of microsequencing primer mis. 2 in SEQ ID No 1--.

Column 93,
Table 3, Column 6 Heading,
"Complementary position range of misrosequencing primer mis. 2 in SEQ ID No 1" should read
--Complementary position range of microsequencing primer mis. 2 in SEQ ID No 1--.

Column 95,
Line 41, "A at 10-33/234, G at" should read --A at 10-33/234, C at--.

UNITED STATES PATENT AND TRADEMARK OFFICE
CERTIFICATE OF CORRECTION

PATENT NO. : 7,494,777 B2
APPLICATION NO. : 11/512789
DATED : February 24, 2009
INVENTOR(S) : Marta Blumenfeld, Ilya Chumakov and Lydie Bougueleret It is certified that error appears in the above-identified patent and that said Letters Patent is hereby corrected as shown below:

Column 99,
Line 63, "Clap. 19" should read --Chap. 19--.

Signed and Sealed this

Twelfth Day of May, 2009

JOHN DOLL
*Acting Director of the United States Patent and Trademark Office*